US 12,171,815 B2

(12) United States Patent
Kweon et al.

(10) Patent No.: US 12,171,815 B2
(45) Date of Patent: Dec. 24, 2024

(54) METHOD FOR SAFELY PRODUCING BOTULINUM NEUROTOXIN

(71) Applicant: MVRIX CO., LTD., Hwaseong-si (KR)

(72) Inventors: Dae-Hyuk Kweon, Suwon-si (KR); Joon-Bum Park, Suwon-si (KR); Yong-Jun Kim, Suwon-si (KR); Min-Ju Kim, Suwon-si (KR); Won-beom Park, Suwon-si (KR)

(73) Assignee: MVRIX CO., LTD., Hwaseong-si (KR)

( * ) Notice: Subject to any disclaimer, the term of this patent is extended or adjusted under 35 U.S.C. 154(b) by 383 days.

(21) Appl. No.: 17/637,338

(22) PCT Filed: Dec. 18, 2020

(86) PCT No.: PCT/KR2020/018623
§ 371 (c)(1),
(2) Date: Feb. 22, 2022

(87) PCT Pub. No.: WO2021/125866
PCT Pub. Date: Jun. 24, 2021

(65) Prior Publication Data
US 2022/0280617 A1    Sep. 8, 2022

(30) Foreign Application Priority Data
Dec. 18, 2019    (KR) ................ 10-2019-0169553

(51) Int. Cl.
*A61K 38/48*    (2006.01)
*A61P 25/00*    (2006.01)
*C07K 14/33*    (2006.01)
*C12N 15/70*    (2006.01)

(52) U.S. Cl.
CPC .......... *A61K 38/4893* (2013.01); *A61P 25/00* (2018.01); *C07K 14/33* (2013.01); *C12N 15/70* (2013.01)

(58) Field of Classification Search
CPC ..... A61K 38/4893; A61K 38/00; A61P 25/00; C07K 14/33; C07K 2319/00; C07K 2319/92; C12N 15/70; C12N 9/52; C12N 2840/445; C12Y 304/24069; Y02A 50/30
See application file for complete search history.

(56) References Cited

U.S. PATENT DOCUMENTS

| 2003/0166238 | A1 | 9/2003 | Shone et al. | |
|---|---|---|---|---|
| 2006/0024794 | A1* | 2/2006 | Li | C07K 14/33 536/23.7 |
| 2008/0064092 | A1 | 3/2008 | Foster et al. | |
| 2010/0196421 | A1 | 8/2010 | Ichtchenko et al. | |
| 2011/0028691 | A1 | 2/2011 | Shone et al. | |
| 2013/0345398 | A1* | 12/2013 | Smith | C07K 14/33 435/254.2 |

FOREIGN PATENT DOCUMENTS

| CN | 101107361 A | 1/2008 |
|---|---|---|
| KR | 10-2018-0130452 A | 12/2018 |
| KR | 10-2019-0026834 A | 3/2019 |
| WO | 02/36758 A2 | 5/2002 |
| WO | 2014/110393 A1 | 7/2014 |

OTHER PUBLICATIONS

Thomas Weber et al., "SNAREpins: Minimal Machinery for Membrane Fusion", Cell, 1998, vol. 92, pp. 759-772 (14 pages total).
Bal Ram Singh, "Critical Aspects of Bacterial Protein Toxins", Natural Toxins II, 1996, Chapter 4, pp. 63-84 (23 pages total).
Yu Zhou et al., "Cloning, high-level expression, single-step purification, and binding activity of His6-tagged recombinant type B botulinum neurotoxin heavy chain transmembrane and binding domain", Protein Expression and Purification, 2004, vol. 34, Issue 1, pp. 8-16 (1 page total).
Philip A. Band et al., "Recombinant Derivatives of Botulinum Neurotoxin A Engineered for Trafficking Studies and Neuronal Delivery", Protein Expr Purif., 2010, vol. 71, No. 1, pp. 62-73 (25 pages total).
Giampietro Schiavo et al., "Botulinum Neurotoxins are Zinc Proteins", The Journal or Biological Chemistry, 1992, vol. 267, No. 33, pp. 23479-23483 (5 pages total).
J. Oliver Dolly et al., "Acceptors for botulinum neurotoxin reside on motor nerve terminals and mediate its internalization", Nature, 1984, vol. 307, pp. 457-460 (4 pages total).
Thomas Binz et al., "Cell entry strategy of clostridial neurotoxins", Journal of Neurochemistry, 2009, vol. 109, pp. 1584-1595 (12 pages total).
Ornella Rossetto et al., "Botulinum neurotoxins: genetic, structural and mechanistic insights", Nature Reviews Microbiology, 2014, pp. 1-15 (15 pages total).
Neel H. Shah et al., "Inteins: nature's gift to protein chemists", Chemical Science, 2014, vol. 5, pp. 446-461 (16 pages total).
Ester Fernandez-Salas et al., "Botulinum Neurotoxin Serotype a Specific Cell-Based Potency Assay to Replace the Mouse Bioassay", PLoS ONE, 2012, vol. 7, Issue 11, e49516, pp. 1-13 (13 pages total).

(Continued)

Primary Examiner — Iqbal H Chowdhury
(74) Attorney, Agent, or Firm — Sughrue Mion, PLLC

(57) ABSTRACT

The present invention relates to a method for producing botulinum toxin in various fragments to then be reassembled, for safely producing same. In the present invention, devised is a method in which: botulinum toxin is produced in fragments by cleaving light and heavy chains thereof into two or three pieces, respectively, and then combined as a full-length toxin, thereby allowing high complexity in production, due to toxicity, as well as low safety and economic feasibility, to be overcome; production of water-soluble botulinum toxin is enabled by using bacteria, thereby markedly shortening the production time as compared to existing production methods; and conjugation of the produced fragments with other proteins and nanoparticles is also enabled, thereby increasing the pharmaceutical extensibility of the toxin.

2 Claims, 26 Drawing Sheets

Specification includes a Sequence Listing.

(56) References Cited

OTHER PUBLICATIONS

Bijan Zakeri et al., "Peptide tag forming a rapid covalent bond to a protein, through engineering a bacterial adhesin", PNAS, 2012, vol. 109, No. 12, E690-E697 (8 pages total).

Choi Jong-hyun et al., "Development trend of synthetic biology parts using Intein", 2014 (11 pages total).

International Search Report dated Apr. 8, 2021 in International Application No. PCT/KR2020/018623.

Notice of Opinion Submission dated Jul. 30, 2023 for KR Application No. 10-2020-0178099.

Notice of Allowance dated Nov. 10, 2023 for KR Application No. 10-2020-0178099.

L. L. Simpson, et al., "The Binding of Botulinum Toxin to Membrane Lipids: Sphingolipids, Steroids and Fatty Acids", Journal of Neurochemistry, Sep. 1971, vol. 18, Issue 9, pp. 1751-1759, Abstract (1 page total).

Baskaran Thyagarajan, et al., "Perturbation to Cholesterol at the Neuromuscular Junction Confers Botulinum Neurotoxin A Sensitivity to Neonatal Mice", Toxicological Sciences, 2017, vol. 159, No. 1, pp. 179-188 (10 pages total).

Supplementary European Search Report dated Nov. 17, 2022 in European Application No. 20 90 0935.

Frederic Darios et al., "SNARE tagging allows stepwise assembly of a multimodal medicinal toxin", Proceedings of the National Academy of Sciences, 2010, vol. 107, No. 42, pp. 18197-18201 (5 pages total).

Sicai Zhang et al., "Identification and characterization of a novel botulinum neurotoxin", Nature Communications, 2017, vol. 8, No. 1, pp. 1-10 (10 pages total).

Li Li et al., "High-Level Expression, Purification, and Characterization of Recombinant Type A Botulinum Neurotoxin Light Chain", Protein Expression and Purification, 1999, vol. 7, pp. 339-344 (6 pages total).

Robert P. Webb, "Engineering of Botulinum Neurotoxins for Biomedical Applications", Toxins, 2018, vol. 10, No. 231, pp. 1-25 (25 pages total).

\* cited by examiner

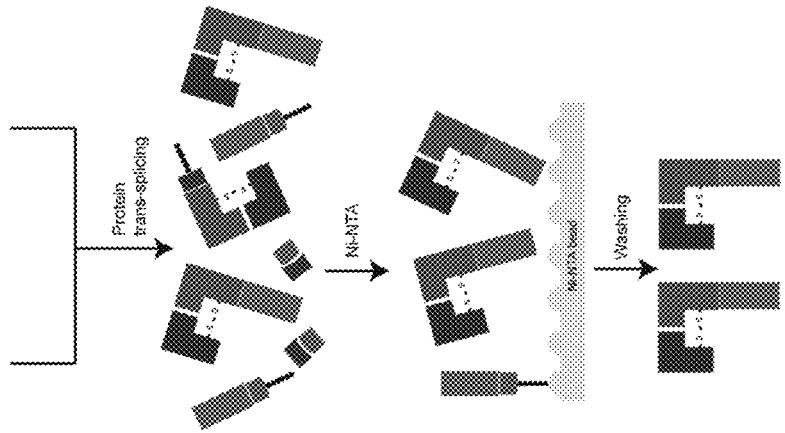
FIG. 3b
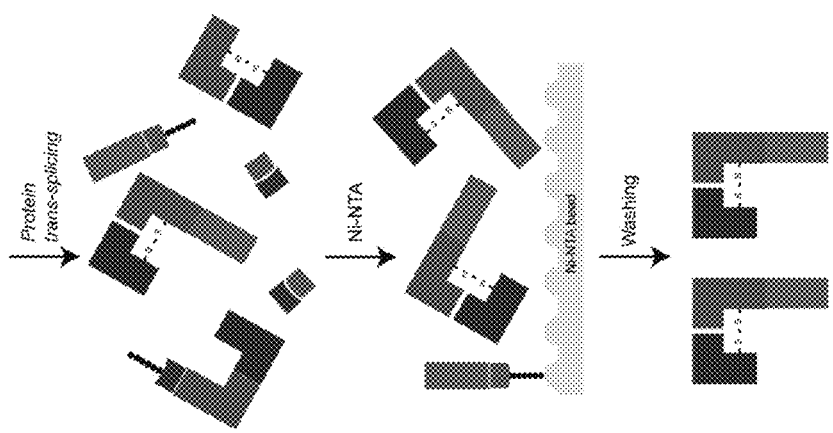

His – TEV – LC : 51.8 kDa

His – Cfa$^C$– H$_C$ : 54.4 kDa

LCH$_N$-Cfa$^N$-His : 112.65 kDa

FIG. 6b

LCTEVH$_N$-Cfa$^N$-His : 112.4 kDa

FIG. 7

| | M | 0h | | 15min | | 30min | | 1h | |
|---|---|---|---|---|---|---|---|---|---|
| (kDa) | | R | NR | R | NR | R | NR | R | NR |

180 ← BoNT : 150 kDa
130 ← LcHn – cfaN – His6 : 112.754 kDa
100
70
55       His6 – CfaC – Hc : 54.443 kDa LCHn-CfaN + CfaC-Hc R : Reducing
NR : Non - reducing

FIG. 10

SEQUENCE LISTING

```
<160> NUMBER OF SEQ ID NOS: 76

<210> SEQ ID NO 1
<211> LENGTH: 448
<212> TYPE: PRT
<213> ORGANISM: Artificial Sequence
<220> FEATURE:
<223> OTHER INFORMATION: Lc-A2 subtype(Q45894)

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
```

```
                    260                 265                 270
Phe Ile Asp Ser Leu Gln Glu Asn Glu Phe Arg Leu Tyr Tyr Tyr Asn
            275                 280                 285
Lys Phe Lys Asp Val Ala Ser Thr Leu Asn Lys Ala Lys Ser Ile Ile
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Asn Phe Lys Val Ile Asn Arg Lys Thr Tyr Leu Asn
            355                 360                 365
Phe Asp Lys Ala Val Phe Arg Ile Asn Ile Val Pro Asp Glu Asn Tyr
            370                 375                 380
Thr Ile Lys Asp Gly Phe Asn Leu Lys Gly Ala Asn Leu Ser Thr Asn
385                 390                 395                 400
Phe Asn Gly Gln Asn Thr Glu Ile Asn Ser Arg Asn Phe Thr Arg Leu
                405                 410                 415
Lys Asn Phe Thr Gly Leu Phe Glu Phe Tyr Lys Leu Leu Cys Val Arg
            420                 425                 430
Gly Ile Ile Pro Phe Lys Thr Lys Ser Leu Asp Glu Gly Tyr Asn Lys
            435                 440                 445

<210> SEQ ID NO 2
<211> LENGTH: 426
<212> TYPE: PRT
<213> ORGANISM: Artificial Sequence
<220> FEATURE:
<223> OTHER INFORMATION: Hc-A2 subtype(Q45894)

<400> SEQUENCE: 2

Lys Asn Ile Val Asn Thr Ser Ile Leu Ser Ile Val Tyr Lys Lys Asp
1               5                   10                  15
Asp Leu Ile Asp Leu Ser Arg Tyr Gly Ala Lys Ile Asn Ile Gly Asp
            20                  25                  30
Arg Val Tyr Tyr Asp Ser Ile Asp Lys Asn Gln Ile Lys Leu Ile Asn
        35                  40                  45
Leu Glu Ser Ser Thr Ile Glu Val Ile Leu Lys Asn Ala Ile Val Tyr
    50                  55                  60
Asn Ser Met Tyr Glu Asn Phe Ser Thr Ser Phe Trp Ile Lys Ile Pro
65                  70                  75                  80
Lys Tyr Phe Ser Lys Ile Asn Leu Asn Asn Glu Tyr Thr Ile Ile Asn
                85                  90                  95
Cys Ile Glu Asn Asn Ser Gly Trp Lys Val Ser Leu Asn Tyr Gly Glu
            100                 105                 110
Ile Ile Trp Thr Leu Gln Asp Asn Lys Gln Asn Ile Gln Arg Val Val
        115                 120                 125
Phe Lys Tyr Ser Gln Met Val Asn Ile Ser Asp Tyr Ile Asn Arg Trp
    130                 135                 140
Ile Phe Val Thr Ile Thr Asn Asn Arg Leu Thr Lys Ser Lys Ile Tyr
145                 150                 155                 160
Ile Asn Gly Arg Leu Ile Asp Gln Lys Pro Ile Ser Asn Leu Gly Asn
                165                 170                 175
Ile His Ala Ser Asn Lys Ile Met Phe Lys Leu Asp Gly Cys Arg Asp
```

```
            180                 185                 190
Pro Arg Arg Tyr Ile Met Ile Lys Tyr Phe Asn Leu Phe Asp Lys Glu
            195                 200                 205

Leu Asn Glu Lys Glu Ile Lys Asp Leu Tyr Asp Ser Gln Ser Asn Ser
        210                 215                 220

Gly Ile Leu Lys Asp Phe Trp Gly Asn Tyr Leu Gln Tyr Asp Lys Pro
225                 230                 235                 240

Tyr Tyr Met Leu Asn Leu Phe Asp Pro Asn Lys Tyr Val Asp Val Asn
                245                 250                 255

Asn Ile Gly Ile Arg Gly Tyr Met Tyr Leu Lys Gly Pro Arg Gly Ser
            260                 265                 270

Val Val Thr Thr Asn Ile Tyr Leu Asn Ser Thr Leu Tyr Glu Gly Thr
        275                 280                 285

Lys Phe Ile Ile Lys Lys Tyr Ala Ser Gly Asn Glu Asp Asn Ile Val
            290                 295                 300

Arg Asn Asn Asp Arg Val Tyr Ile Asn Val Val Lys Asn Lys Glu
305                 310                 315                 320

Tyr Arg Leu Ala Thr Asn Ala Ser Gln Ala Gly Val Glu Lys Ile Leu
                325                 330                 335

Ser Ala Leu Glu Ile Pro Asp Val Gly Asn Leu Ser Gln Val Val Val
            340                 345                 350

Met Lys Ser Lys Asp Asp Gln Gly Ile Arg Asn Lys Cys Lys Met Asn
        355                 360                 365

Leu Gln Asp Asn Asn Gly Asn Asp Ile Gly Phe Ile Gly Phe His Leu
    370                 375                 380

Tyr Asp Asn Ile Ala Lys Leu Val Ala Ser Asn Trp Tyr Asn Arg Gln
385                 390                 395                 400

Val Gly Lys Ala Ser Arg Thr Phe Gly Cys Ser Trp Glu Phe Ile Pro
                405                 410                 415

Val Asp Asp Gly Trp Gly Glu Ser Ser Leu
            420                 425

<210> SEQ ID NO 3
<211> LENGTH: 422
<212> TYPE: PRT
<213> ORGANISM: Artificial Sequence
<220> FEATURE:
<223> OTHER INFORMATION: Hn-A2 subtype(Q45894)

<400> SEQUENCE: 3

Ala Leu Asn Asp Leu Cys Ile Lys Val Asn Asn Trp Asp Leu Phe Phe
1               5                   10                  15

Ser Pro Ser Glu Asp Asn Phe Thr Asn Asp Leu Asp Lys Val Glu Glu
            20                  25                  30

Ile Thr Ala Asp Thr Asn Ile Glu Ala Ala Glu Glu Asn Ile Ser Leu
        35                  40                  45

Asp Leu Ile Gln Gln Tyr Tyr Leu Thr Phe Asp Phe Asp Asn Glu Pro
    50                  55                  60

Glu Asn Ile Ser Ile Glu Asn Leu Ser Ser Asp Ile Ile Gly Gln Leu
65                  70                  75                  80

Glu Pro Met Pro Asn Ile Glu Arg Phe Pro Asn Gly Lys Lys Tyr Glu
                85                  90                  95

Leu Asp Lys Tyr Thr Met Phe His Tyr Leu Arg Ala Gln Glu Phe Glu
            100                 105                 110

His Gly Asp Ser Arg Ile Ile Leu Thr Asn Ser Ala Glu Glu Ala Leu
```

|  |  |  | 115 |  |  |  | 120 |  |  |  | 125 |  |
|---|---|---|---|---|---|---|---|---|---|---|---|---|

Leu Lys Pro Asn Val Ala Tyr Thr Phe Phe Ser Ser Lys Tyr Val Lys
          130                 135             140

Lys Ile Asn Lys Ala Val Glu Ala Phe Met Phe Leu Asn Trp Ala Glu
145                 150                 155             160

Glu Leu Val Tyr Asp Phe Thr Asp Glu Thr Asn Glu Val Thr Thr Met
               165                 170             175

Asp Lys Ile Ala Asp Ile Thr Ile Val Pro Tyr Ile Gly Pro Ala
          180                 185             190

Leu Asn Ile Gly Asn Met Leu Ser Lys Gly Glu Phe Val Glu Ala Ile
          195                 200             205

Ile Phe Thr Gly Val Val Ala Met Leu Glu Phe Ile Pro Glu Tyr Ala
          210                 215             220

Leu Pro Val Phe Gly Thr Phe Ala Ile Val Ser Tyr Ile Ala Asn Lys
225                 230                 235             240

Val Leu Thr Val Gln Thr Ile Asn Asn Ala Leu Ser Lys Arg Asn Glu
               245                 250             255

Lys Trp Asp Glu Val Tyr Lys Tyr Thr Val Thr Asn Trp Leu Ala Lys
          260                 265             270

Val Asn Thr Gln Ile Asp Leu Ile Arg Glu Lys Met Lys Lys Ala Leu
          275                 280             285

Glu Asn Gln Ala Glu Ala Thr Lys Ala Ile Ile Asn Tyr Gln Tyr Asn
290                 295                 300

Gln Tyr Thr Glu Glu Glu Lys Asn Asn Ile Asn Phe Asn Ile Asp Asp
305                 310                 315             320

Leu Ser Ser Lys Leu Asn Glu Ser Ile Asn Ser Ala Met Ile Asn Ile
               325                 330             335

Asn Lys Phe Leu Asp Gln Cys Ser Val Ser Tyr Leu Met Asn Ser Met
          340                 345             350

Ile Pro Tyr Ala Val Lys Arg Leu Lys Asp Phe Asp Ala Ser Val Arg
          355                 360             365

Asp Val Leu Leu Lys Tyr Ile Tyr Asp Asn Arg Gly Thr Leu Val Leu
          370                 375             380

Gln Val Asp Arg Leu Lys Asp Glu Val Asn Asn Thr Leu Ser Ala Asp
385                 390                 395             400

Ile Pro Phe Gln Leu Ser Lys Tyr Val Asp Asn Lys Lys Leu Leu Ser
               405                 410             415

Thr Phe Thr Glu Tyr Ile
          420

<210> SEQ ID NO 4
<211> LENGTH: 4341
<212> TYPE: DNA
<213> ORGANISM: Artificial Sequence
<220> FEATURE:
<223> OTHER INFORMATION: pColaduet his-SNAP25

<400> SEQUENCE: 4

```
ggggaattgt gagcggataa caattcccct gtagaaataa ttttgtttaa ctttaataag      60
gagatatacc atgggcagca gccatcacca tcatcaccac agccaggatc caatggccga     120
ggacgcagac atgcgtaatg agctggagga gatgcagagg agggctgacc agctggctga     180
tgagtccctg gaaagcaccc gtcgcatgct gcagctggtt gaagagagta agatgctgg      240 catcaggact ttggttatgt tggatgagca aggcgaacaa ctggaacgca ttgaggaagg     300
```

```
gatggaccaa atcaataagg acatgaaaga agcagaaaag aatttgacgg acctaggaaa    360
attcgccggc cttgccgtgg cccccgccaa caagcttaaa tccagtgatg cttacaaaaa    420 agcctgggc  aataatcagg atggagtagt ggccagccag cctgcccgtg tggtggatga    480
acgggagcag atggccatca gtggtggctt catccgcagg gtaacaaatg atgcccggga    540
aaatgagatg gatgagaacc tggagcaggt gagcggcatc atcggaaacc tccgccatat    600
ggctctagac atgggcaatg agattgacac ccagaatcgc cagatcgaca ggatcatgga    660
gaaggctgat tccaacaaaa ccagaattga tgaagccaac caacgtgcaa caaagatgct    720
gggaagtggt taagaattcg agctcggcgc gcctgcaggt cgacaagctt gcggccgcat    780
aatgcttaag tcgaacagaa agtaatcgta ttgtacacgg ccgcataatc gaaattaata    840
cgactcacta tagggaatt gtgagcggat aacaattccc catcttagta tattagttaa    900
gtataagaag gagatataca tatggcagat ctcaattgga tatcggccgg ccacgcgatc    960
gctgacgtcg gtaccctcga gtctggtaaa gaaaccgctg ctgcgaaatt tgaacgccag   1020
cacatggact cgtctactag cgcagcttaa ttaacctagg ctgctgccac cgctgagcaa   1080
taactagcat aacccttgg  ggcctctaaa cgggtcttga ggggtttttt gctgaaacct   1140
caggcatttg agaagcacac ggtcacactg cttccggtag tcaataaacc ggtaaaccag   1200
caatagacat aagcggctat ttaacgaccc tgccctgaac cgacgacaag ctgacgaccg   1260
ggtctccgca agtggcactt tccggggaaa tgtgcgcgga acccctattt gtttattttt   1320
ctaaatacat tcaaatatgt atccgctcat gaattaattc ttagaaaaac tcatcgagca   1380
tcaaatgaaa ctgcaattta ttcatatcag gattatcaat accatatttt tgaaaaagcc   1440
gtttctgtaa tgaaggagaa aactcaccga ggcagttcca taggatggca agatcctggt   1500
atcggtctgc gattccgact cgtccaacat caatacaacc tattaatttc ccctcgtcaa   1560
aaataaggtt atcaagtgag aaatcaccat gagtgacgac tgaatccggt gagaatggca   1620
aaagtttatg catttctttc cagacttgtt caacaggcca gccattacgc tcgtcatcaa   1680
aatcactcgc atcaaccaaa ccgttattca ttcgtgattg cgcctgagcg agacgaaata   1740
cgcggtcgct gttaaaagga caattacaaa caggaatcga atgcaaccgg cgcaggaaca   1800
ctgccagcgc atcaacaata ttttcacctg aatcaggata ttcttctaat acctggaatg   1860
ctgtttttcc ggggatcgca gtggtgagta accatgcatc atcaggagta cggataaaat   1920
gcttgatggt cggaagaggc ataaattccg tcagccagtt tagtctgacc atctcatctg   1980
taacatcatt ggcaacgcta cctttgccat gtttcagaaa caactctggc gcatcgggct   2040
tcccatacaa tcgatagatt gtcgcacctg attgcccgac attatcgcga gcccatttat   2100
acccatataa atcagcatcc atgttggaat ttaatcgcgg cctagagcaa gacgtttccc   2160
gttgaatatg gctcatactc ttcctttttc aatattattg aagcatttat cagggttatt   2220
gtctcatgag cggatacata tttgaatgta tttagaaaaa taaacaaata ggcatgctag   2280
cgcagaaacg tcctagaaga tgccaggagg atacttagca gagagacaat aaggccggag   2340
cgaagccgtt tttccatagg ctccgccccc ctgacgaaca tcacgaaatc tgacgctcaa   2400
atcagtggtg gcgaaacccg acaggactat aaagatacca ggcgtttccc cctgatggct   2460
ccctcttgcg ctctcctgtt cccgtcctgc ggcgtccgtg ttgtggtgga ggctttaccc   2520
aaatcaccac gtcccgttcc gtgtagacag ttcgctccaa gctgggctgt gtgcaagaac   2580
cccccgttca gcccgactgc tgcgccttat ccggtaacta tcatcttgag tccaacccgg   2640
aaagacacga caaaacgcca ctggcagcag ccattggtaa ctgagaatta gtggatttag   2700
```

```
atatcgagag tcttgaagtg gtggcctaac agaggctaca ctgaaaggac agtatttggt    2760
atctgcgctc cactaaagcc agttaccagg ttaagcagtt ccccaactga cttaaccttc    2820
gatcaaaccg cctccccagg cggttttttc gtttacagag caggagatta cgacgatcgt    2880
aaaaggatct caagaagatc ctttacggat tcccgacacc atcactctag atttcagtgc    2940
aatttatctc ttcaaatgta gcacctgaag tcagccccat acgatataag ttgtaattct    3000
catgttagtc atgccccgcg cccaccggaa ggagctgact gggttgaagg ctctcaaggg    3060
catcggtcga gatcccggtg cctaatgagt gagctaactt acattaattg cgttgcgctc    3120
actgcccgct ttccagtcgg gaaacctgtc gtgccagctg cattaatgaa tcggccaacg    3180
cgcggggaga ggcggtttgc gtattgggcg ccagggtggt ttttcttttc accagtgaga    3240
cgggcaacag ctgattgccc ttcaccgcct ggccctgaga gagttgcagc aagcggtcca    3300
cgctggtttg ccccagcagg cgaaaatcct gtttgatggt ggttaacggc gggatataac    3360
atgagctgtc ttcggtatcg tcgtatccca ctaccgagat gtccgcacca acgcgcagcc    3420
cggactcggt aatggcgcgc attgcgccca gcgccatctg atcgttggca accagcatcg    3480
cagtgggaac gatgccctca ttcagcattt gcatggtttg ttgaaaaccg gacatggcac    3540
tccagtcgcc ttcccgttcc gctatcggct gaatttgatt gcgagtgaga tatttatgcc    3600
agccagccag acgcagacgc gccgagacag aacttaatgg gcccgctaac agcgcgattt    3660
gctggtgacc caatgcgacc agatgctcca cgcccagtcg cgtaccgtct tcatgggaga    3720
aaataatact gttgatgggt gtctggtcag agacatcaag aaataacgcc ggaacattag    3780
tgcaggcagc ttcacagca atggcatcct ggtcatccag cggatagtta atgatcagcc    3840
cactgacgcg ttgcgcgaga agattgtgca ccgccgcttt acaggcttcg acgccgcttc    3900
gttctaccat cgacaccacc acgctggcac ccagttgatc ggcgcgagat ttaatcgccg    3960
cgacaatttg cgacggcgcg tgcagggcca gactggaggt ggcaacgcca atcagcaacg    4020
actgtttgcc cgccagttgt tgtgccacgc ggttgggaat gtaattcagc tccgccatcg    4080
ccgcttccac ttttccccgc gttttcgcag aaacgtggct ggcctggttc accacgcggg    4140
aaacggtctg ataagagaca ccggcatact ctgcgacatc gtataacgtt actggtttca    4200
cattcaccac cctgaattga ctctcttccg ggcgctatca tgccataccg cgaaaggttt    4260
tgcgccattc gatggtgtcc gggatctcga cgctctccct tatgcgactc ctgcattagg    4320
aaattaatac gactcactat a                                             4341
```

<210> SEQ ID NO 5
<211> LENGTH: 6076
<212> TYPE: DNA
<213> ORGANISM: Artificial Sequence
<220> FEATURE:
<223> OTHER INFORMATION: pET28b His-CfaC-eGFP-RGD

<400> SEQUENCE: 5

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
```

```
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta       540
tccgctcatg aattaattct tagaaaaact catcgagcat caaatgaaac tgcaatttat      600
tcatatcagg attatcaata ccatatttt gaaaaagccg tttctgtaat gaaggagaaa       660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa agtttatgc atttcttcc       840 agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200 cttttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500 gatcctttt ttctgcgcgt aatctgctgc ttgcaaacaa aaaaccacc gctaccagcg      1560 gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920 aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280 tatttttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
```

```
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccgaaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagcg ctgccggca cctgtcctac     3360 gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg tgtccggga     4680 tctcgacgct ctcccttatg cgactcctgc attaggaagc agcccagtag taggttgagg    4740
ccgttgagca ccgccgccgc aaggaatggt gcatgcaagg agatggcgcc aacagtccc     4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca gccatcatca tcatcatcac    5100
```

| | |
|---|---|
| gtcaagatca ttagtcgtaa gagtctgggc actcaaaacg tctacgatat tggagtagaa | 5160 |
| aaagatcata atttttttgct gaagaatggg ctggtggcct ctaactgctt caacgtgagc | 5220 |
| aagggcgagg agctgttcac cggggtggtg cccatcctgg tcgagctgga cggcgacgta | 5280 |
| aacgccaca agttcagcgt gtccggcgag ggcgagggcg atgccaccta cggcaagctg | 5340 |
| accctgaagt tcatctgcac caccggcaag ctgcccgtgc cctggcccac cctcgtgacc | 5400 |
| accctgacct acggcgtgca gtgcttcagc cgctaccccg accacatgaa gcagcacgac | 5460 |
| ttcttcaagt ccgccatgcc cgaaggctac gtccaggagc gcaccatctt cttcaaggac | 5520 |
| gacggcaact acaagacccg cgccgaggtg aagttcgagg gcgacaccct ggtgaaccgc | 5580 |
| atcgagctga agggcatcga cttcaaggag gacggcaaca tcctggggca agctggag | 5640 |
| tacaactaca acagccacaa cgtctatatc atggccgaca gcagaagaa cggcatcaag | 5700 |
| gtgaacttca agatccgcca caacatcgag gacggcagcg tgcagctcgc cgaccactac | 5760 |
| cagcagaaca ccccccatcgg cgacggcccc gtgctgctgc ccgacaacca ctacctgagc | 5820 |
| acccagtccg ccctgagcaa agaccccaac gagaagcgcg atcacatggt cctgctggag | 5880 |
| ttcgtgaccg ccgccgggat cactctcggc atggacgagc tgtacaagag aggtgattga | 5940 |
| gatccggctg ctaacaaagc ccgaaaggaa gctgagttgg ctgctgccac cgctgagcaa | 6000 |
| taactagcat aaccccttgg ggcctctaaa cgggtcttga ggggttttt gctgaaagga | 6060 |
| ggaactatat ccggat | 6076 |

<210> SEQ ID NO 6
<211> LENGTH: 6631
<212> TYPE: DNA
<213> ORGANISM: Artificial Sequence
<220> FEATURE:
<223> OTHER INFORMATION: pET28b His-CfaC-HC

<400> SEQUENCE: 6

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta taagggattt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta cggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa agtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |

```
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccggttg gactcaagac gatagttacc ggataaggcg    1800
cagcggtcgg gctgaacggg gggttcgtgc acacagccca gcttggagcg aacgacctac    1860
accgaactga atacctaca gcgtgagcta tgagaaagcg ccacgcttcc gaagggaga    1920 aaggcggaca ggtatccggt aagcggcagg gtcggaacag gagagcgcac gagggagctt    1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
```

```
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc gcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca gccatcatca tcatcatcac    5100
gtcaagatca ttagtcgtaa gagtctgggc actcaaaacg tctacgatat tggagtagaa    5160
aaagatcata atttttgct gaagaatggg ctggtggcct ctaactgctt caacatgatt    5220
gtgaacacca gcattctgag catcgtgtac aaaaaagatg atctgattga tctgagccgc    5280
tatggtgcca aaatcaatat tggtgatcgc gtgtattatg atagcatcga caaaaaccag    5340
atcaaactga ttaatctgga aagcagcacc attgaggtga ttctgaaaaa tgccattgtg    5400
tataacagca tgtacgagaa tttttcgacc agcttctgga ttaaaatccc caaatacttc    5460
agcaaaatca acctgaacaa cgagtacacc attatcaact gcattgaaaa caatagcggt    5520
tggaaagtga gcctgaatta tggtgaaatt atctggaccc tgcaggacaa caaacagaat    5580
attcagcgtg tggtgttcaa atatagccag atggtgaata tcagcgatta cattaaccgc    5640 tggattttg tgaccattac caataatcgt ctgaccaaga gcaagatcta tattaacggt    5700
cgtctgattg accagaaacc gattagcaat ctgggtaata ttcatgccag caacaagatc    5760
atgtttaaac tggatggttg tcgtgatccg cgtcgctata ttatgatcaa atactttaac    5820
```

| | |
|---|---:|
| ctgtttgaca aagaactgaa cgaaaaagaa atcaaagacc tgtatgatag ccagagcaat | 5880 |
| agcggcattc tgaaagattt ttggggtaac tatctgcagt atgacaaacc gtattatatg | 5940 |
| ctgaacctgt tcgatccgaa caaatatgtg gatgtgaaca atattggcat ccgtggctat | 6000 |
| atgtatctga aggtccgcg tggtagcgtt gttaccacca acatttatct gaatagcacc | 6060 |
| ctgtatgaag gcaccaaatt catcattaaa aagtatgcca gcggcaacga agataatatt | 6120 |
| gtgcgtaata atgaccgcgt gtatatcaat gttgtggtga agaataaaga atatcgcctg | 6180 |
| gcaaccaatg caagccaggc aggcgttgaa aaaattctga gcgcactgga aattccggat | 6240 |
| gttggtaatc tgagccaggt tgttgttatg aaaagcaaag atgaccaggg cattcgcaac | 6300 |
| aaatgcaaaa tgaatctgca ggataataac ggcaacgata ttggctttat cggcttccat | 6360 |
| ctgtatgaca atattgcaaa actggttgcg agcaattggt ataatcgtca ggttggtaaa | 6420 |
| gcaagccgta cctttggttg tagctgggaa tttattccgg ttgatgatgg ttggggtgaa | 6480 |
| agcagcctgt aatgagatcc ggctgctaac aaagcccgaa aggaagctga gttggctgct | 6540 |
| gccaccgctg agcaataact agcataaccc cttggggcct ctaaacgggt cttgaggggt | 6600 |
| tttttgctga aggaggaac tatatccgga t | 6631 |

<210> SEQ ID NO 7
<211> LENGTH: 6583
<212> TYPE: DNA
<213> ORGANISM: Artificial Sequence
<220> FEATURE:
<223> OTHER INFORMATION: pET28b His-TEV-LC

<400> SEQUENCE: 7

| | |
|---|---:|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta taagggattt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa agtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| tttcacctga tcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |

```
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt cctgcgtta    2160 tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag tcgcagacg ttttgcagca    3060 gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
```

-continued

```
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg cgcgcattg    3840 cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccacttttt tcccgcgttt   4500 tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgcaccacc accaccacca cgagaatttg   5100
tattttcagg gtccgtttgt gaacaaacag ttcaactata agatccggt gaacggtgtt   5160 gatatcgcct atatcaaaat tccgaatgca ggtcagatgc agccggttaa agcctttaaa   5220
atccataaca aaatttgggt gattccggaa cgtgatacct ttaccaatcc ggaagaaggt   5280
gatctgaatc cgcctccgga agcaaaaacag gttccggtta gctattatga tagcacctat   5340
ctgagcaccg ataacgagaa agataactat ctgaaaggtg tgaccaaact gtttgaacgc   5400
atttatagta ccgatctggg tcgtatgctg ctgaccagca ttgttcgtgg tattccgttt   5460
tggggtggta gcaccattga taccgaactg aaagttattg acaccaactg cattaatgtg   5520
attcagccgg atggtagcta tcgtagcgaa gaactgaatc tggttattat ggtccgagc    5580 gcagatatca ttcagtttga atgtaaaagc tttggccacg atgttctgaa tctgacccgt   5640
aatggttatg gtagtaccca gtatattcgt ttcagtccgg attttacctt tggctttgaa   5700
gaaagcctgg aagttgatac aaatccgctg ttaggtcagg taaatttgc aaccgatccg   5760 gcagttaccc tggcacatga actgattcat gccgaacatc gtctgtatgg tattgccatt   5820
aatccgaatc gtgtgttcaa agtgaatacc aacgcctatt atgaaatgag cggtctggaa   5880
gtgagttttg aagaactgcg taccttttggt ggtcatgatg ccaaatttat cgatagcctg   5940
```

| | |
|---|---|
| caagaaaatg aatttcgcct gtactactat aacaaattca agatgttgc gagcaccctg | 6000 |
| aataaagcca aaagcattat tggcaccacc gcaagcctgc agtatatgaa aaatgtgttt | 6060 |
| aaagaaaaat atctgctgag cgaagatacc agcggtaaat ttagcgttga caaactgaaa | 6120 |
| ttcgataaac tgtacaagat gctgaccgag atttataccg aagataactt cgtgaacttc | 6180 |
| tttaaggtga tcaaccgcaa aacctacctg aactttgata agccgtgtt tcgcattaac | 6240 |
| attgtgccgg atgaaaacta caccatcaaa gatggcttta atctgaaggg tgcaaatctg | 6300 |
| tccaccaatt ttaacggtca gaacaccgaa attaacagcc gtaattttac ccgtctgaaa | 6360 |
| aactttaccg gtctgttcga attttacaaa ctgctgtgtg ttcgtggcat tatcccgttt | 6420 |
| aaatgacacc accaccacca ccactgagat ccggctgcta caaagcccg aaggaagct | 6480 |
| gagttggctg ctgccaccgc tgagcaataa ctagcataac cccttgggc ctctaaacgg | 6540 |
| gtcttgaggg gttttttgct gaaaggagga actatatccg gat | 6583 |

<210> SEQ ID NO 8
<211> LENGTH: 6583
<212> TYPE: DNA
<213> ORGANISM: Artificial Sequence
<220> FEATURE:
<223> OTHER INFORMATION: pET28b Hn-CfaN-his6

<400> SEQUENCE: 8

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcggggc tcccttaggg | 180 |
| gttccgattt agtgctttac ggcacctcga ccccaaaaa cttgattagg gtgatggttc | 240 |
| acgtagtggg ccatcgccct gatagacggt ttttcgccct tgacgttgg agtccacgtt | 300 |
| ctttaatagt ggactcttgt tccaaactgg aacaacactc aaccctatct cggtctattc | 360 |
| ttttgattta taggggattt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa ccccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa agttatgc atttctttcc | 840 |
| agacttgttc aacaggccag ccattacgct cgtcatcaaa atcactcgca tcaaccaaac | 900 |
| cgttattcat tcgtgattgc gcctgagcga gacgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgtttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccattata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa atcccttaa | 1440 |

```
cgtgagtttt cgttccactg agcgtcagac cccgtagaaa agatcaaagg atcttcttga    1500 gatcctttt  ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa  acgcctggta tctttatagt cctgtcgggt ttcgccacct ctgacttgag    2040
cgtcgatttt tgtgatgctc gtcaggggg  cggagcctat ggaaaaacgc cagcaacgcg    2100 gccttttac  ggtcctggc  cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
```

```
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccacttt tcccgcgttt    4500 tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgcaccacc accaccacca cgagaatttg    5100
tattttcagg gtccgtttgt gaacaaacag ttcaactata aagatccggt gaacggtgtt    5160
gatatcgcct atatcaaaat tccgaatgca ggtcagatgc agccggttaa agcctttaaa    5220
atccataaca aaatttgggt gattccggaa cgtgatacct ttaccaatcc ggaagaaggt    5280
gatctgaatc cgcctccgga agcaaaacag gttccggtta gctattatga tagcacctat    5340
ctgagcaccg ataacgagaa agataactat ctgaaaggtg tgaccaaact gtttgaacgc    5400
atttatagta ccgatctggg tcgtatgctg ctgaccagca ttgttcgtgg tattccgttt    5460
tggggtggta gcaccattga taccgaactg aaagttattg acaccaactg cattaatgtg    5520
attcagccgg atggtagcta tcgtagcgaa gaactgaatc tggttattat tggtccgagc    5580
gcagatatca ttcagtttga atgtaaaagc tttggccacg atgttctgaa tctgacccgt    5640
aatggttatg gtagtaccca gtatattcgt ttcagtccgg attttacctt tggctttgaa    5700
gaaagcctgg aagttgatac aaatccgctg ttaggtgcag gtaaatttgc aaccgatccg    5760
gcagttaccc tggcacatga actgattcat gccgaacatc gtctgtatgg tattgccatt    5820
aatccgaatc gtgtgttcaa agtgaatacc aacgcctatt atgaaatgag cggtctggaa    5880
gtgagttttg aagaactgcg tacccttggt ggtcatgatg ccaaatttat cgatagcctg    5940
caagaaaatg aatttcgcct gtactactat aacaaattca agatgttgc gagcaccctg    6000 aataaagcca aaagcattat tggcaccacc gcaagcctgc agtatatgaa aaatgtgttt    6060
aaagaaaaat atctgctgag cgaagatacc agcggtaaat ttagcgttga caaactgaaa    6120
ttcgataaac tgtacaagat gctgaccgag atttataccg aagataactt cgtgaacttc    6180
```

```
tttaaggtga tcaaccgcaa aacctacctg aactttgata aagccgtgtt tcgcattaac   6240
attgtgccgg atgaaaacta caccatcaaa gatggcttta atctgaaggg tgcaaatctg   6300
tccaccaatt ttaacggtca gaacaccgaa attaacagcc gtaattttac ccgtctgaaa   6360
aactttaccg gtctgttcga attttacaaa ctgctgtgtg ttcgtggcat tatcccgttt   6420
aaatgacacc accaccacca ccactgagat ccggctgcta caaagcccg aaaggaagct   6480 gagttggctg ctgccaccgc tgagcaataa ctagcataac cccttggggc ctctaaacgg   6540
gtcttgaggg gttttttgct gaaaggagga actatatccg gat                    6583
```

<210> SEQ ID NO 9
<211> LENGTH: 8146
<212> TYPE: DNA
<213> ORGANISM: Artificial Sequence
<220> FEATURE:
<223> OTHER INFORMATION: pET28b LCHn-CfaN-his

<400> SEQUENCE: 9

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aacctatct cggtctattc     360 ttttgattta agggattt tgccgatttc ggcctattgg ttaaaaaatg agctgattta     420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac      960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa    1440 cgtgagtttt cgttccactg agcgtcagac cccgtagaaa agatcaaagg atcttcttga   1500 gatcctttt tttctgcgcgt aatctgctgc ttgcaaacaa aaaaaccacc gctaccagcg   1560
gtggtttgtt tgccggatca agagctacca actctttttc cgaaggtaac tggcttcagc   1620
```

-continued

```
agagcgcaga taccaaatac tgtccttcta gtgtagccgt agttaggcca ccacttcaag      1680
aactctgtag caccgcctac atacctcgct ctgctaatcc tgttaccagt ggctgctgcc      1740
agtggcgata agtcgtgtct taccgggttg gactcaagac gatagttacc ggataaggcg      1800
cagcggtcgg gctgaacggg gggttcgtgc acacagccca gcttggagcg aacgacctac      1860
accgaactga gatacctaca gcgtgagcta tgagaaagcg ccacgcttcc cgaagggaga      1920
aaggcggaca ggtatccggt aagcggcagg gtcggaacag gagagcgcac gagggagctt      1980 ccaggggaa acgcctggta tctttatagt cctgtcgggt ttcgccacct ctgacttgag       2040
cgtcgatttt tgtgatgctc gtcagggggg cggagcctat ggaaaaacgc cagcaacgcg      2100
gcctttttac ggttcctggc cttttgctgg ccttttgctc acatgttctt tcctgcgtta      2160
tcccctgatt ctgtggataa ccgtattacc gcctttgagt gagctgatac cgctcgccgc      2220
agccgaacga ccgagcgcag cgagtcagtg agcgaggaag cggaagagcg cctgatgcgg      2280
tattttctcc ttacgcatct gtgcggtatt tcacaccgca tatatggtgc actctcagta      2340
caatctgctc tgatgccgca tagttaagcc agtatacact ccgctatcgc tacgtgactg      2400
ggtcatggct gcgccccgac acccgccaac acccgctgac gcgccctgac gggcttgtct      2460
gctcccggca tccgcttaca gacaagctgt gaccgtctcc gggagctgca tgtgtcagag      2520
gttttcaccg tcatcaccga aacgcgcgag gcagctgcgg taaagctcat cagcgtggtc      2580
gtgaagcgat tcacagatgt ctgcctgttc atccgcgtcc agctcgttga gtttctccag      2640
aagcgttaat gtctggcttc tgataaagcg ggccatgtta agggcggttt ttcctgtttt      2700
ggtcactgat gcctccgtgt aagggggatt tctgttcatg ggggtaatga taccgatgaa      2760
acgagagagg atgctcacga tacgggttac tgatgatgaa catgcccggt tactggaacg      2820
ttgtgagggt aaacaactgg cggtatggat gcggcgggac cagagaaaaa tcactcaggg      2880
tcaatgccag cgcttcgtta atacagatgt aggtgttcca cagggtagcc agcagcatcc      2940
tgcgatgcag atccggaaca taatggtgca gggcgctgac ttccgcgttt ccagacttta      3000
cgaaacacgg aaaccgaaga ccattcatgt tgttgctcag gtcgcagacg ttttgcagca      3060
gcagtcgctt cacgttcgct cgcgtatcgg tgattcattc tgctaaccag taaggcaacc      3120
ccgccagcct agccgggtcc tcaacgacag gagcacgatc atgcgcaccc gtggggccgc      3180
catgccggcg ataatggcct gcttctcgcc gaaacgtttg gtggcgggac cagtgacgaa      3240
ggcttgagcg agggcgtgca agattccgaa taccgcaagc gacaggccga tcatcgtcgc      3300
gctccagcga aagcggtcct cgccgaaaat gacccagagc gctgccggca cctgtcctac      3360
gagttgcatg ataaagaaga cagtcataag tgcggcgacg atagtcatgc cccgcgccca      3420
ccggaaggag ctgactgggt tgaaggctct caagggcatc ggtcgagatc ccggtgccta      3480
atgagtgagc taacttacat taattgcgtt gcgctcactg cccgctttcc agtcgggaaa      3540
cctgtcgtgc cagctgcatt aatgaatcgg ccaacgcgcg gggagaggcg gtttgcgtat      3600
tgggcgccag ggtggttttt cttttcacca gtgagacggg caacagctga ttgcccttca      3660
ccgcctggcc ctgagagagt tgcagcaagc ggtccacgct ggtttgcccc agcaggcgaa      3720
aatcctgttt gatggtggtt aacggcggga tataacatga gctgtcttcg gtatcgtcgt      3780
atcccactac cgagatatcc gcaccaacgc gcagcccgga ctcggtaatg gcgcgcattg      3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccagacgc agacgcgccg      4020
```

```
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgccgtttg tgaacaaaca gttcaactat    5100
aaagatccgg tgaacggtgt tgatatcgcc tatatcaaaa ttccgaatgc aggtcagatg    5160
cagccggtta aagcctttaa aatccataac aaaatttggg tgattccgga acgtgatacc    5220
tttaccaatc cggaagaagg tgatctgaat ccgcctccgg aagcaaaaca ggttccggtt    5280
agctattatg atagcaccta tctgagcacc gataacgaga aagataacta tctgaaaggt    5340
gtgaccaaac tgtttgaacg catttatagt accgatctgg gtcgtatgct gctgaccagc    5400
attgttcgtg gtattccgtt ttggggtggt agcaccattg ataccgaact gaaagttatt    5460
gacaccaact gcattaatgt gattcagccg gatggtagct atcgtagcga agaactgaat    5520
ctggttatta ttggtccgag cgcagatatc attcagtttg aatgtaaaag ctttggccac    5580
gatgttctga atctgacccg taatggttat ggtagtaccc agtatattcg tttcagtccg    5640
gattttacct ttggctttga agaaagcctg gaagttgata caaatccgct gttaggtgca    5700
ggtaaatttg caaccgatcc ggcagttacc ctggcacatg aactgattca tgccgaacat    5760
cgtctgtatg gtattgccat taatccgaat cgtgtgttca agtgaatac caacgcctat    5820 tatgaaatga gcggtctgga agtgagtttt gaagaactgc gtacctttgg tggtcatgat    5880
gccaaattta tcgatagcct gcaagaaaat gaatttcgcc tgtactacta aacaaattc    5940 aaagatgttg cgagcaccct gaataaagcc aaaagcatta ttggcaccac cgcaagcctg    6000
cagtatatga aaaatgtgtt taagaaaaa tatctgctga gcgaagatac cagcggtaaa    6060
tttagcgttg acaaactgaa attcgataaa ctgtacaaga tgctgaccga gatttatacc    6120
gaagataact tcgtgaactt cttttaaggtg atcaaccgca aacctacct gaactttgat    6180 aaagccgtgt ttcgcattaa cattgtgccg gatgaaaact acaccatcaa agatggcttt    6240
aatctgaagg gtgcaaatct gtccaccaat tttaacggtc agaacaccga attaacagc    6300 cgtaattta cccgtctgaa aaactttacc ggtctgttcg aattttacaa actgctgtgt    6360
```

```
gttcgtggca ttatcccgtt taaaaccaaa agtctggatg agggttataa caaagcactg   6420
aatgatctgt gcatcaaagt gaataattgg gacctgtttt ttagcccgag cgaagataac   6480
tttaccaacg atctggataa agtggaagaa attaccgcag ataccaatat tgaagcagcc   6540
gaagaaaaca ttagcctgga tctgattcag cagtattatc tgaccttcga ttttgataac   6600
gagccggaaa atatcagcat tgaaaatctg agcagcgata ttattggtca gctggaaccg   6660
atgccgaata ttgaacgttt tccgaatggc aaaaaatacg agctggacaa atataccatg   6720
ttccattatc tgcgtgccca agaatttgaa catggtgata gccgcattat tctgaccaat   6780
tcagcagaag aagcactgct gaaaccgaat gttgcatata ccttttttcag cagcaaatat   6840 gtgaaaaaaa tcaacaaagc cgtcgaagcc tttatgtttc tgaattgggc tgaagaactg   6900
gtgtatgatt tcaccgatga aaccaatgaa gttaccacca tggataaaat tgccgacatt   6960
accattatcg tgccgtatat tggtccggct ctgaatattg caatatgct gagcaaaggt   7020 gaatttgtgg aagccattat ctttaccggt gttgttgcaa tgctggaatt tatcccggaa   7080
tatgcactgc cggttttttgg cacctttgca attgttagct atatcgccaa taaagttctg   7140
accgttcaga ccattaataa cgcactgagc aaacgcaatg agaaatggga tgaagtgtat   7200
aaatacaccg ttaccaattg gctggccaaa gttaatacc agattgatct gatccgcgag   7260
aaaatgaaaa aagccctgga aaatcaggca gaagcaacca agcaattat caactatcag   7320 tacaaccagt acaccgagga agagaaaaac aacatcaact tcaacatcga tgacctgagc   7380
agcaaactga tgaaagcat taatagcgcc atgattaaca tcaacaagtt tctggatcag   7440
tgcagcgtta gctatctgat gaatagcatg attccgtatg cagtgaaacg cctgaaagat   7500
tttgatgcaa gcgttcgtga tgtcctgctg aaatatatct atgataatcg tggcaccctg   7560
gttctgcagg ttgatcgtct gaaagatgaa gttaataaca ccctgagcgc agatattccg   7620
tttcagctga gtaaatatgt ggacaacaaa aaactgctga gcacctttac cgagtacatc   7680
aaaaactgcc tgtcttacga cacagagatt ctgaccgttg aatatggatt ccttcctatc   7740
ggtaagatcg tggaggaacg gattgaatgc acagtctata cggtagataa aaatggcttt   7800
gtgtatacac aacctattgc tcagtggcat aaccggggag aacaggaagt tttcgaatac   7860
tgcttagaag acggttcgat tatccgtgca acgaaagatc acaaatttat gacgaccgac   7920
ggtcagatgt taccgattga tgagttttc gaacggggt tagacctgaa acaagttgat   7980
ggtttgccgc accaccacca ccaccactga gatccggctg ctaacaaagc ccgaaggaa   8040 gctgagttgg ctgctgccac cgctgagcaa taactagcat aaccccttgg ggcctctaaa   8100
cgggtcttga ggggttttttt gctgaaagga ggaactatat ccggat              8146
```

<210> SEQ ID NO 10
<211> LENGTH: 8137
<212> TYPE: DNA
<213> ORGANISM: Artificial Sequence
<220> FEATURE:
<223> OTHER INFORMATION: pET28b LCstarHn-CfaN-his

<400> SEQUENCE: 10

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcggggc tccctttagg   180 gttccgattt agtgctttac ggcacctcga ccccaaaaaa cttgattagg gtgatggttc   240
acgtagtggg ccatcgccct gatagacggt ttttcgccct ttgacgttgg agtccacgtt   300
```

```
ctttaatagt ggactcttgt tccaaactgg aacaacactc aaccctatct cggtctattc    360
ttttgattta aagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca dacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
```

```
aagcgttaat gtctggcttc tgataaagcg ggccatgtta agggcggttt tttcctgttt    2700
ggtcactgat gcctccgtgt aaggggggatt tctgttcatg ggggtaatga taccgatgaa   2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgcggccac gatgcgtccg gcgtagagga tcgagatctc gatcccgcga    4980
aattaatacg actcactata ggggaattgt gagcggataa caattcccct ctagaaataa    5040
```

-continued

```
ttttgtttaa ctttaagaag gagatatacc atgccgtttg tgaacaaaca gttcaactat    5100
aaagatccgg tgaacggtgt tgatatcgcc tatatcaaaa ttccgaatgc aggtcagatg    5160
cagccggtta aagcctttaa aatccataac aaaatttggg tgattccgga acgtgatacc    5220
tttaccaatc cggaagaagg tgatctgaat ccgcctccgg aagcaaaaca ggttccggtt    5280
agctattatg atagcaccta tctgagcacc gataacgaga agataacta tctgaaaggt    5340 gtgaccaaac tgtttgaacg catttatagt accgatctgg tcgtatgct gctgaccagc    5400 attgttcgtg gtattccgtt ttggggtggt agcaccattg ataccgaact gaaagttatt    5460
gacaccaact gcattaatgt gattcagccg atggtagct atcgtagcga agaactgaat    5520
ctggttatta ttggtccgag cgcagatatc attcagtttg aatgtaaaag ctttggccac    5580
gatgttctga atctgacccg taatggttat ggtagtaccc agtatattcg tttcagtccg    5640
gattttacct ttggctttga agaaagcctg gaagttgata caaatccgct gttaggtgca    5700
ggtaaatttg caaccgatcc ggcagttacc ctggcacatg aactgattca tgccgaacat    5760
cgtctgtatg gtattgccat taatccgaat cgtgtgttca agtgaatac caacgcctat    5820 tatgaaatga cggtctgga agtgagtttt gaagaactgc gtaccttttgg tggtcatgat    5880 gccaaattta tcgatagcct gcaagaaaat gaatttcgcc tgtactacta taacaaattc    5940
aaagatgttg cgagcaccct gaataaagcc aaaagcatta ttggcaccac cgcaagcctg    6000
cagtatatga aaaatgtgtt taagaaaaaa tatctgctga gcgaagatac cagcggtaaa    6060
tttagcgttg acaaactgaa attcgataaa ctgtacaaga tgctgaccga gatttatacc    6120
gaagataact tcgtgaactt ctttaaggtg atcaacgcga aaacctttct gaactttgat    6180
aaagccgtgt ttcgcattaa cattgtgccg gatgaaaact acaccatcaa agatggcttt    6240
aatctgaagg gtgcaaatct gtccaccaat tttaacggtc agaacaccga attaacagc    6300 cgtaattttta cccgtctgaa aaactttacc ggtctgttcg aattttacaa actgctgtgt    6360
gttcgtggca ttatcccgtt taaagagaac ctgtatttttc agggtgcact gaatgatctg    6420
tgcatcaaag tgaataattg ggaccctgttt tttagcccga gcgaagataa ctttaccaac    6480
gatctggata aagtggaaga aattaccgca gataccaata ttgaagcagc cgaagaaaac    6540
attagcctgg atctgattca gcagtattat ctgaccttcg attttgataa cgagccggaa    6600
aatatcagca ttgaaaatct gagcagcgat attattggtc agctggaacc gatgccgaat    6660
attgaacgtt ttccgaatgg caaaaaaatac gagctggaca aatataccat gttccattat    6720
ctgcgtgccc aagaatttga acatggtgat agccgcatta ttctgaccaa ttcagcagaa    6780
gaagcactgc tgaaaccgaa tgttgcatat acctttttca gcagcaaata tgtgaaaaaa    6840
atcaacaaag ccgtcgaagc ctttatgttt ctgaattggg ctgaagaact ggtgtatgat    6900
ttcaccgatg aaaccaatga agttaccacc atggataaaa ttgccgacat taccattatc    6960
gtgccgtata ttggtccggc tctgaatatt ggcaatatgc tgagcaaagg tgaatttgtg    7020
gaagccatta tctttaccgg tgttgttgca atgctggaat ttatcccgga atatgcactg    7080
ccggtttttg gcacctttgc aattgttagc tatatcgcca ataaagttct gaccgttcag    7140
accattaata acgcactgag caaacgcaat gagaaatggg atgaagtgta taatacacc    7200 gttaccaatt ggctggccaa agttaatacc cagattgatc tgatccgcga gaaaatgaaa    7260
aaagccctgg aaaatcaggc agaagcaacc aaagcaatta tcaactatca gtacaaccag    7320
tacaccgagg aagagaaaaa caacatcaac ttcaacatcg atgacctgag cagcaaactg    7380
```

| | |
|---|---:|
| aatgaaagca ttaatagcgc catgattaac atcaacaagt ttctggatca gtgcagcgtt | 7440 |
| agctatctga tgaatagcat gattccgtat gcagtgaaac gcctgaaaga ttttgatgca | 7500 |
| agcgttcgtg atgtcctgct gaaatatatc tatgataatc gtggcaccct ggttctgcag | 7560 |
| gttgatcgtc tgaaagatga agttaataac ccctgagcg cagatattcc gtttcagctg | 7620 |
| agtaaatatg tggacaacaa aaaactgctg agcacctta ccgagtacat caaaaactgc | 7680 |
| ctgtcttacg acacagagat tctgaccgtt gaatatggat tccttcctat cggtaagatc | 7740 |
| gtggaggaac ggattgaatg cacagtctat acggtagata aaaatggctt tgtgtataca | 7800 |
| caacctattg ctcagtggca taaccgggga gaacaggaag ttttcgaata ctgcttagaa | 7860 |
| gacggttcga ttatccgtgc aacgaaagat cacaaattta tgacgaccga cggtcagatg | 7920 |
| ttaccgattg atgagatttt cgaacggggg ttagacctga acaagttga tggttttgccg | 7980 |
| caccaccacc accaccactg agatccggct gctaacaaag cccgaaagga agctgagttg | 8040 |
| gctgctgcca ccgctgagca ataactagca taacccttg gggcctctaa acgggtcttg | 8100 |
| aggggttttt tgctgaaagg aggaactata tccggat | 8137 |

```
<210> SEQ ID NO 11
<211> LENGTH: 6238
<212> TYPE: DNA
<213> ORGANISM: Artificial Sequence
<220> FEATURE:
<223> OTHER INFORMATION: pET28b mCherry-CfaN-His

<400> SEQUENCE: 11
```

| | |
|---|---:|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tcccttagg | 180 |
| gttccgattt agtgctttac ggcacctcga ccccaaaaaa cttgattagg gtgatggttc | 240 |
| acgtagtggg ccatcgccct gatagacggt ttttcgccct tgacgttgg agtccacgtt | 300 |
| ctttaatagt ggactcttgt tccaaactgg aacaacactc aaccctatct cggtctattc | 360 |
| ttttgattta agggattt tgccgatttc ggcctattgg ttaaaaatg agctgattta | 420 |
| acaaaattt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg aattaattct tagaaaaact catcgagcat caaatgaaac tgcaatttat | 600 |
| tcatatcagg attatcaata ccatatttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| ttcacctga tcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |

```
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttcc gaaggtaac tggcttcagc    1620 agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga atacctaca gcgtgagcta tgagaaagcg ccacgcttcc gaagggaga    1920 aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100 gccttttac ggttcctggc cttttgctgg ccttttgctc acatgttctt tcctgcgtta    2160 tccctgatt ctgtggataa ccgtattacc gcctttgagt gagctgatac cgctcgccgc    2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagactta    3000 cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
```

```
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atggtgagca agggcgagga ggataacatg    5100
gccatcatca aggagttcat gcgcttcaag gtgcacatgg agggctccgt gaacggccac    5160
gagttcgaga tcgagggcga gggcgagggc cgcccctacg agggcaccca gaccgccaag    5220
ctgaaggtga ccaagggtgg ccccctgccc ttcgcctggg acatcctgtc ccctcagttc    5280
atgtacggct ccaaggccta cgtgaagcac cccgccgaca tccccgacta cttgaagctg    5340
tccttccccg agggcttcaa gtgggagcgc gtgatgaact tcgaggacgg cggcgtggtg    5400
accgtgaccc aggactcctc cctccaggac ggcgagttca tctacaaggt gaagctgcgc    5460
ggcaccaact tcccctccga cggccccgta atgcagaaga gaccatggg ctgggaggcc    5520 tcctccgagc ggatgtaccc cgaggacggc gccctgaagg gcgagatcaa gcagaggctg    5580
aagctgaagg acggcggcca ctacgacgct gaggtcaaga ccacctacaa ggccaagaag    5640
cccgtgcagc tgcccggcgc ctacaacgtc aacatcaagt tggacatcac ctcccacaac    5700
gaggactaca ccatcgtgga acagtacgaa cgcgccgagg ccgccactc caccggcggc    5760 atggacgagc tgtacaagtg cctgtcttac gacacagaga ttctgaccgt tgaatatgga    5820
ttccttccta tcggtaagat cgtggaggaa cggattgaat gcacagtcta tacggtagat    5880
aaaaatggct ttgtgtatac acaacctatt gctcagtggc ataaccgggg agaacaggaa    5940
gttttcgaat actgcttaga agacggttcg attatccgtg caacgaaaga tcacaaattt    6000
atgacgaccg acggtcagat gttaccgatt gatgagattt tcgaacgggg gttagacctg    6060
```

```
aaacaagttg atggtttgcc gcaccaccac caccaccact gagatccggc tgctaacaaa    6120
gcccgaaagg aagctgagtt ggctgctgcc accgctgagc aataactagc ataacccctt    6180
ggggcctcta acgggtctt gagggtttt ttgctgaaag gaggaactat atccggat        6238
```

<210> SEQ ID NO 12
<211> LENGTH: 6416
<212> TYPE: DNA
<213> ORGANISM: Artificial Sequence
<220> FEATURE:
<223> OTHER INFORMATION: pETduet LC-S-S-Hn-CfaN-His

<400> SEQUENCE: 12

```
ggggaattgt gagcggataa caattcccct gtagaaataa ttttgtttaa ctttaataag     60
gagatatacc atgccgtttg tgaacaaaca gttcaactat aaagatccgg tgaacggtgt    120
tgatatcgcc tatatcaaaa ttccgaatgc aggtcagatg cagccggtta aagcctttaa    180
aatccataac aaaatttggg tgattccgga acgtgatacc tttaccaatc cggaagaagg    240
tgatctgaat ccgcctccgg aagcaaaaca ggttccggtt agctattatg atagcaccta    300
tctgagcacc gataacgaga aagataacta tctgaaaggt gtgaccaaac tgtttgaacg    360
catttatagt accgatctgg gtcgtatgct gctgaccagc attgttcgtg gtattccgtt    420
ttggggtggt agcaccattg ataccgaact gaaagttatt gacaccaact gcattaatgt    480
gattcagccg gatggtagct atcgtagcga agaactgaat ctggttatta ttggtccgag    540
cgcagatatc attcagtttg aatgtaaaag ctttggccac gatgttctga atctgacccg    600
taatggttat ggtagtaccc agtatattcg tttcagtccg gattttacct ttggctttga    660
agaaagcctg gaagttgata caaatccgct gttaggtgca ggtaaatttg caaccgatcc    720
ggcagttacc ctggcacatg aactgattca tgccgaacat cgtctgtatg gtattgccat    780
taatccgaat cgtgtgttca agtgaatac caacgcctat tatgaaatga gcggtctgga    840
agtgagtttt gaagaactgc gtaccttgg tggtcatgat gccaaattta tcgatagcct    900
gcaagaaaat gaatttcgcc tgtactacta taacaaattc aaagatgttg cgagcaccct    960
gaataaagcc aaaagcatta ttggcaccac cgcaagcctg cagtatatga aaatgtgtt   1020
taaagaaaaa tatctgctga gcgaagatac cagcggtaaa tttagcgttg acaaactgaa   1080
attcgataaa ctgtacaaga tgctgaccga gatttatacc gaagataact tcgtgaactt   1140
ctttaaggtg atcaacgcga aaaccttttct gaactttgat aaagccgtgt tcgcattaa   1200
cattgtgccg gatgaaaact acaccatcaa agatggcttt aatctgaagg tgcaaatct   1260
gtccaccaat tttaacggtc agaacaccga attaacagc cgtaattta cccgtctgaa   1320
aaactttacc ggtctgttcg aattttacaa actgctgtgt gttcgtggca ttatcccgtt   1380
taaataatgc ttaagtcgaa cagaaagtaa tcgtattgta cacggccgca taatcgaaat   1440
taatacgact cactataggg gaattgtgag cggataacaa ttcccatct tagtatatta   1500
gttaagtata agaaggagat atacatatgg cactgaatga tctgtgcatc aaagtgaata   1560
attgggacct gtttttagc ccgagcgaag ataactttac caacgatctg gataaagtgg   1620
aagaaattac cgcagatacc aatattgaag cagccgaaga aacattagc ctggatctga   1680
ttcagcagta ttatctgacc ttcgattttg ataacgagcc ggaaatatc agcattgaaa   1740
atctgagcag cgatattatt ggtcagctgg aaccgatgcc gaatattgaa cgttttccga   1800
atggcaaaaa atacgagctg gacaaatata ccatgttcca ttatctgcgt gcccaagaat   1860
```

```
ttgaacatgg tgatagccgc attattctga ccaattcagc agaagaagca ctgctgaaac    1920
cgaatgttgc atataccttt ttcagcagca aatatgtgaa aaaaatcaac aaagccgtcg    1980
aagcctttat gtttctgaat tgggctgaag aactggtgta tgatttcacc gatgaaacca    2040
atgaagttac caccatggat aaaattgccg acattaccat tatcgtgccg tatattggtc    2100
cggctctgaa tattggcaat atgctgagca aggtgaatt tgtggaagcc attatcttta    2160
ccggtgttgt tgcaatgctg gaatttatcc cggaatatgc actgccggtt tttggcacct    2220
ttgcaattgt tagctatatc gccaataaag ttctgaccgt tcagaccatt aataacgcac    2280
tgagcaaacg caatgagaaa tgggatgaag tgtataaata caccgttacc aattggctgg    2340
ccaaagttaa tacccagatt gatctgatcc gcgagaaaat gaaaaagcc ctggaaaatc     2400 aggcagaagc aaccaaagca attatcaact atcagtacaa ccagtacacc gaggaagaga    2460
aaaacaacat caacttcaac atcgatgacc tgagcagcaa actgaatgaa agcattaata    2520
gcgccatgat taacatcaac aagtttctgg atcagtgcag cgttagctat ctgatgaata    2580
gcatgattcc gtatgcagtg aaacgcctga agattttga tgcaagcgtt cgtgatgtcc     2640
tgctgaaata tatctatgat aatcgtggca ccctggttct gcaggttgat cgtctgaaag    2700
atgaagttaa taacaccctg agcgcagata ttccgtttca gctgagtaaa tatgtggaca    2760
acaaaaaact gctgagcacc tttaccgagt acatcaaaaa ctgcctgtct tacgacacag    2820
agattctgac cgttgaatat ggattccttc ctatcggtaa gatcgtggag gaacggattg    2880
aatgcacagt ctatacggta gataaaaatg ctttgtgta tacacaacct attgctcagt     2940
ggcataaccg gggagaacag gaagttttcg aatactgctt agaagacggt tcgattatcc    3000
gtgcaacgaa agatcacaaa tttatgacga ccgacggtca gatgttaccg attgatgaga    3060
ttttcgaacg ggggttagac ctgaaacaag ttgatggttt gccgcaccac caccaccacc    3120
actaattaac ctaggctgct gccaccgctg agcaataact agcataaccc cttggggcct    3180
ctaaacgggt cttgaggggt ttttgctga acctcaggc atttgagaag cacacggtca     3240
cactgcttcc ggtagtcaat aaaccggtaa accagcaata gacataagcg ctatttaac     3300 gacccctgccc tgaaccgacg acaagctgac gaccgggtct ccgcaagtgg cacttttcgg    3360
ggaaatgtgc gcggaacccc tatttgttta ttttttctaaa tacattcaaa tatgtatccg    3420
ctcatgaatt aattcttaga aaaactcatc gagcatcaaa tgaaactgca atttattcat    3480
atcaggatta tcaataccat attttttgaaa aagccgtttc tgtaatgaag gagaaaactc    3540
accgaggcag ttccatagga tgcaagatc ctggtatcgg tctgcgattc cgactcgtcc     3600
aacatcaata caacctatta atttcccctc gtcaaaaata aggttatcaa gtgagaaatc    3660
accatgagtg acgactgaat ccggtgagaa tggcaaaagt ttatgcattt ctttccagac    3720
ttgttcaaca ggccagccat tacgctcgtc atcaaaatca ctcgcatcaa ccaaaccgtt    3780
attcattcgt gattgcgcct gagcgagacg aaatacgcgg tcgctgttaa aaggacaatt    3840
acaaacagga atcgaatgca accggcgcag gaacactgcc agcgcatcaa caatattttc    3900
acctgaatca ggatattctt ctaataccctg gaatgctgtt ttcccgggga tcgcagtggt    3960
gagtaaccat gcatcatcag gagtacggat aaaatgcttg atggtcggaa gaggcataaa    4020
ttccgtcagc cagtttagtc tgaccatctc atctgtaaca tcattggcaa cgctacctt    4080 gccatgtttc agaaacaact ctggcgcatc gggcttccca tacaatcgat agattgtcgc    4140
acctgattgc ccgacattat cgcgagccca tttataccca tataaatcag catccatgtt    4200
ggaatttaat cgcggcctag agcaagacgt ttcccgttga atatggctca tactcttcct    4260
```

```
ttttcaatat tattgaagca tttatcaggg ttattgtctc atgagcggat acatatttga    4320
atgtatttag aaaaataaac aaataggcat gctagcgcag aaacgtccta gaagatgcca    4380
ggaggatact tagcagagag acaataaggc cggagcgaag ccgttttccc ataggctccg    4440
ccccctgac gaacatcacg aaatctgacg ctcaaatcag tggtggcgaa acccgacagg    4500
actataaaga taccaggcgt ttccccctga tggctccctc ttgcgctctc ctgttcccgt    4560
cctgcggcgt ccgtgttgtg gtggaggctt tacccaaatc accacgtccc gttccgtgta    4620
gacagttcgc tccaagctgg gctgtgtgca agaaccccc gttcagcccg actgctgcgc    4680
cttatccggt aactatcatc ttgagtccaa cccggaaaga cacgacaaaa cgccactggc    4740
agcagccatt ggtaactgag aattagtgga tttagatatc gagagtcttg aagtggtggc    4800
ctaacagagg ctacactgaa aggacagtat ttggtatctg cgctccacta aagccagtta    4860
ccaggttaag cagttcccca actgacttaa ccttcgatca aaccgcctcc ccaggcggtt    4920
ttttcgttta cagagcagga gattacgacg atcgtaaaag gatctcaaga agatccttta    4980
cggattcccg acaccatcac tctagatttc agtgcaattt atctcttcaa atgtagcacc    5040
tgaagtcagc cccatacgat ataagttgta attctcatgt tagtcatgcc ccgcgcccac    5100
cggaaggagc tgactgggtt gaaggctctc aagggcatcg gtcgagatcc cggtgcctaa    5160
tgagtgagct aacttacatt aattgcgttg cgctcactgc ccgctttcca gtcgggaaac    5220
ctgtcgtgcc agctgcatta atgaatcggc caacgcgcgg ggagaggcgg tttgcgtatt    5280
gggcgccagg gtggtttttc ttttcaccag tgagacgggc aacagctgat tgcccttcac    5340
cgcctggccc tgagagagtt gcagcaagcg gtccacgctg gtttgcccca gcaggcgaaa    5400
atcctgtttg atggtggtta acggcgggat ataacatgag ctgtcttcgg tatcgtcgta    5460
tcccactacc gagatgtccg caccaacgcg cagcccggac tcggtaatgg cgcgcattgc    5520
gcccagcgcc atctgatcgt tggcaaccag catcgcagtg ggaacgatgc cctcattcag    5580
catttgcatg gtttgttgaa aaccggacat ggcactccag tcgccttccc gttccgctat    5640
cggctgaatt tgattgcgag tgagatattt atgccagcca gccagacgca gacgcgccga    5700
gacagaactt aatgggcccg ctaacagcgc gatttgctgg tgacccaatg cgaccagatg    5760
ctccacgccc agtcgcgtac cgtcttcatg ggagaaaata atactgttga tgggtgtctg    5820
gtcagagaca tcaagaaata cgccggaac attagtgcag gcagcttcca cagcaatggc    5880
atcctggtca tccagcggat agttaatgat cagcccactg acgcgttgcg cgagaagatt    5940
gtgcaccgcc gctttacagg cttcgacgcc gcttcgttct accatcgaca ccaccacgct    6000
ggcacccagt tgatcggcgc gagatttaat cgccgcgaca atttgcgacg gcgcgtgcag    6060
ggccagactg gaggtggcaa cgccaatcag caacgactgt ttgcccgcca gttgttgtgc    6120
cacgcggttg ggaatgtaat tcagctccgc catcgccgct tccacttttt cccgcgtttt    6180
cgcagaaacg tggctggcct ggttcaccac gcgggaaacg gtctgataag agacaccggc    6240
atactctgcg acatcgtata acgttactgg tttcacattc accaccctga attgactctc    6300
ttccgggcgc tatcatgcca taccgcgaaa ggttttgcgc cattcgatgg tgtccgggat    6360
ctcgacgctc tcccttatgc gactcctgca ttaggaaatt aatacgactc actata        6416
```

<210> SEQ ID NO 13
<211> LENGTH: 101
<212> TYPE: PRT
<213> ORGANISM: Unknown
<220> FEATURE:

<223> OTHER INFORMATION: Int-N of Cfa

<400> SEQUENCE: 13

Cys Leu Ser Tyr Asp Thr Glu Ile Leu Thr Val Glu Tyr Gly Phe Leu
1               5                   10                  15

Pro Ile Gly Lys Ile Val Glu Glu Arg Ile Glu Cys Thr Val Tyr Thr
            20                  25                  30

Val Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Lys Gln
                85                  90                  95

Val Asp Gly Leu Pro
            100

<210> SEQ ID NO 14
<211> LENGTH: 36
<212> TYPE: PRT
<213> ORGANISM: Unknown
<220> FEATURE:
<223> OTHER INFORMATION: Int-C of Cfa

<400> SEQUENCE: 14

Met Val Lys Ile Ile Ser Arg Lys Ser Leu Gly Thr Gln Asn Val Tyr
1               5                   10                  15

Asp Ile Gly Val Glu Lys Asp His Asn Phe Leu Leu Lys Asn Gly Leu
            20                  25                  30

Val Ala Ser Asn
        35

<210> SEQ ID NO 15
<211> LENGTH: 103
<212> TYPE: PRT
<213> ORGANISM: Unknown
<220> FEATURE:
<223> OTHER INFORMATION: Int-N of Npu

<400> SEQUENCE: 15

Ala Glu Tyr Cys Leu Ser Tyr Glu Thr Glu Ile Leu Thr Val Glu Tyr
1               5                   10                  15

Gly Leu Leu Pro Ile Gly Lys Ile Val Glu Lys Arg Ile Glu Cys Thr
            20                  25                  30

Val Tyr Ser Val Asp Asn Asn Gly Asn Ile Tyr Thr Gln Pro Val Ala
        35                  40                  45

Gln Trp His Asp Arg Gly Glu Gln Glu Val Phe Glu Tyr Cys Leu Glu
    50                  55                  60

Asp Gly Ser Leu Ile Arg Ala Thr Lys Asp His Lys Met Thr Val Asp
65                  70                  75                  80

Gly Gln Met Leu Pro Ile Asp Glu Ile Phe Glu Arg Glu Leu Asp Leu
                85                  90                  95

Met Arg Asp Asn Leu Pro Asn
            100

<210> SEQ ID NO 16
<211> LENGTH: 36
<212> TYPE: PRT

-continued

```
<213> ORGANISM: Unknown
<220> FEATURE:
<223> OTHER INFORMATION: Int-C of Npu

<400> SEQUENCE: 16

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35

<210> SEQ ID NO 17
<211> LENGTH: 123
<212> TYPE: PRT
<213> ORGANISM: Unknown
<220> FEATURE:
<223> OTHER INFORMATION: Int-N of Ssp

<400> SEQUENCE: 17

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120

<210> SEQ ID NO 18
<211> LENGTH: 36
<212> TYPE: PRT
<213> ORGANISM: Unknown
<220> FEATURE:
<223> OTHER INFORMATION: Int-C of Ssp

<400> SEQUENCE: 18

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
        35

<210> SEQ ID NO 19
<211> LENGTH: 101
<212> TYPE: PRT
<213> ORGANISM: Unknown
<220> FEATURE:
<223> OTHER INFORMATION: Int-N of Rma

<400> SEQUENCE: 19

Cys Phe Val Pro Gly Thr Leu Val Asn Thr Glu Asn Gly Leu Lys Lys
```

```
1               5                  10                 15
Ile Glu Glu Ile Lys Val Gly Asp Lys Val Phe Ser His Thr Gly Lys
                20                 25                 30

Leu Gln Glu Val Val Asp Thr Leu Ile Phe Asp Arg Asp Glu Glu Ile
            35                 40                 45

Ile Ser Ile Asn Gly Ile Asp Cys Thr Lys Asn His Glu Phe Tyr Val
        50                 55                 60

Ile Asp Lys Glu Asn Ala Asn Arg Val Asn Glu Asp Ile His Leu Phe
65                  70                 75                 80

Ala Arg Trp Val Val His Ala Glu Glu Leu Asp Met Lys Lys His Leu
                85                 90                 95

Leu Ile Glu Leu Glu
            100
```

<210> SEQ ID NO 20
<211> LENGTH: 37
<212> TYPE: PRT
<213> ORGANISM: Unknown
<220> FEATURE:
<223> OTHER INFORMATION: Int-C of Rma

<400> SEQUENCE: 20

```
Met Trp Asp Pro Ile Val Ser Ile Glu Pro Asp Gly Val Glu Glu Val
1               5                  10                 15

Phe Asp Leu Thr Val Pro Gly Pro His Asn Phe Val Ala Asp Asn Ile
                20                 25                 30

Ile Ala Gly Asn Ser
        35
```

<210> SEQ ID NO 21
<211> LENGTH: 118
<212> TYPE: PRT
<213> ORGANISM: Unknown
<220> FEATURE:
<223> OTHER INFORMATION: Int-N of Ppu

<400> SEQUENCE: 21

```
Cys Ile Ser Lys Phe Ser His Ile Met Trp Ser His Val Ser Lys Pro
1               5                  10                 15

Leu Phe Asn Phe Ser Ile Lys Lys Ser His Met His Asn Gly Asn Lys
                20                 25                 30

Asn Ile Tyr Gln Leu Leu Asp Gln Gly Glu Ala Phe Ile Ser Arg Gln
            35                 40                 45

Asp Lys Lys Thr Thr Tyr Lys Ile Arg Thr Asn Ser Glu Lys Tyr Leu
        50                 55                 60

Glu Leu Thr Ser Asn His Lys Ile Leu Thr Leu Arg Gly Trp Gln Arg
65                  70                 75                 80

Cys Asp Gln Leu Leu Cys Asn Asp Met Ile Thr Thr Gln Ile Gly Phe
                85                 90                 95

Glu Leu Ser Arg Lys Lys Lys Tyr Leu Leu Asn Cys Ile Pro Phe Ser
            100                105                110

Leu Cys Asn Phe Glu Thr
        115
```

<210> SEQ ID NO 22
<211> LENGTH: 34
<212> TYPE: PRT
<213> ORGANISM: Unknown
<220> FEATURE:

-continued

<223> OTHER INFORMATION: Int-C of Ppu

<400> SEQUENCE: 22

```
Met Leu Ala Asn Ile Asn Ser Asn Phe Gln Asn Val Phe Asp Phe
1               5                   10                  15
Ala Ala Asn Pro Ile Pro Asn Phe Ile Ala Asn Asn Ile Ile Val His
            20                  25                  30
Asn Ser
```

<210> SEQ ID NO 23
<211> LENGTH: 106
<212> TYPE: PRT
<213> ORGANISM: Unknown
<220> FEATURE:
<223> OTHER INFORMATION: Int-N of Cwa

<400> SEQUENCE: 23

```
Cys Leu Ser Tyr Asp Thr Glu Ile Leu Thr Val Glu Tyr Gly Ala Met
1               5                   10                  15
Tyr Ile Gly Lys Ile Val Glu Glu Asn Ile Asn Cys Thr Val Tyr Thr
            20                  25                  30
Val Asp Lys Asn Gly Phe Val Tyr Thr Gln Thr Ile Ala Gln Trp His
        35                  40                  45
Asn Arg Gly Glu Gln Glu Ile Phe Glu Tyr Asp Leu Glu Asp Gly Ser
    50                  55                  60
Lys Ile Lys Ala Thr Lys Asp His Lys Phe Met Thr Ile Asp Gly Glu
65                  70                  75                  80
Met Leu Pro Ile Asp Glu Ile Phe Glu Lys Asn Leu Asp Leu Lys Gln
                85                  90                  95
Val Val Ser His Pro Asp Asp Tyr Leu Val
            100                 105
```

<210> SEQ ID NO 24
<211> LENGTH: 37
<212> TYPE: PRT
<213> ORGANISM: Unknown
<220> FEATURE:
<223> OTHER INFORMATION: Int-C of Cwa

<400> SEQUENCE: 24

```
Met Val Lys Ile Ile Gly Cys Arg Ser Leu Gly Thr Gln Lys Val Tyr
1               5                   10                  15
Asp Ile Gly Val Glu Lys Asp His Asn Phe Leu Leu Ala Asn Gly Ser
            20                  25                  30
Ile Ala Ser Asn Cys
        35
```

<210> SEQ ID NO 25
<211> LENGTH: 118
<212> TYPE: PRT
<213> ORGANISM: Unknown
<220> FEATURE:
<223> OTHER INFORMATION: Int-N of CraS

<400> SEQUENCE: 25

```
Cys Leu Ser Tyr Glu Thr Glu Val Leu Thr Leu Glu Tyr Gly Phe Val
1               5                   10                  15
Pro Ile Gly Glu Ile Val Asn Lys Gln Met Val Cys Thr Val Phe Ser
            20                  25                  30
Leu Asn Asp Ser Gly Asn Val Tyr Thr Gln Pro Ile Gly Gln Trp His
```

```
                35                  40                  45
Asp Arg Gly Val Gln Asp Leu Tyr Glu Tyr Cys Leu Asp Asp Gly Ser
        50                  55                  60

Thr Ile Arg Ala Thr Lys Asp His Lys Phe Met Thr Thr Gln Gly Glu
65                  70                  75                  80

Met Val Pro Ile Asp Glu Ile Phe His Gln Gly Trp Glu Leu Val Gln
                85                  90                  95

Val Ser Gly Ile Ser Lys Leu Val Gln Gln Arg Thr Leu Pro Phe Ile
            100                 105                 110

Ile Val Asp Arg Lys Leu
            115

<210> SEQ ID NO 26
<211> LENGTH: 37
<212> TYPE: PRT
<213> ORGANISM: Unknown
<220> FEATURE:
<223> OTHER INFORMATION: Int-C of CraS

<400> SEQUENCE: 26

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Asn Cys
            35

<210> SEQ ID NO 27
<211> LENGTH: 99
<212> TYPE: PRT
<213> ORGANISM: Unknown
<220> FEATURE:
<223> OTHER INFORMATION: Int-N of Csp8801

<400> SEQUENCE: 27

Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
            20                  25                  30

Val Asp Lys Asn Gly Phe Val Tyr Thr Gln Asn Ile Ala Gln Trp His
            35                  40                  45

Leu Arg Gly Gln Gln Glu Val Phe Glu Tyr Tyr Leu Asp Asp Gly Ser
        50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Thr Gly Leu Glu Leu Lys Lys
                85                  90                  95

Ile Lys Ile

<210> SEQ ID NO 28
<211> LENGTH: 37
<212> TYPE: PRT
<213> ORGANISM: Unknown
<220> FEATURE:
<223> OTHER INFORMATION: Int-C of Csp8801

<400> SEQUENCE: 28

Met Val Lys Ile Val Ser Tyr Arg Ser Leu Gly Lys Gln Phe Val Tyr
1               5                   10                  15
```

Asp Ile Gly Val Ala Gln Lys His Asn Phe Leu Leu Ala Asn Gly Ser
            20                  25                  30

Ile Ala Ser Asn Cys
        35

<210> SEQ ID NO 29
<211> LENGTH: 99
<212> TYPE: PRT
<213> ORGANISM: Unknown
<220> FEATURE:
<223> OTHER INFORMATION: Int-N of Csp0110

<400> SEQUENCE: 29

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Ser Val Tyr Thr
            20                  25                  30

Val Asn Lys Asn Gly Phe Val Tyr Thr Gln Ser Ile Ala Gln Trp His
        35                  40                  45

His Arg Gly Glu Gln Glu Val Phe Glu Tyr Tyr Leu Glu Asp Gly Glu
    50                  55                  60

Thr Ile Arg Ala Thr Lys Asp His Lys Phe Met Thr Thr Glu Gly Lys
65                  70                  75                  80

Met Leu Pro Ile Asp Glu Ile Phe Glu Asn Asn Leu Asp Leu Lys Lys
                85                  90                  95

Leu Thr Val

<210> SEQ ID NO 30
<211> LENGTH: 37
<212> TYPE: PRT
<213> ORGANISM: Unknown
<220> FEATURE:
<223> OTHER INFORMATION: Int-C of Csp0110

<400> SEQUENCE: 30

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Asn Cys
        35

<210> SEQ ID NO 31
<211> LENGTH: 104
<212> TYPE: PRT
<213> ORGANISM: Unknown
<220> FEATURE:
<223> OTHER INFORMATION: Int-N of Mcht

<400> SEQUENCE: 31

Cys Leu Ser Tyr Asp Thr Gln Ile Leu Thr Val Glu Tyr Gly Ala Val
1               5                   10                  15

Ala Ile Gly Glu Ile Val Glu Lys Gln Ile Glu Cys Thr Val Tyr Ser
            20                  25                  30

Val Asp Glu Asn Gly Tyr Val Tyr Thr Gln Pro Ile Ala Gln Trp His
        35                  40                  45

Asn Arg Gly Glu Gln Glu Val Phe Glu Tyr Leu Leu Glu Asp Gly Ala
    50                  55                  60

Thr Ile Arg Ala Thr Lys Asp His Lys Phe Met Thr Asp Glu Asp Gln
65                  70                  75                  80

```
Met Leu Pro Ile Asp Gln Ile Phe Glu Gln Gly Leu Glu Leu Lys Gln
                85                  90                  95

Val Glu Val Leu Gln Pro Val Phe
            100
```

<210> SEQ ID NO 32
<211> LENGTH: 37
<212> TYPE: PRT
<213> ORGANISM: Unknown
<220> FEATURE:
<223> OTHER INFORMATION: Int-C of Mcht

<400> SEQUENCE: 32

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                20                  25                  30

Ile Gln Ser Asn Cys
        35
```

<210> SEQ ID NO 33
<211> LENGTH: 100
<212> TYPE: PRT
<213> ORGANISM: Unknown
<220> FEATURE:
<223> OTHER INFORMATION: Int-N of Maer

<400> SEQUENCE: 33

```
Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Cys Thr Val Tyr Thr
                20                  25                  30

Val Asp Gln Asn Gly Phe Val Tyr Ser Gln Pro Ile Ser Gln Trp His
                35                  40                  45

Glu Arg Gly Leu Gln Glu Val Phe Glu Tyr Thr Leu Glu Asn Gly Gln
            50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser
            100
```

<210> SEQ ID NO 34
<211> LENGTH: 37
<212> TYPE: PRT
<213> ORGANISM: Unknown
<220> FEATURE:
<223> OTHER INFORMATION: Int-C of Maer

<400> SEQUENCE: 34

```
Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
                20                  25                  30

Ile Ala Ser Asn Cys
        35
```

<210> SEQ ID NO 35
<211> LENGTH: 102

```
<212> TYPE: PRT
<213> ORGANISM: Unknown
<220> FEATURE:
<223> OTHER INFORMATION: Int-N of Asp

<400> SEQUENCE: 35

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Asn Gly Ile Val Tyr Thr Gln Pro Ile Ala Gln Trp His
                35                  40                  45

His Arg Gly Lys Gln Glu Val Phe Glu Tyr Cys Leu Glu Asp Gly Ser
        50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 36
<211> LENGTH: 37
<212> TYPE: PRT
<213> ORGANISM: Unknown
<220> FEATURE:
<223> OTHER INFORMATION: Int-C of Asp

<400> SEQUENCE: 36

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Asn Cys
        35

<210> SEQ ID NO 37
<211> LENGTH: 112
<212> TYPE: PRT
<213> ORGANISM: Unknown
<220> FEATURE:
<223> OTHER INFORMATION: Int-N of Oli

<400> SEQUENCE: 37

Cys Leu Ser Tyr Asn Thr Glu Val Leu Thr Val Glu Tyr Gly Pro Leu
1               5                   10                  15

Pro Ile Gly Lys Ile Val Asp Glu Gln Ile His Cys Arg Val Tyr Ser
            20                  25                  30

Val Asp Glu Asn Gly Phe Val Tyr Thr Gln Ala Ile Ala Gln Trp His
                35                  40                  45

Asp Arg Gly Tyr Gln Glu Ile Phe Ala Tyr Glu Leu Ala Asp Gly Ser
        50                  55                  60

Val Ile Arg Ala Thr Lys Asp His Gln Phe Met Thr Glu Asp Gly Gln
65                  70                  75                  80

Met Phe Pro Ile Asp Glu Ile Trp Glu Lys Gly Leu Asp Leu Lys Lys
                85                  90                  95

Leu Pro Thr Val Gln Asp Leu Pro Ala Ala Val Gly Tyr Thr Val Ser
            100                 105                 110
```

```
<210> SEQ ID NO 38
<211> LENGTH: 37
<212> TYPE: PRT
<213> ORGANISM: Unknown
<220> FEATURE:
<223> OTHER INFORMATION: Int-C of Oli

<400> SEQUENCE: 38

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Asn Cys
            35

<210> SEQ ID NO 39
<211> LENGTH: 101
<212> TYPE: PRT
<213> ORGANISM: Unknown
<220> FEATURE:
<223> OTHER INFORMATION: Int-N of Aov
<220> FEATURE:
<221> NAME/KEY: misc_feature
<222> LOCATION: (87)..(87)
<223> OTHER INFORMATION: Xaa can be any naturally occurring amino acid

<400> SEQUENCE: 39

Cys Leu Ser Ala Asp Thr Glu Ile Leu Thr Val Glu Tyr Gly Phe Leu
1               5                   10                  15

Pro Ile Gly Glu Ile Val Gly Lys Ala Ile Glu Cys Arg Val Tyr Ser
            20                  25                  30

Val Asp Gly Asn Gly Asn Ile Tyr Thr Gln Ser Ile Ala Gln Trp His
        35                  40                  45

Asn Arg Gly Glu Gln Glu Val Phe Glu Tyr Thr Leu Glu Asp Gly Ser
    50                  55                  60

Ile Ile Arg Ala Thr Lys Asp His Lys Phe Met Thr Thr Asp Gly Glu
65                  70                  75                  80

Met Leu Pro Ile Asp Glu Xaa Phe Ala Arg Gln Leu Asp Leu Met Gln
                85                  90                  95

Val Gln Gly Leu Met
            100

<210> SEQ ID NO 40
<211> LENGTH: 37
<212> TYPE: PRT
<213> ORGANISM: Unknown
<220> FEATURE:
<223> OTHER INFORMATION: Int-C of Aov

<400> SEQUENCE: 40

Met Val Lys Ile Thr Ala Arg Lys Phe Val Gly Arg Glu Asn Val Tyr
1               5                   10                  15

Asp Ile Gly Val Glu His His Asn Phe Ala Ile Lys Asn Gly Leu
            20                  25                  30

Ile Ala Ser Asn Cys
            35

<210> SEQ ID NO 41
<211> LENGTH: 101
<212> TYPE: PRT
<213> ORGANISM: Unknown
<220> FEATURE:
<223> OTHER INFORMATION: Int-N of Ter-3
```

<400> SEQUENCE: 41

Cys Leu Thr Tyr Glu Thr Glu Ile Met Thr Val Glu Tyr Gly Pro Leu
1               5                   10                  15

Pro Ile Gly Lys Ile Val Glu Tyr Arg Ile Glu Cys Thr Val Tyr Thr
            20                  25                  30

Val Asp Lys Asn Cys Tyr Ile Tyr Thr Gln Pro Ile Ala Gln Trp His
        35                  40                  45

Asn Arg Gly Met Gln Glu Val Tyr Glu Tyr Ser Leu Glu Asp Gly Thr
    50                  55                  60

Val Ile Arg Ala Thr Pro Glu His Lys Phe Met Thr Glu Asp Gly Gln
65                  70                  75                  80

Met Leu Pro Ile Asp Glu Ile Phe Glu Arg Asn Leu Asp Leu Lys Cys
                85                  90                  95

Leu Gly Thr Leu Glu
            100

<210> SEQ ID NO 42
<211> LENGTH: 37
<212> TYPE: PRT
<213> ORGANISM: Unknown
<220> FEATURE:
<223> OTHER INFORMATION: Int-C of Ter-3

<400> SEQUENCE: 42

Met Val Lys Ile Val Ser Arg Lys Leu Ala Lys Thr Glu Asn Val Tyr
1               5                   10                  15

Asp Ile Gly Val Arg Lys Asp His Asn Phe Val Leu Ala Asn Gly Leu
            20                  25                  30

Ile Ala Ser Asn Cys
        35

<210> SEQ ID NO 43
<211> LENGTH: 106
<212> TYPE: PRT
<213> ORGANISM: Unknown
<220> FEATURE:
<223> OTHER INFORMATION: Int-N of Ssp7002

<400> SEQUENCE: 43

Cys Leu Ala Gly Gly Thr Pro Val Val Thr Glu Tyr Gly Val Leu
1               5                   10                  15

Pro Ile Thr Ile Val Glu Gln Glu Leu Leu Cys His Val Tyr Ser Val
            20                  25                  30

Asp Ala Gln Gly Leu Ile Thr Ala Gln Leu Ile Glu Gln Trp His Gln
        35                  40                  45

Arg Gly Asp Arg Leu Leu Tyr Glu Tyr Glu Leu Glu Asn Gly Gln Met
    50                  55                  60

Ile Arg Ala Thr Pro Asp His Arg Phe Leu Thr Thr Thr Gly Glu Leu
65                  70                  75                  80

Leu Pro Ile Asp Glu Ile Phe Thr Gln Asn Leu Asp Leu Ala Ala Trp
                85                  90                  95

Ala Val Pro Asp Ser Leu Pro Arg Thr Ala
            100                 105

<210> SEQ ID NO 44
<211> LENGTH: 37
<212> TYPE: PRT
<213> ORGANISM: Unknown

```
<220> FEATURE:
<223> OTHER INFORMATION: Int-C of Ssp7002

<400> SEQUENCE: 44

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Asn Cys
        35

<210> SEQ ID NO 45
<211> LENGTH: 117
<212> TYPE: PRT
<213> ORGANISM: Unknown
<220> FEATURE:
<223> OTHER INFORMATION: Int-N of Tvu

<400> SEQUENCE: 45

Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
            20                  25                  30

Leu Asp Pro Gln Gly His Leu Tyr Thr Gln Pro Ile Ala Gln Trp His
        35                  40                  45

Phe Gln Gly Phe Arg Pro Val Tyr Ala Tyr Gln Leu Glu Asp Gly Ser
    50                  55                  60

Thr Ile Cys Ala Thr Pro Asp His Arg Phe Met Thr Thr Ser Gly Gln
65                  70                  75                  80

Met Leu Pro Ile Glu Gln Ile Phe Arg Glu Gly Leu Glu Leu Trp Gln
                85                  90                  95

Val Ala Ile Ala Pro Pro Gly Ala Leu Ala Gln Gly Leu Lys Pro Ala
            100                 105                 110

Val Gln Met Ser Cys
        115

<210> SEQ ID NO 46
<211> LENGTH: 36
<212> TYPE: PRT
<213> ORGANISM: Unknown
<220> FEATURE:
<223> OTHER INFORMATION: Int-C of Tvu

<400> SEQUENCE: 46

Met Lys Ile Val Gly Arg Arg Leu Val Gly Trp Gln Ala Val Tyr Asp
1               5                   10                  15

Ile Cys Leu Ala Gly Asp His Asn Phe Leu Leu Ala Asn Gly Ala Ile
            20                  25                  30

Ala Ala Asn Cys
        35

<210> SEQ ID NO 47
<211> LENGTH: 117
<212> TYPE: PRT
<213> ORGANISM: Unknown
<220> FEATURE:
<223> OTHER INFORMATION: Int-N of Tel

<400> SEQUENCE: 47

Cys Leu Ser Gly Glu Thr Ala Val Met Thr Val Glu Tyr Gly Ala Val
1               5                   10                  15
```

Pro Ile Arg Arg Leu Val Gln Glu Arg Leu Ser Cys His Val Tyr Ser
            20                  25                  30

Leu Asp Gly Gln Gly His Leu Tyr Thr Gln Pro Ile Ala Gln Trp His
        35                  40                  45

Phe Gln Gly Phe Arg Phe Val Tyr Glu Tyr Gln Leu Glu Asp Gly Ser
50                  55                  60

Thr Ile Cys Ala Thr Pro Asp His Arg Phe Met Thr Thr Arg Gly Gln
65                  70                  75                  80

Met Leu Pro Ile Glu Gln Ile Phe Gln Glu Gly Leu Glu Leu Trp Gln
                85                  90                  95

Val Ala Ile Ala Pro Arg Gln Ala Leu Leu Gln Gly Leu Lys Pro Ala
            100                 105                 110

Val Gln Met Ser Gly
        115

<210> SEQ ID NO 48
<211> LENGTH: 36
<212> TYPE: PRT
<213> ORGANISM: Unknown
<220> FEATURE:
<223> OTHER INFORMATION: Int-C of Tel

<400> SEQUENCE: 48

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Asn Cys
        35

<210> SEQ ID NO 49
<211> LENGTH: 113
<212> TYPE: PRT
<213> ORGANISM: Unknown
<220> FEATURE:
<223> OTHER INFORMATION: Int-N of Sel

<400> SEQUENCE: 49

Cys Leu Ala Ala Asp Thr Glu Val Leu Thr Val Glu Tyr Gly Pro Ile
1               5                   10                  15

Ala Ile Gly Lys Leu Val Glu Glu Asn Ile Arg Cys Gln Val Tyr Cys
            20                  25                  30

Cys Asn Pro Asp Gly Tyr Ile Tyr Ser Gln Pro Ile Gly Gln Trp His
        35                  40                  45

Gln Arg Gly Glu Gln Glu Val Ile Glu Tyr Glu Leu Ser Asp Gly Arg
    50                  55                  60

Ile Ile Arg Ala Thr Ala Asp His Arg Phe Met Thr Glu Glu Gly Glu
65                  70                  75                  80

Met Leu Ser Leu Asp Glu Ile Phe Glu Arg Ser Leu Glu Leu Lys Gln
                85                  90                  95

Ile Pro Thr Pro Leu Leu Ala Ile Ala Gln Pro Ser Pro Leu Ala Thr
            100                 105                 110

Ala

<210> SEQ ID NO 50
<211> LENGTH: 37
<212> TYPE: PRT
<213> ORGANISM: Unknown

<220> FEATURE:
<223> OTHER INFORMATION: Int-C of Sel

<400> SEQUENCE: 50

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Asn Cys
        35

<210> SEQ ID NO 51
<211> LENGTH: 110
<212> TYPE: PRT
<213> ORGANISM: Unknown
<220> FEATURE:
<223> OTHER INFORMATION: Int-N of Aha

<400> SEQUENCE: 51

Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Ser Cys Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
    50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met Ser Leu Leu Arg Arg Gly Ala Lys
            100                 105                 110

<210> SEQ ID NO 52
<211> LENGTH: 37
<212> TYPE: PRT
<213> ORGANISM: Unknown
<220> FEATURE:
<223> OTHER INFORMATION: Int-C of Aha

<400> SEQUENCE: 52

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Asn Cys
        35

<210> SEQ ID NO 53
<211> LENGTH: 88
<212> TYPE: PRT
<213> ORGANISM: Unknown
<220> FEATURE:
<223> OTHER INFORMATION: Gp41.1N

<400> SEQUENCE: 53

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

```
Asn Glu Val Leu Asn Val Phe Pro Lys Ser Lys Lys Ser Tyr Lys
            35                  40                  45
Ile Thr Leu Glu Asp Gly Lys Glu Ile Ile Cys Ser Glu Glu His Leu
     50                  55                  60
Phe Pro Thr Gln Thr Gly Glu Met Asn Ile Ser Gly Gly Leu Lys Glu
 65                  70                  75                  80
Gly Met Cys Leu Tyr Val Lys Glu
                 85
```

<210> SEQ ID NO 54
<211> LENGTH: 37
<212> TYPE: PRT
<213> ORGANISM: Unknown
<220> FEATURE:
<223> OTHER INFORMATION: Gp41.1C

<400> SEQUENCE: 54

```
Met Met Leu Lys Lys Ile Leu Lys Ile Glu Glu Leu Asp Glu Arg Glu
 1               5                  10                  15
Leu Ile Asp Ile Glu Val Ser Gly Asn His Leu Phe Tyr Ala Asn Asp
                 20                  25                  30
Ile Leu Thr His Asn
         35
```

<210> SEQ ID NO 55
<211> LENGTH: 59
<212> TYPE: DNA
<213> ORGANISM: Artificial Sequence
<220> FEATURE:
<223> OTHER INFORMATION: pCDLCHN Insert FW for LC-HN

<400> SEQUENCE: 55
ataaggagat ataccatgcc attcgttaat aagcaattta actacaaaga cccagtaaa        59

<210> SEQ ID NO 56
<211> LENGTH: 63
<212> TYPE: DNA
<213> ORGANISM: Artificial Sequence
<220> FEATURE:
<223> OTHER INFORMATION: pCDLCHN Insert BW for LC-HN

<400> SEQUENCE: 56
gtgatggctg ctgccattct taatatactc agtaaaggtg ctaagcaact ttttattatc       60
cac                                                                    63

<210> SEQ ID NO 57
<211> LENGTH: 24
<212> TYPE: DNA
<213> ORGANISM: Artificial Sequence
<220> FEATURE:
<223> OTHER INFORMATION: pCDLCHN Vector FW for pColaDuet, pETDuet

<400> SEQUENCE: 57
ggcagcagcc atcaccatca tcac                                             24

<210> SEQ ID NO 58
<211> LENGTH: 54
<212> TYPE: DNA
<213> ORGANISM: Artificial Sequence
<220> FEATURE:
<223> OTHER INFORMATION: pCDLCHN Vector BW for pColaDuet, pETDuet

<400> SEQUENCE: 58
ggtatatctc cttattaaag ttaaacaaaa ttatttctac aggggaattg ttat         54

<210> SEQ ID NO 59
<211> LENGTH: 22
<212> TYPE: DNA
<213> ORGANISM: Artificial Sequence
<220> FEATURE:
<223> OTHER INFORMATION: Col FW for pColaDuet

<400> SEQUENCE: 59
tcagctccgc catcgccgct tc                                           22

<210> SEQ ID NO 60
<211> LENGTH: 28
<212> TYPE: DNA
<213> ORGANISM: Artificial Sequence
<220> FEATURE:
<223> OTHER INFORMATION: Col BW for pColaDuet

<400> SEQUENCE: 60
tcgcagcagc ggtttcttta ccagactc                                     28

<210> SEQ ID NO 61
<211> LENGTH: 59
<212> TYPE: DNA
<213> ORGANISM: Artificial Sequence
<220> FEATURE:
<223> OTHER INFORMATION: pCLC Insert FW for LC

<400> SEQUENCE: 61
ataaggagat ataccatgcc attcgttaat aagcaattta actacaaaga cccagtaaa   59

<210> SEQ ID NO 62
<211> LENGTH: 54
<212> TYPE: DNA
<213> ORGANISM: Artificial Sequence
<220> FEATURE:
<223> OTHER INFORMATION: pCLC Insert BW for LC

<400> SEQUENCE: 62
gtgatggctc tgcctttgaa tggaataatt ccgcgtacgc ataacaattt gtag         54

<210> SEQ ID NO 63
<211> LENGTH: 24
<212> TYPE: DNA
<213> ORGANISM: Artificial Sequence
<220> FEATURE:
<223> OTHER INFORMATION: pCDHC Vector FW for pColaDuet, pETDuet

<400> SEQUENCE: 63
ggcagcagcc atcaccatca tcac                                         24

<210> SEQ ID NO 64
<211> LENGTH: 51
<212> TYPE: DNA
<213> ORGANISM: Artificial Sequence
<220> FEATURE:
<223> OTHER INFORMATION: pCDHC Vector BW for pColaDuet, pETDuet

<400> SEQUENCE: 64
catggtatat ctccttatta agttaaaca aaattatttc tacaggggaa t             51

<210> SEQ ID NO 65
<211> LENGTH: 66
<212> TYPE: DNA

<213> ORGANISM: Artificial Sequence
<220> FEATURE:
<223> OTHER INFORMATION: pCHC Insert FW for Hc

<400> SEQUENCE: 65
aggagatata ccatgatagt taataccagt atcttatcta tcgtttacaa aaaggatgac    60
ctgata                                                              66

<210> SEQ ID NO 66
<211> LENGTH: 60
<212> TYPE: DNA
<213> ORGANISM: Artificial Sequence
<220> FEATURE:
<223> OTHER INFORMATION: pCHC Insert BW for Hc

<400> SEQUENCE: 66
gtgatggctg ctgcctaagc tactttctcc ccatccgtcg tcgacgggga tgaactccca    60

<210> SEQ ID NO 67
<211> LENGTH: 54
<212> TYPE: DNA
<213> ORGANISM: Artificial Sequence
<220> FEATURE:
<223> OTHER INFORMATION: pCHN Insert FW for HN

<400> SEQUENCE: 67
aggagatata ccatgacgaa gtctttagat gaaggttaca ataaggcact gaat          54

<210> SEQ ID NO 68
<211> LENGTH: 63
<212> TYPE: DNA
<213> ORGANISM: Artificial Sequence
<220> FEATURE:
<223> OTHER INFORMATION: pCHN Insert BW for HN

<400> SEQUENCE: 68
gtgatggctg ctgccattct taatatactc agtaaaggtg ctaagcaact ttttattatc    60
cac                                                                 63

<210> SEQ ID NO 69
<211> LENGTH: 47
<212> TYPE: DNA
<213> ORGANISM: Artificial Sequence
<220> FEATURE:
<223> OTHER INFORMATION: CfaC Insert FW for CfaC

<400> SEQUENCE: 69
ataaggagat ataccatggt caagatcatt agtcgtaaga gtctggg                 47

<210> SEQ ID NO 70
<211> LENGTH: 42
<212> TYPE: DNA
<213> ORGANISM: Artificial Sequence
<220> FEATURE:
<223> OTHER INFORMATION: CfaC Insert BW for CfaC

<400> SEQUENCE: 70
attcggatcc tggcttaagc tactttctcc ccatccgtcg tc                      42

<210> SEQ ID NO 71
<211> LENGTH: 15
<212> TYPE: DNA
<213> ORGANISM: Artificial Sequence
<220> FEATURE:
<223> OTHER INFORMATION: CfaC Vector FW for pET28a CfaC

```
<400> SEQUENCE: 71
agccaggatc cgaat                                                    15

<210> SEQ ID NO 72
<211> LENGTH: 15
<212> TYPE: DNA
<213> ORGANISM: Artificial Sequence
<220> FEATURE:
<223> OTHER INFORMATION: CfaC Vector BW for pET28a CfaC

<400> SEQUENCE: 72
ggtatatctc cttat                                                    15

<210> SEQ ID NO 73
<211> LENGTH: 44
<212> TYPE: DNA
<213> ORGANISM: Artificial Sequence
<220> FEATURE:
<223> OTHER INFORMATION: CfaN Insert FW for CfaN

<400> SEQUENCE: 73
gagtatatta agaattgcct gtcttacgac acagagattc tgac                    44

<210> SEQ ID NO 74
<211> LENGTH: 64
<212> TYPE: DNA
<213> ORGANISM: Artificial Sequence
<220> FEATURE:
<223> OTHER INFORMATION: CfaN Insert BW for CfaN

<400> SEQUENCE: 74
gtgatggctg ctgccatgat gatgatgatg atgcggcaaa ccatcaactt gtttcaggtc   60
taac                                                                64

<210> SEQ ID NO 75
<211> LENGTH: 15
<212> TYPE: DNA
<213> ORGANISM: Artificial Sequence
<220> FEATURE:
<223> OTHER INFORMATION: CfaN Vector FW for pColaDuet CfaC

<400> SEQUENCE: 75
ggcagcagcc atcac                                                    15

<210> SEQ ID NO 76
<211> LENGTH: 15
<212> TYPE: DNA
<213> ORGANISM: Artificial Sequence
<220> FEATURE:
<223> OTHER INFORMATION: CfaN Vector BW for pColaDuet CfaC

<400> SEQUENCE: 76
attcttaata tactc                                                    15
```

METHOD FOR SAFELY PRODUCING BOTULINUM NEUROTOXIN

CROSS REFERENCE TO RELATED APPLICATIONS

This application is a National Stage of International Application No. PCT/KR2020/018623 filed Dec. 18, 2020, claiming priority based on Korean Patent Application No. 10-2019-0169553 filed Dec. 18, 2019, the entire disclosures of which are incorporated herein by reference.

INCORPORATION BY REFERENCE OF SEQUENCE LISTING

The content of the electronically submitted sequence listing, file name: Q272837substitutesequencelistingasfiled.txt; size: 121,600 bytes; and date of creation: Aug. 9, 2024, filed herewith, is incorporated herein by reference in its entirety.

TECHNICAL FIELD

The present invention relates to a method for safely producing botulinum toxin by preparing a plurality of botulinum toxin fragments and then reassembling the same.

BACKGROUND ART

In order to control the relaxation and contraction of muscle, there is a neuromuscular junction in the upper layer of the muscles, and synaptic vesicles are located in the nerve terminal. Muscles contract upon receiving a message from neurotransmitters, transmitted from inside a type of neurovesicle. In order for the neurotransmitters to be released as described above, the neurotransmitters must dock with muscles through formation of complexes of soluble n-ethylmaleimide-sensitive-factor attachment receptor (SNARE) proteins. Specifically, when the neurotransmitter is released, the synaptic vesicle containing the neurotransmitter must be fused with the presynaptic membrane in order to form a passage across the boundary therebetween. At this time, the membrane fusion is caused by SNARE which exists as a complex of three proteins. In particular, the neurotransmitter release passage is opened by fusion between the synaptic vesicle and the presynaptic membrane. The t-SNARE complex, which is a complex of Syntaxin 1a protein and SNAP-25 protein, anchored in the target membrane, and v-SNARE, anchored in the vesicle, are involved. These proteins are twisted like a pretzel. During membrane fusion, rearrangement of the lipid bilayer occurs, as is well known in the art. Biological membranes physically repel each other strongly, so they do not spontaneously fuse with each other and a strong external force should be applied in order to overcome the repulsive force between the membranes. At this time, it is the SNARE protein that creates a force strong enough to overcome the repulsive force between the membranes. In other words, formation of the SNARE complex is a source of force for overcoming the repulsive force between the membranes, and is a key phenomenon of exocytosis, including the release of neurotransmitters (Weber et al., Cell, 92, 759-772(1998)). Meanwhile, unless the SNARE conjugation and twisting process is fully completed, membrane fusion fails and thus neurotransmitter release does not occur, resulting in loss of muscle movement. This process means that it is possible to prevent the formation of wrinkles by frequently used muscles and to ameliorate wrinkles that are formed. That is, the formation of wrinkles by muscle movement can be inhibited and formed wrinkles can be ameliorated based on the effect of inhibiting SNARE formation. Furthermore, contraction of muscle cells surrounding sweat glands functions to stimulate the sweat glands to release sweat. Such contraction of muscle cells around sweat glands also results from the release of neurotransmitters from neurons. Excessive release of neurotransmitters at the neuromuscular junction causes excessive sweating, which is a condition called "hyperhidrosis". Therefore, the condition of hyperhidrosis can be treated or alleviated by inhibiting the formation of SNARE complexes in neurons resident at the neuromuscular junction. SNARE (soluble N-ethylmaleimide-sensitive factor attachment protein receptor; SNAP receptor) proteins are a large protein superfamily including more than 60 members, and are present in yeast and mammalian cells. The main role of SNARE proteins is to mediate vesicle fusion. That is, SNAREs anchored to compartments such as lysosomes mediate the fusion of vesicles with the target membrane. In a specific example, SNARE is involved in docking of the presynaptic membrane and the synaptic vesicle in neurons.

Representative substances targeting the SNARE include bacterial neurotoxins that cause botulism and tetanus. Botulinum toxin is a potent polypeptide neurotoxin produced from *Clostridium botulinum*, which is an anaerobic, gram-positive bacterium. These neurotoxins cause neuroparalytic diseases in humans and animals. *Clostridium botulinum* is found in soil, but may be cultured in sealed food containers that have not been properly sterilized. Botulinum toxin is known to have high affinity for cholinergic motor neurons and to enter neurons and inhibit the presynaptic release of acetylcholine. Botulinum toxin uptake may cause various symptoms, such as gait disturbance, dysphagia, and speech disturbance. Paralysis of the respiratory muscles may lead to death. The mortality rate of botulinum toxin is about 1.8 billion times that of diphtheria, 600 million times that of sodium cyanide, 30 million times that of cobrotoxin, and 12 million times that of cholera on a molar basis (Singh, Critical Aspects of Bacterial Protein Toxins, page 63-84 (chapter 4) of Natural Toxins II, edited by B. R. Sigh et al., Plenum Press, New York (1976)). For example, *Clostridium botulinum*-derived neurotoxin is a main component of a drug known as "botulinum toxin", and botulinum toxin is known to be mainly used for cosmetic procedures such as wrinkle removal, but is also used in treatment related to secretion of transmitters and/or for muscle-related diseases such as strabismus, blepharospasm, vocal cord disorders, torticollis, myocardial disorders, ulcers and acid reflux, reduced appetite, pancreatic diseases, stretchmarks, urge incontinence, dentition, polio, myalgia, hip deformity, hyperhidrosis, back pain, neck pain, chronic headaches, and cranial nerve disorder. Specifically, botulinum toxin blocks the release of neurotransmitters by suppressing membrane fusion by inhibiting SNARE complex formation after a neurotoxin, the main component thereof, specifically acts on the SNARE present in neurons. Accordingly, botulinum toxin is known to have an effect of treating the diseases described above by inhibiting muscular movement or the sympathetic or parasympathetic nervous system.

The botulinum neurotoxin (BoNT) protein is largely divided into two parts, namely, a heavy chain (HC, about 100 kDa) and a light chain (LC, about 50 kDa) having enzymatic activity that cleaves the protein forming the SNARE complex in neurons, wherein the heavy chain is classified into a part having the function of recognizing and binding neurons, which is called a "receptor-binding domain" (RBD or $H_C$), and a part having the function of moving the light chain into the neuroplasm, which is called a "translocation domain" ($H_N$). When BoNT is attached to the presynaptic membrane and is absorbed into the cell through endocytosis, absorption can be performed by forming vesicles from the presynaptic membrane. In order for BoNTs to inhibit SNARE complex formation, escape from the vesicle lumen into the cytoplasm is required. At this time, the part that moves the BoNT light chain from the vesicle to the cytoplasm is a translocation domain of the heavy chain. When the pH in the vesicle decreases, the α-helices in the translocation domain form a channel in the vesicle membrane, and the light chain passes through the channel, moves to the cytoplasm, and is then present in an activated form in the cytoplasm when the disulfide bond with the heavy chain is cleaved by a thioredoxin reductase. In addition, the toxin protein is released as a single chain from the bacteria and is then split into two chains by the protease inherent thereto. The two chains are linked to each other again through a disulfide bond and then exist in a size of about 150 kDa. A process of cleaving the single chain released from the bacteria and then holding the same together again is required, thus inevitably causing a decrease in yield and an increase in production costs. In addition, production of toxins entails production permits and very high costs for related safety equipment. In addition, accidental or unintended leakage may cause enormous damage to the environment and the human body because all of the genes encoding the toxin are contained in one cell capable of proliferation.

Meanwhile, a process of screening strains producing BoNT in nature is very difficult. Searching for strains producing a desired type of toxin is required, and the found strains should have sufficient productivity. It is also very difficult to produce a full-length toxin in a recombinant *E. coli* other than *Clostridium botulinum*. First, it is difficult to express soluble proteins 150 kDa in size in *E. coli* cells. Many proteins are expressed as insoluble inclusion bodies in *E. coli*. In addition, interchain and intrachain disulfide bonds exist in BoNT, but it is known that disulfide bonds are not formed in *E. coli* cells. In addition, the light and heavy chains must be cleaved accurately. If not, other sites may be cleaved, thereby producing an inactivated toxin.

In order to solve these problems, in the present invention, a method for producing BoNTs in a split manner through genetic recombination has been devised. Fragments (i.e., some regions) of BoNT are known to be inherently non-toxic. When the gene encoding the BoNT fragment proteins (i.e., a part of the entire BoNT gene) is produced using genetic recombination, each recombinant cell and each recombinant protein are non-toxic and can be safely produced. However, this method can be applied to the split production only when there is a method of efficiently binding the split BoNT fragments to one another again. Unless these BoNT fragments are assembled into a full-length toxin, they remain as inactive fragments and thus fail to restore the toxin function thereof. For this purpose, a method including separately producing light chains and heavy chains and forming disulfide bonds therebetween may be considered at present. The light chains and the heavy chains are separately expressed in different cells and purified, disulfide bonds between the two chains are formed, and then the resulting full-length toxin is purified. However, first, this method has a big problem in that heavy chains are not expressed in an active form in *E. coli* (Zhou Y., Singh B. R. Protein Expr. Purif. 2004; 34:8-16; Band P. A., Blais S., Neubert T. A., Cardozo T. J., Ichtchenko K. Protein Expr. Purif. 2010; 71:62-73.). In addition, this method has low yield due to difficulty in quickly and accurately forming disulfide bonds between light chains and heavy chains in vitro, and is thus economically disadvantageous due to the necessity for an additional purification process. More importantly, reliance on safety facilities, which is the biggest disadvantage of split production, occurs again due to the difficulty in forming disulfide bonds. Therefore, it is also very important to introduce a technique for efficiently re-splicing the split toxin protein fragments into a full-length toxin.

Accordingly, a method of economically and safely producing BoNT according to the present invention was completed by combining a method of producing split toxin proteins with a process of efficiently splicing the fragments.

DISCLOSURE

Technical Problem

Therefore, it is one object of the present invention to provide a plasmid for producing botulinum toxin.

It is another object of the present invention to provide a host cell transformed with the plasmid for producing botulinum toxin.

It is another object of the present invention to provide fragments of botulinum toxin.

It is another object of the present invention to provide full-length botulinum toxin.

It is another object of the present invention to provide a pharmaceutical composition for ameliorating or treating a neurological disease.

It is another object of the present invention to provide a method for producing botulinum toxin.

Technical Solution

In accordance with an aspect of the present invention, the above and other objects can be accomplished by the provision of a plasmid for producing botulinum toxin, the plasmid encoding fragments of botulinum toxin.

In accordance with another aspect of the present invention, provided is a host cell transformed with the plasmid.

In accordance with another aspect of the present invention, provided are fragments of botulinum toxin produced using the plasmid for producing botulinum toxin.

In accordance with another aspect of the present invention, provided is a full-length botulinum toxin, produced by mixing the fragments of botulinum toxin.

In accordance with another aspect of the present invention, provided is a pharmaceutical composition for ameliorating or treating a neurological disease, containing the botulinum toxin as an active ingredient.

In accordance with another aspect of the present invention, provided is a method for producing botulinum toxin, the method including producing fragments of botulinum toxin and mixing the fragments to form full-length botulinum toxin.

Advantageous Effects

The present invention is capable of overcoming high complexity, low safety, and economic feasibility due to toxicity in production by separately producing light and heavy chains of botulinum toxin in the form of two to three fragments and then assembling the fragments into a full-length toxin, has the effect of greatly reducing production times compared to conventional production methods because a soluble toxin can be produced using bacteria, and can improve the range of pharmaceutical application of the toxin owing to possible conjugation of the produced toxin fragments with other proteins and nanoparticles.

A: LC, TD of HC ($H_N$), and RBD of HC ($H_C$) in botulinum toxin, and

Figure 1A:
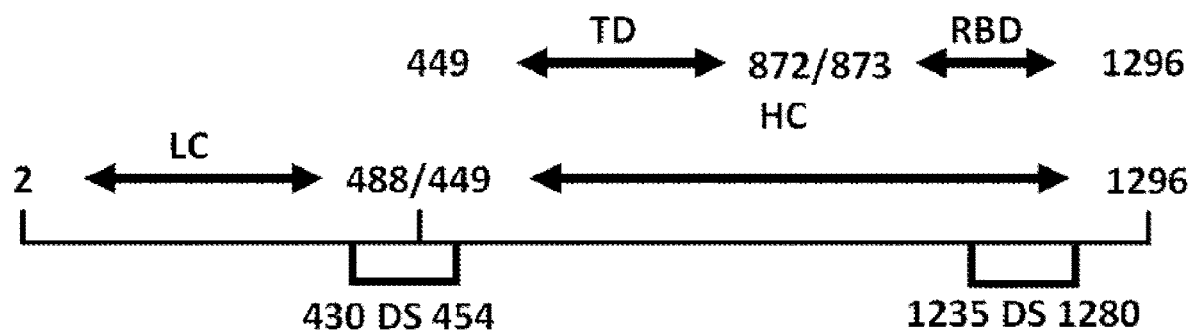
FIG. 1 illustrates fragments of botulinum toxin of the present invention and a full-length botulinum toxin assembly process using the same.
Figure 1B:
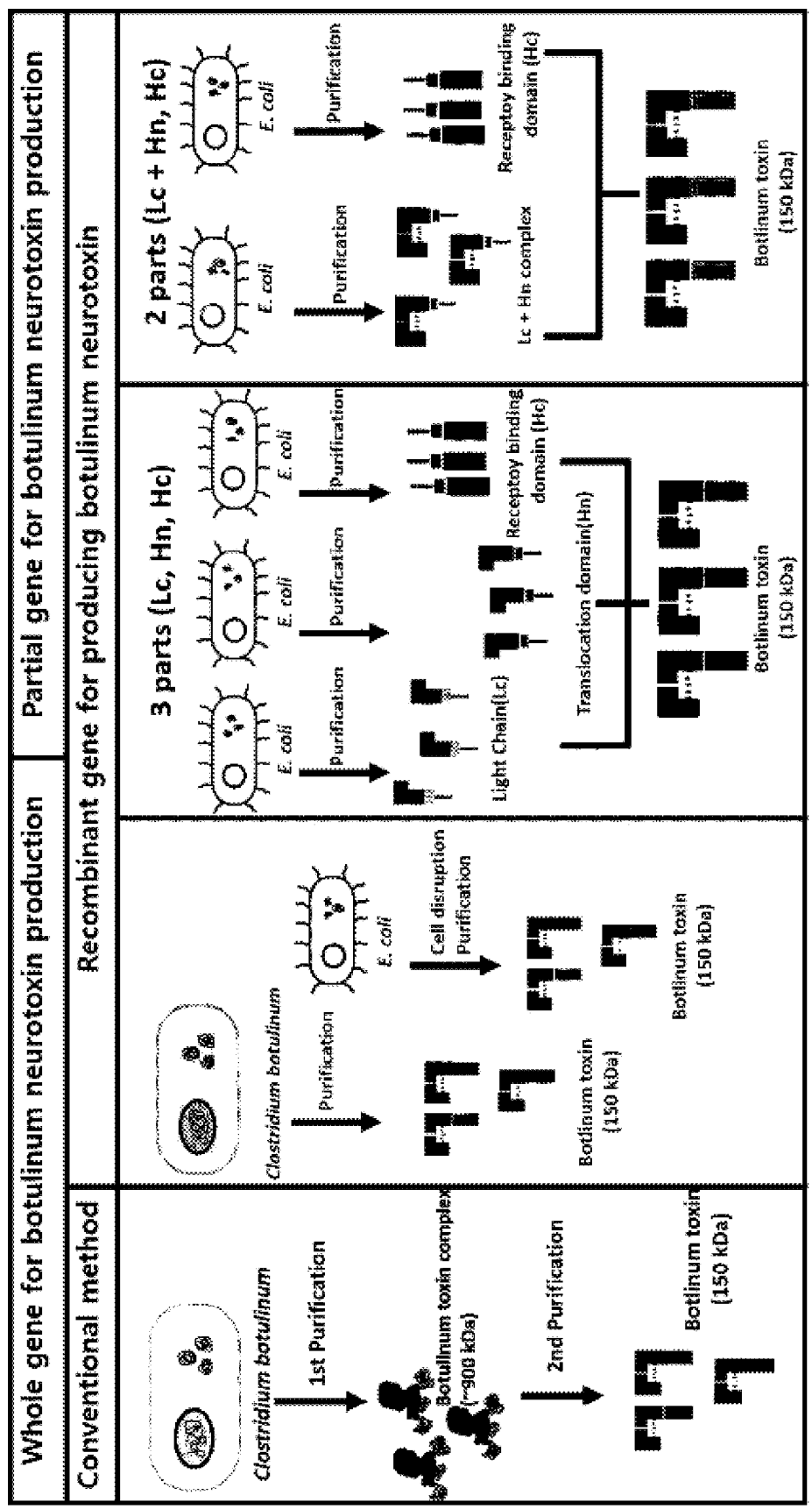
Figure 2A:
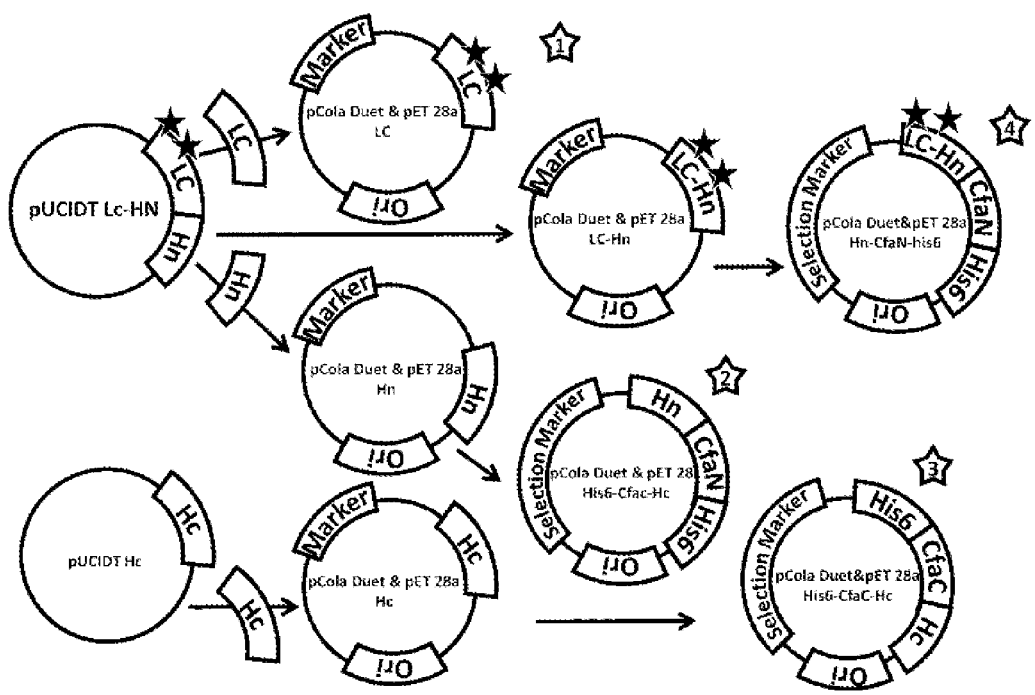
Figure 2B:
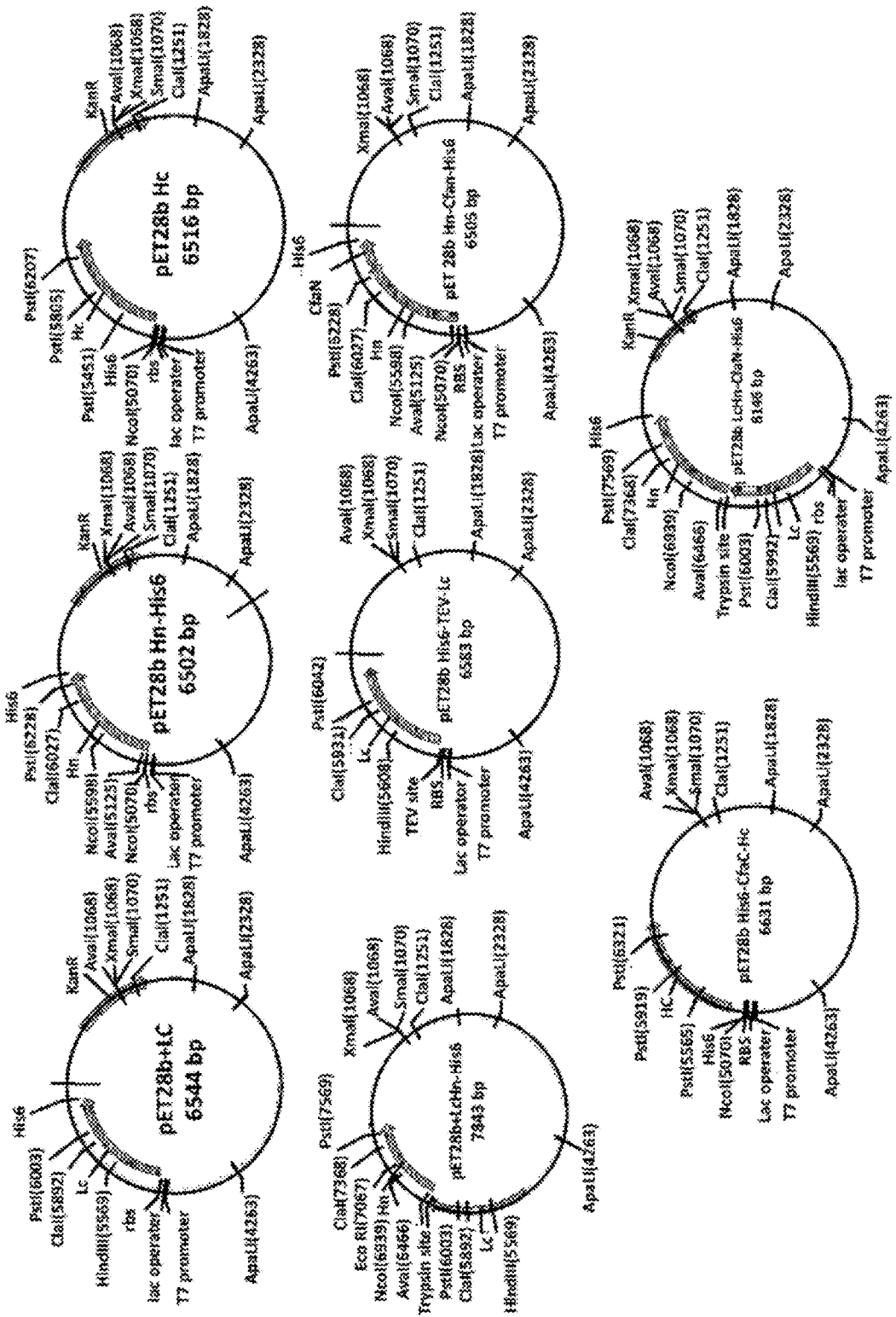
Figure 3A:
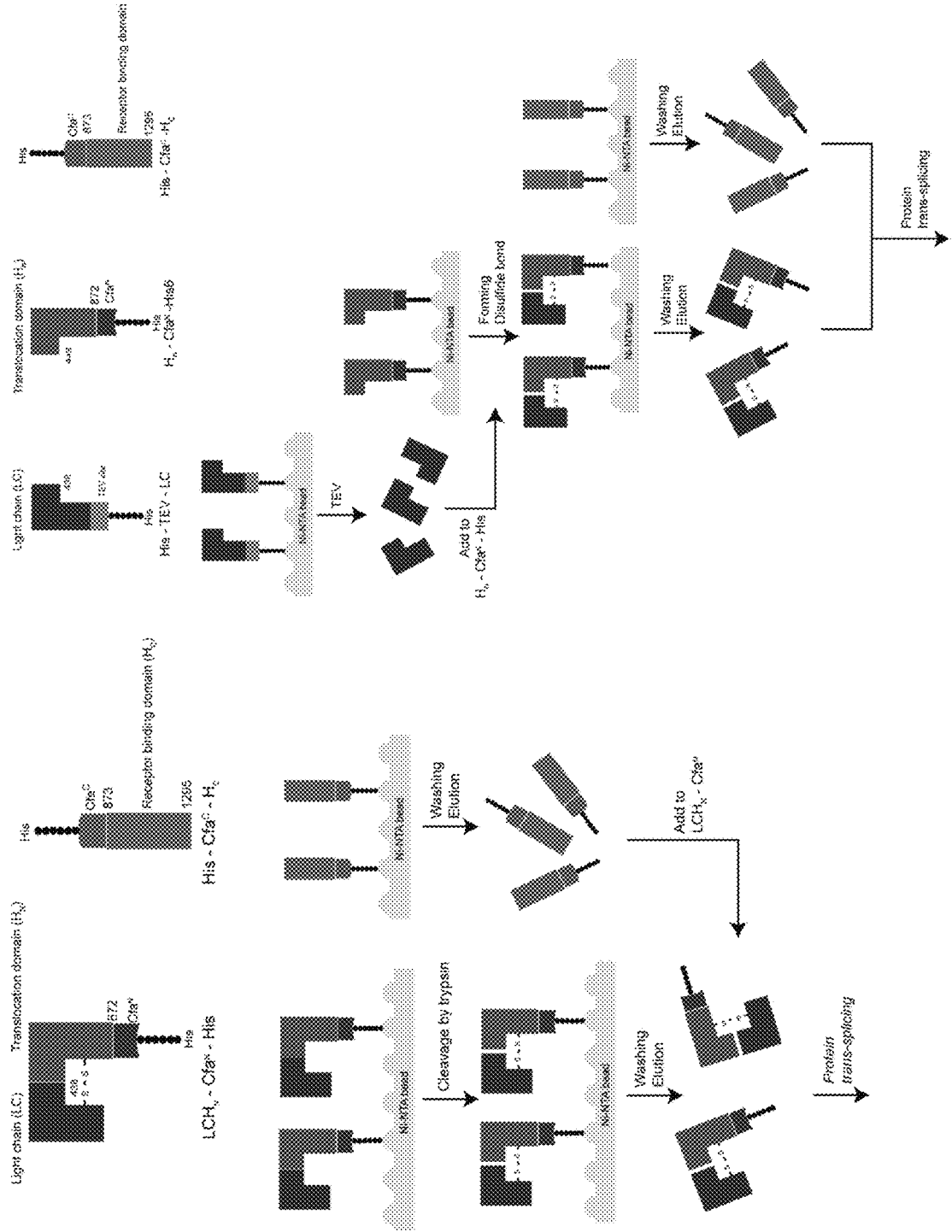

B: Comparison between a conventional process for producing botulinum toxin and a process for producing botulinum toxin fragments (two fragments/three fragments) according to the present invention;

FIG. 2 illustrates (A) a plasmid encoding fragments of botulinum toxin according to the present invention, (B) a vector map of the plasmids used in the present invention, and fragments produced using the same;

FIGS. 3a and 3b collectively illustrate a process for producing a full-length botulinum toxin using fragments of botulinum toxin according to the present invention:

Left: two-part split method, and

Figure 4:
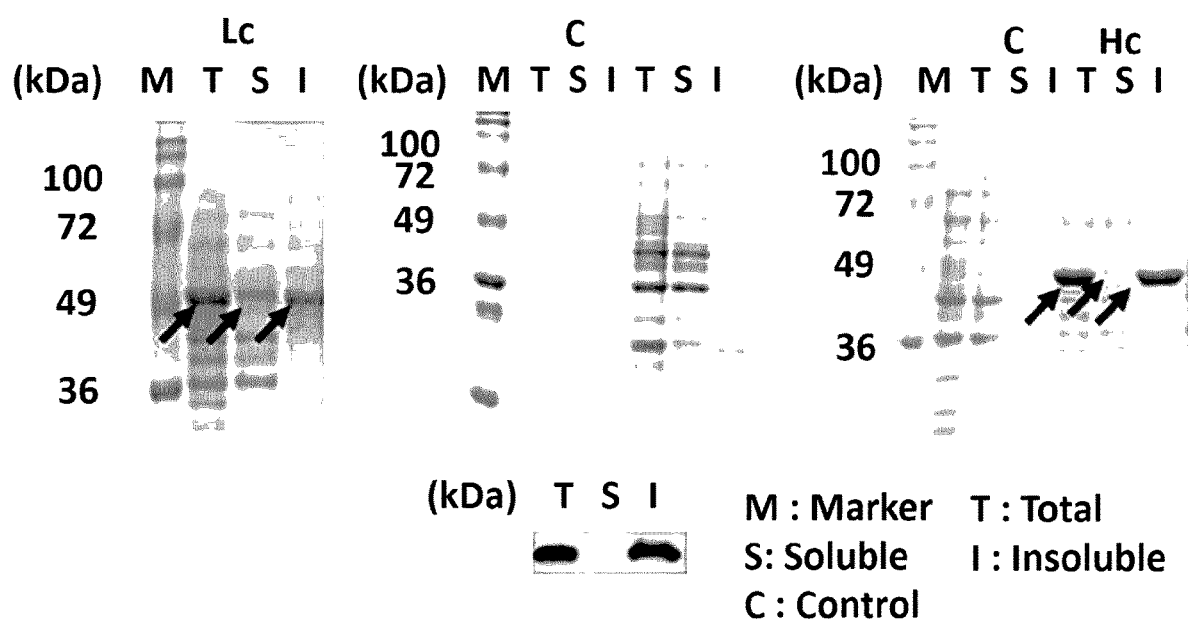
Figure 5A:
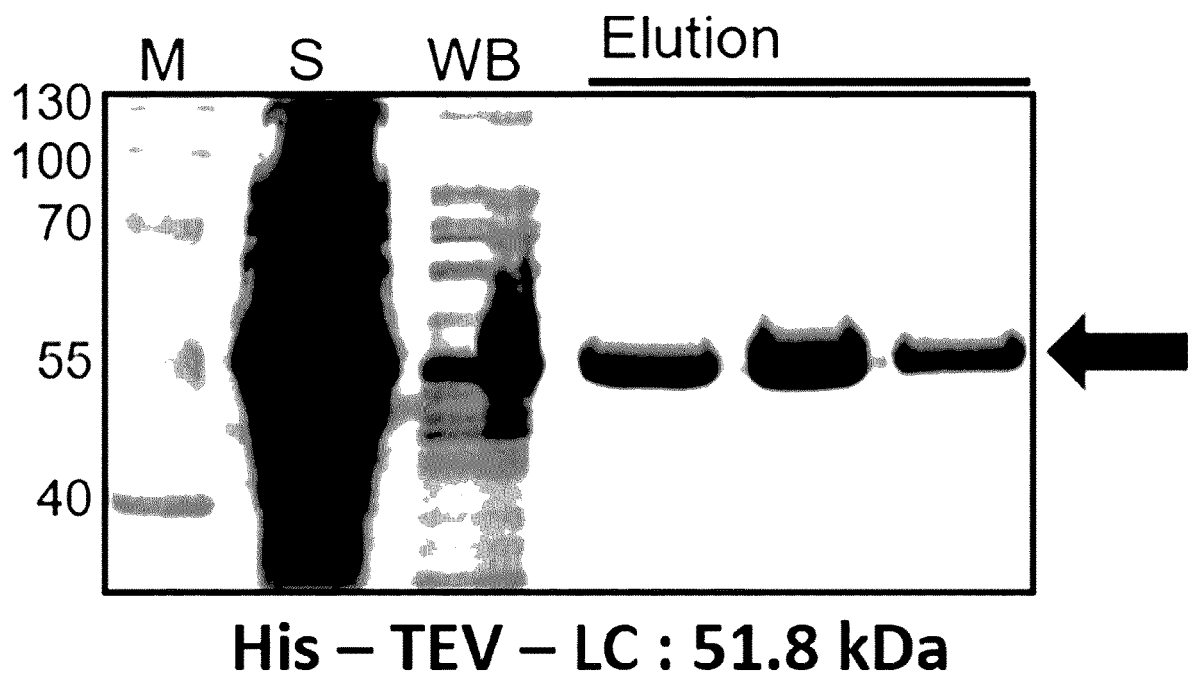
Figure 5B:
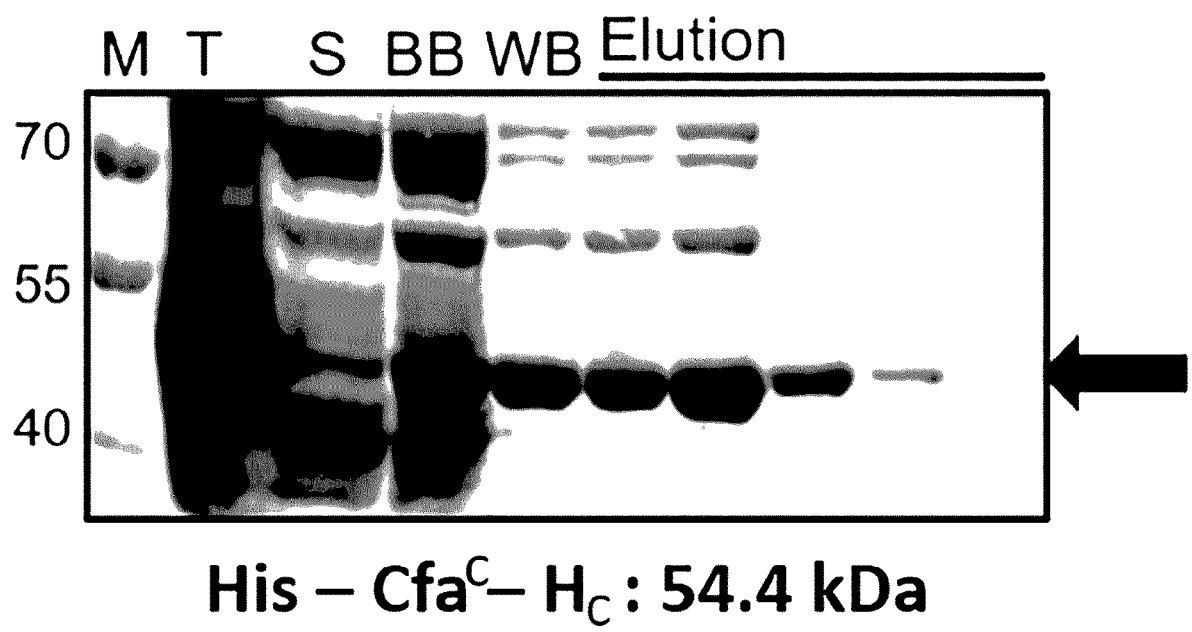
Figure 5C:
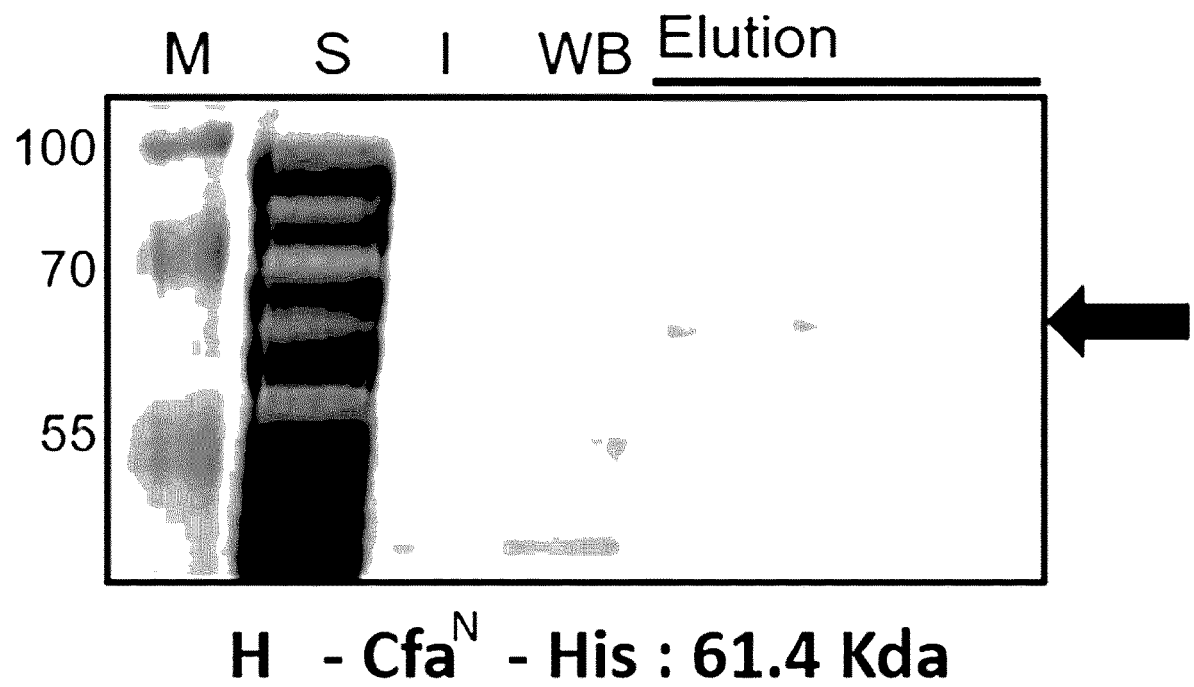
Figure 6A:
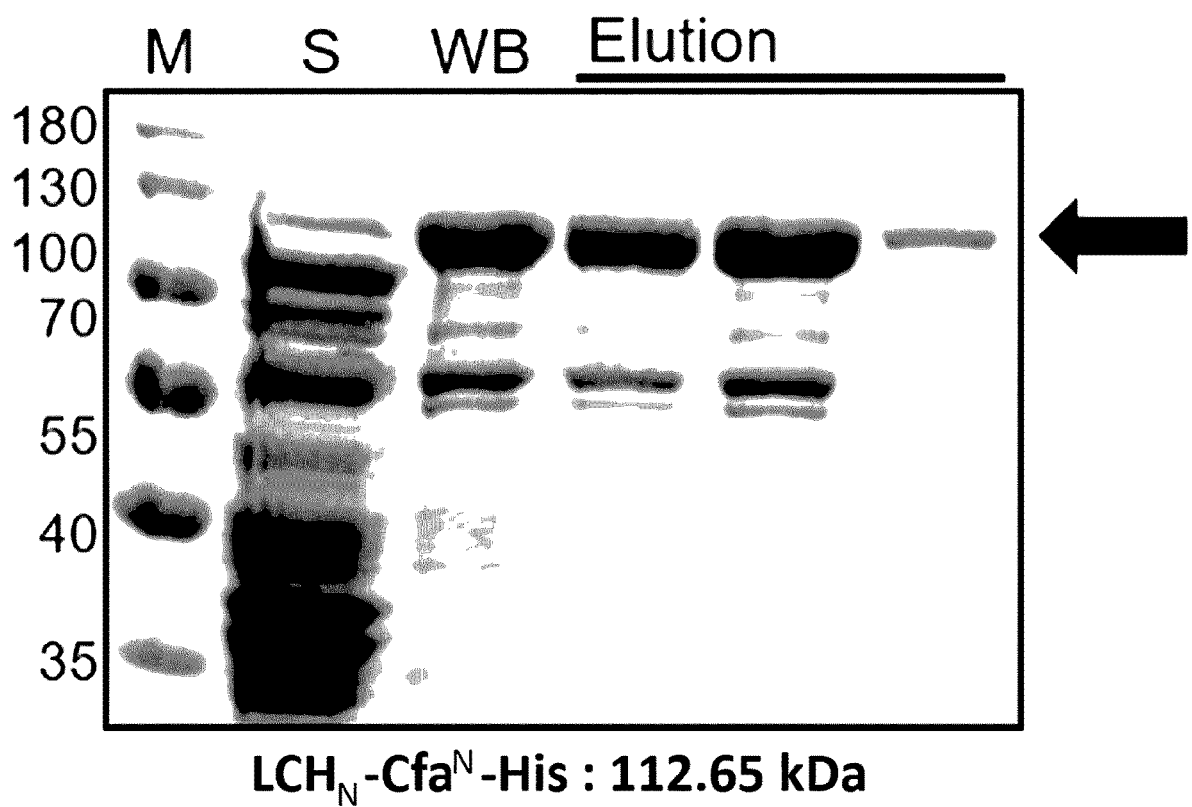
Figure 6C:
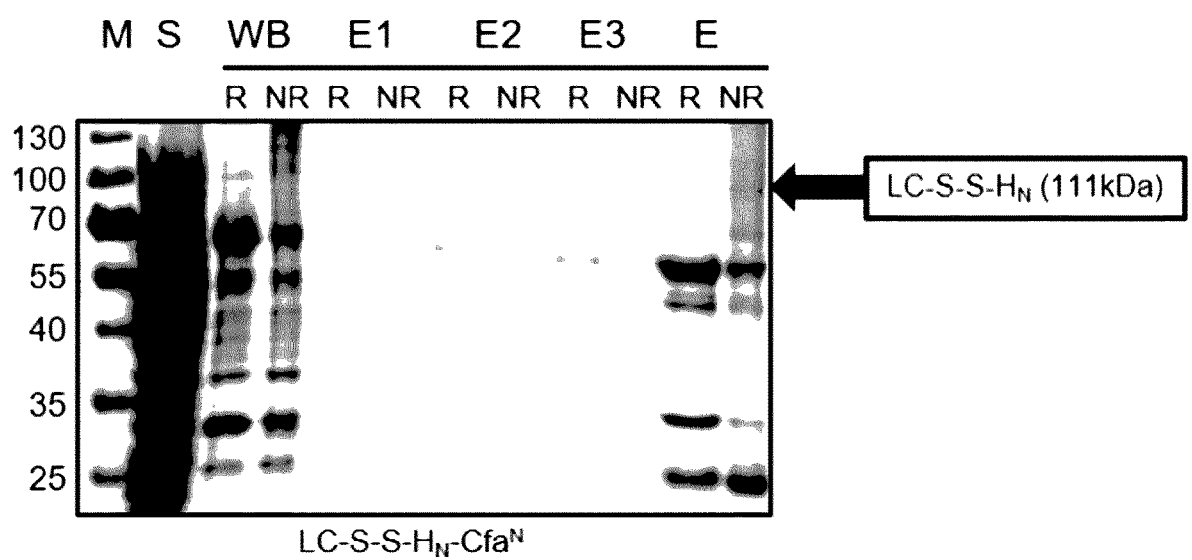
Figure 6D:
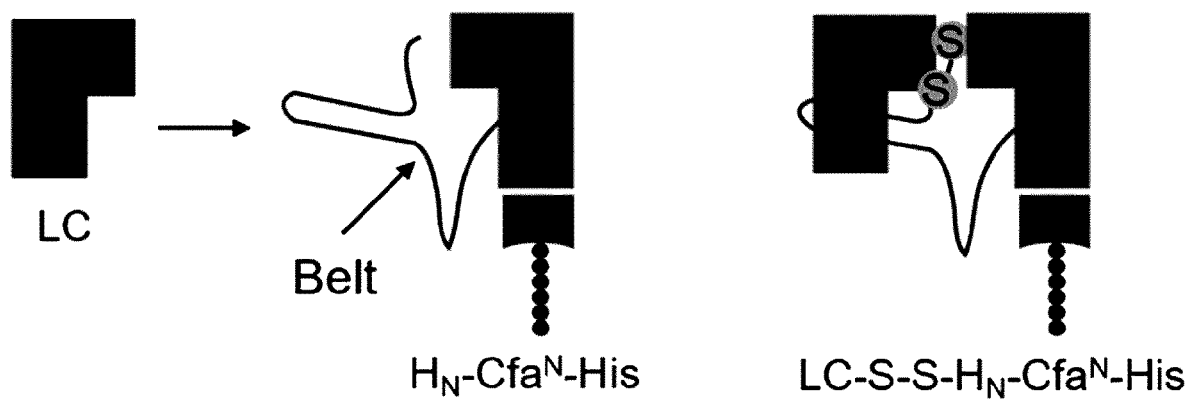
Figure 8A:
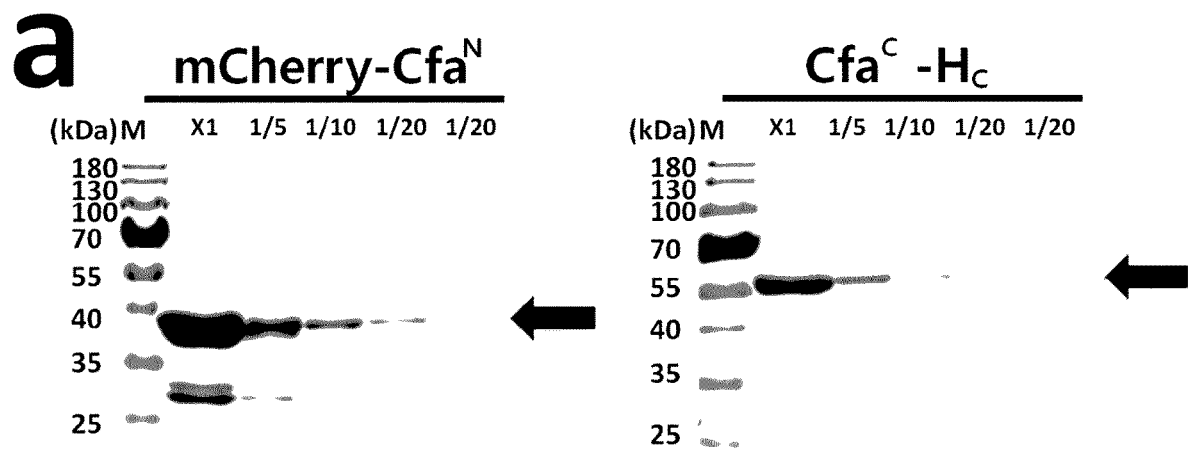
Figure 8B:
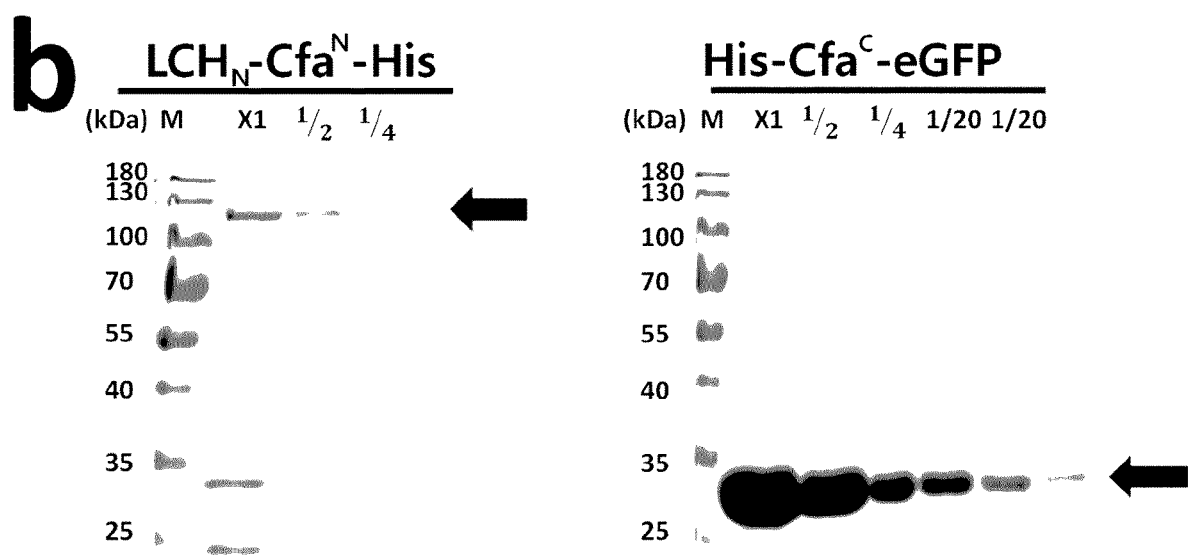
Figure 9A:
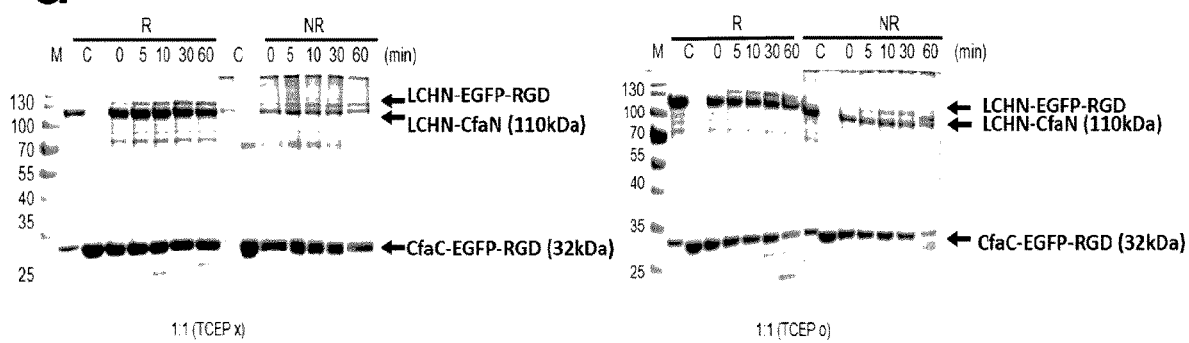
Figure 9B:
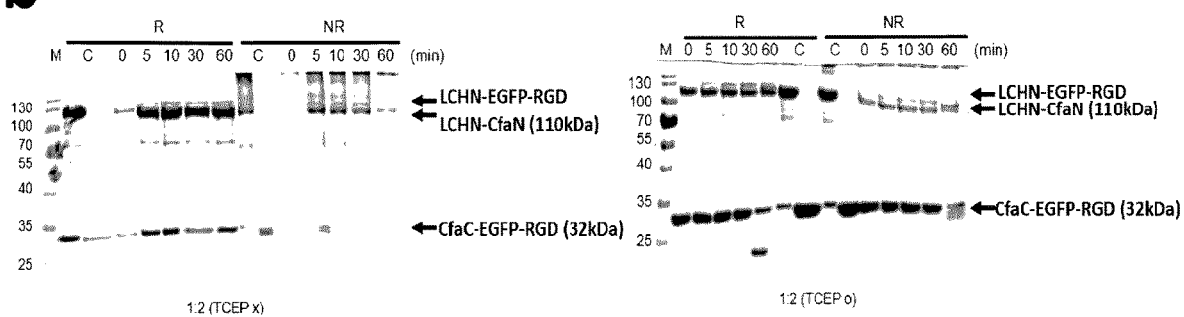
Figure 9C:
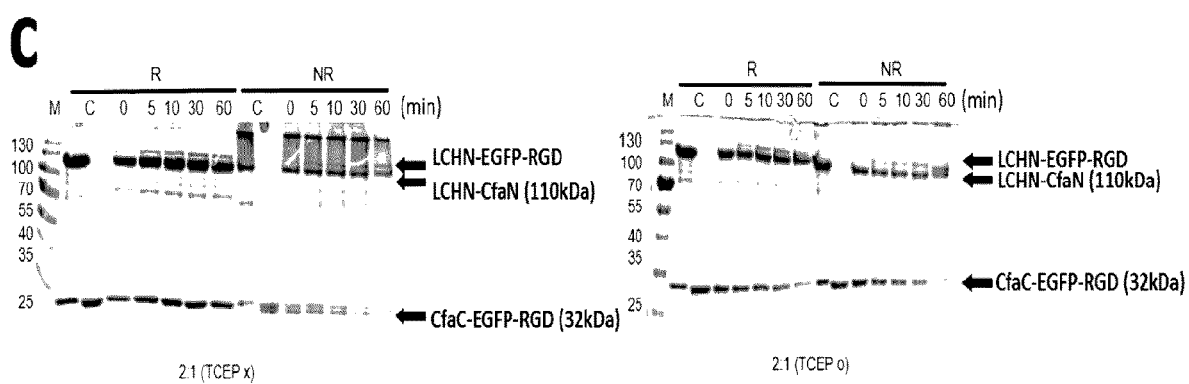
Figure 9D:
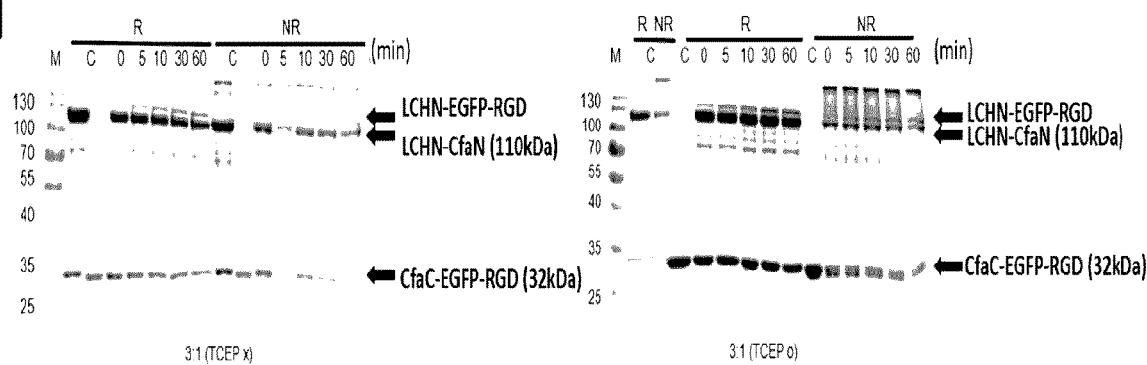
Figure 9E:
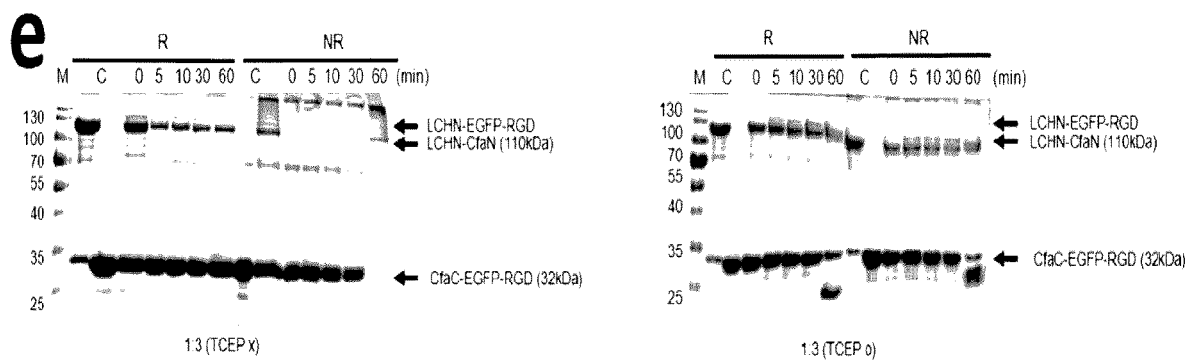
Figure 9G:
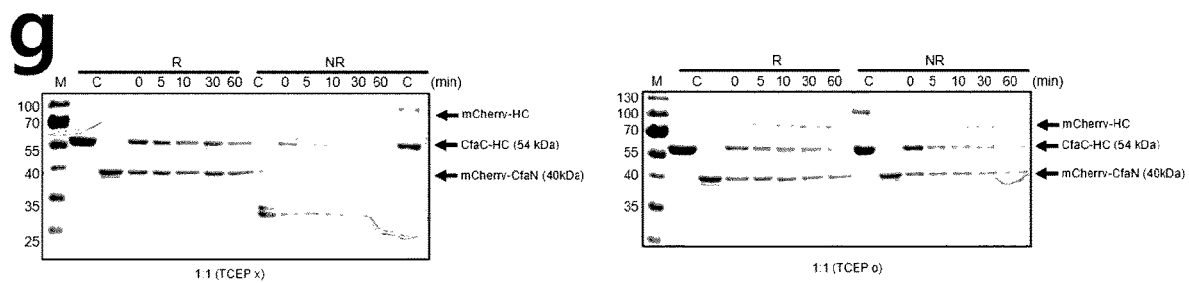
Figure 9H:
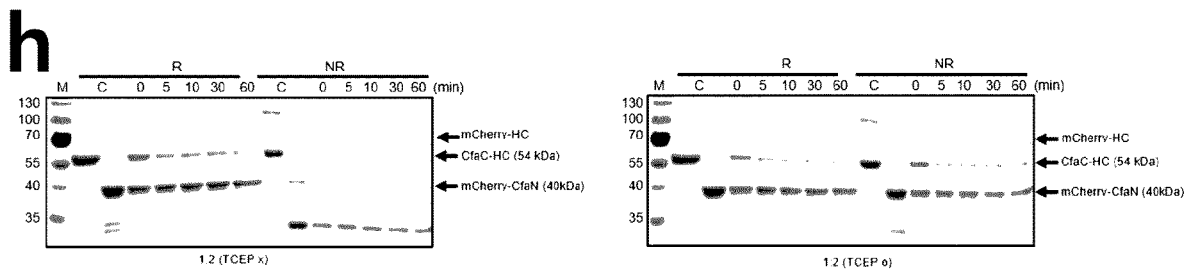
Figure 9I:
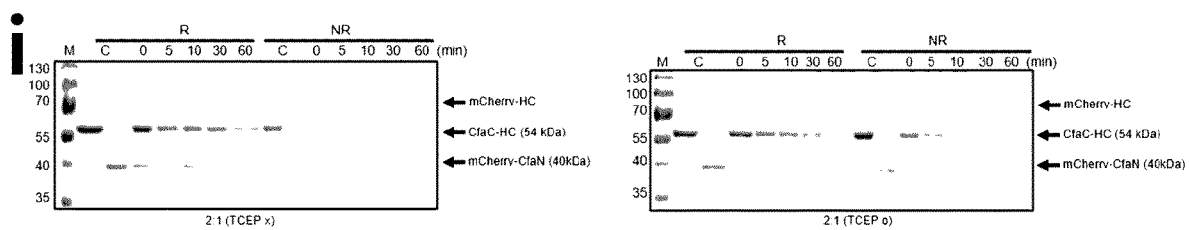

Right: three-part split method;

FIG. 4 illustrates the expression of fragments (LC, $H_N$ and $H_C$) of the botulinum toxin of the present invention in *E. coli*;

FIG. 5 illustrates soluble expression and purification of botulinum toxin fragments (TEV-LC, $Cfa^C$-$H_C$, and $H_N$-$Cfa^N$ that can be assembled into a full length toxin) of the present invention in *E. coli*;

Figure 6B:
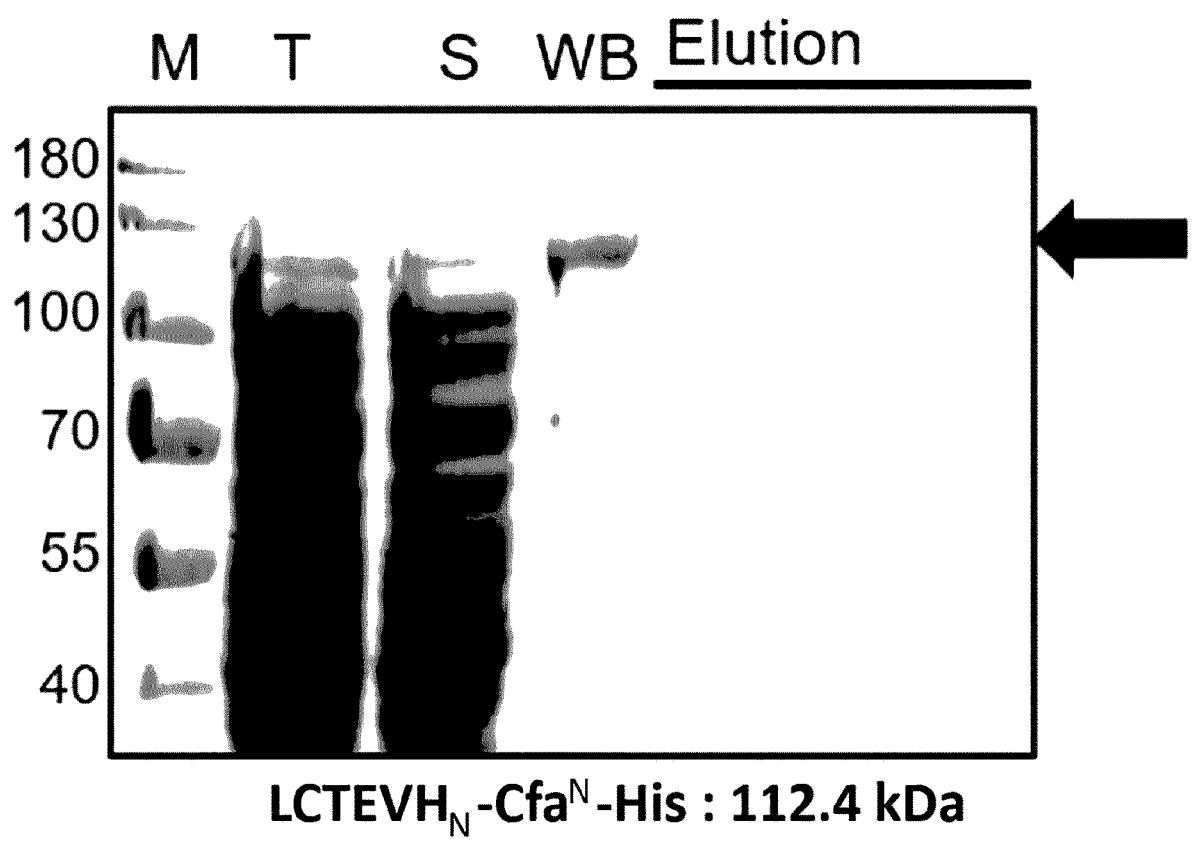

FIG. 6 illustrates soluble expression and purification of two-part split fragments (three types of fragments, LC-$H_N$-$Cfa^N$, which may be assembled into a full length toxin) of the botulinum toxin according to the present invention in *E. coli* and the principle whereby LC-S-S-$H_N$-$Cfa^N$ is formed;

FIG. 7 illustrates assembly of the split fragments into a full-length toxin again;

FIG. 8 illustrates soluble expression and purification in *E. coli* of a surrogate model replacing the botulinum split fragment to identify trans-intein splicing;

FIG. 9 illustrates a comparison of the protein trans-splicing reaction between inteins depending on reducing conditions and the use of a reducing agent at each of molar concentration ratios set between split fragments of botulinum toxin of the present invention and the surrogate model; and FIG. 10 illustrates the results of an identification as to whether or not the light chain used in the present invention has an activity of cleaving the SNAP-25 protein.

BEST MODE

Hereinafter, the present invention will be described in detail with reference to exemplary embodiments. However, the exemplary embodiments are provided merely for illustration of the present invention. Detailed descriptions of technologies and configurations well-known to those skilled in the art will be omitted when they may obscure the subject matter of the present invention, and are not intended to limit the invention. Various modifications and applications of the present invention are possible within the scope of the claims described later and equivalents derived therefrom.

In addition, the terminology used herein is used to accurately describe preferred embodiments, and may be changed according to intentions or customs of users or operators. Accordingly, the definitions of the terminology should be understood based on the content throughout the specification. It will be further understood that terms "comprises", "has", and the like, when used in this specification, specify the presence of other components, but do not preclude the presence or addition of other components unless otherwise mentioned.

Unless otherwise defined, all technical terms used herein have the same meanings as generally understood by those skilled in the art to which the present invention pertains. In addition, preferred methods and samples described herein and equivalents thereto fall within the scope of the present invention. The disclosures of all publications herein mentioned by reference are incorporated herein in their entireties.

In one aspect, the present invention is directed to a plasmid for producing botulinum toxin, the plasmid encoding fragments of botulinum toxin.

In one embodiment, the fragment of botulinum toxin may be a light chain (LC), a translocation domain of a heavy chain ($H_N$), a complex of a light chain and a translocation domain of the heavy chain (LC-$H_N$), or a receptor-binding domain of the heavy chain (RBD or $H_C$).

In one embodiment, the botulinum toxin may include botulinum neurotoxin A, B, C, D, E, F, or G, and more preferably type A2 botulinum neurotoxin. In one embodiment of the present invention, botulinum neurotoxin type A Q45894 is used, but it is applicable to all of the various types of botulinum neurotoxin.

In one embodiment, the light chain (LC) of botulinum toxin may include the amino acid sequence of SEQ ID NO: 1, the heavy-chain receptor-binding domain (RBD or $H_C$) of the botulinum toxin may include the amino acid sequence of SEQ ID NO: 2, and the heavy-chain translocation domain ($H_N$) of the botulinum toxin may include the amino acid sequence of SEQ ID NO: 3.

The light chain (LC) of the botulinum toxin of the present invention is a metalloprotease having an active site embedded in the center of the structure thereof, and the metalloprotease contains $Zn^{2+}$ coordinated by the HExxH motif and thus activity of recognizing and cleaving SNARE proteins such as VAMP/synaptobrevin, SNAP-25, and syntaxin (Chiavo et al., 1992b,c).

The heavy chain (HC) of the botulinum toxin of the present invention has a size of about 100 kDa, forms a full-length toxin through a disulfide bond with the light chain, and selectively binds to a high-affinity receptor on the synaptic membrane of the cholinergic neuron to allow the toxin to enter the neuron via endocytosis. The heavy chain is divided into two 50 kDa domains, namely a translocation domain ($H_N$) and a receptor-binding domain ($H_C$).

The $H_N$ domain of the botulinum toxin of the present invention, which is called a "translocation domain", translocates the light chain across the intracellular vesicle membrane into the cytosol, and the $H_C$ domain strongly binds the toxin to the cholinergic nerve terminals (Dolly et al. al., 1984; Binz and Rummel, 2009; Rossetto et al., 2014).

The fragments of the botulinum toxin of the present invention are non-toxic and are capable of overcoming the problems of high complexity, low safety, and low economic feasibility of conventional botulinum toxin production and manufacturing methods.

In another aspect, the present invention is directed to a host cell transformed with the plasmid of the present invention.

In one embodiment, the host cell may be *E. coli*.

As used herein, the term "host cell" refers to a eukaryotic or prokaryotic cell introduced with one or more DNA or vectors, and should be understood to encompass not only a particular target cell, but also the progeny or potential progeny thereof. In fact, the progeny may not be identical to the parent cell, as certain modifications may occur in subsequent generations due to mutations or environmental factors, but still falls within the definition of the term as used herein.

Although soluble expression of light chains has often been reported in the prior art, it has not been possible to express soluble heavy chains. Therefore, heavy chains conventionally need to be reproduced through a refolding process and further stabilized through addition of a surfactant. The refolding process is slow and has very low yield, and the heavy chain thus produced must form a disulfide bond with the light chain so as to produce a full-length toxin. The process of forming the disulfide bond is also slow and inaccurate. Botulinum toxin has several cysteine residues that hinder the correct formation of disulfide bonds, so an additional process for purifying the full-length toxin, which is produced slowly at very low yield, is required. Therefore, the present invention proposes a method of producing soluble toxin fragments in recombinant $E.$ $coli$ by splitting the toxin into two parts (called "two-part split method"), namely, the protein complex "LC-$H_N$", in which the light chain is combined with the translocation domain ($H_N$) of the heavy chain of the botulinum toxin, as one fragment (first fragment), and the receptor-binding domain (RBD, $H_C$) of the heavy chain, as the other fragment (second fragment). By devising a method for separately purifying LC, $H_N$, and $H_C$ and then producing a full-length toxin through reconjugation (called "three-part split method"), it was possible to avoid the use of protease. In addition, in order to simultaneously realize the advantages of the two-part split method and the three-part split method, LC and $H_N$ are co-expressed in the same strain using a duet vector, so expression can be realized in the state in which the cleavage site of LC-S—S-$H_N$ (a two-fragment complex protein in which LC and $H_N$ are linked through a disulfide bond) is removed so as to naturally form a disulfide bond. This obviates the process of cleaving LC-$H_N$ using a protease.

In the present invention, the two-part split method achieves conjugation between LC-$H_N$-$Cfa^N$ and $Cfa^C$-$H_C$ using protein trans-splicing between $Cfa^N$ and $Cfa^C$, which are inteins attached respectively thereto. The method is capable of producing an intact botulinum neurotoxin by removing the cleavage site between LC-$H_N$-$Cfa^N$ using trypsin, etc. to activate the toxin, removing the enzyme, performing elution, purifying $Cfa^C$-$H_C$, and then adding the same to a solution containing LC-$H_N$-$Cfa^N$ and $Cfa^C$-$H_C$ to allow protein trans-splicing to occur. In the present invention, Cfa intein was used for protein trans-splicing, but the present invention is not limited thereto.

In the present invention, the three-part split method includes separately producing TEV-LC, $Cfa^C$-$H_C$, and $H_N$-$Cfa^N$, followed by assembly. Specifically, the method is capable of producing an intact botulinum neurotoxin by first inducing disulfide bonds between TEV-LC and $H_N$-$Cfa^N$ to form LC-$H_N$, purifying the same along with $Cfa^C$-$H_C$, and then mixing a solution containing LC-$H_N$-$Cfa^N$ with a solution containing $Cfa^C H_C$, to allow protein trans-splicing to occur. In this case, production of the LC-S-S-$H_N$ complex can be induced by co-expression of LC and $H_N$ in one cell using the duet vector.

In another aspect, the present is directed to a fragment of botulinum toxin produced using the plasmid for producing botulinum toxin.

In one embodiment, the fragment of botulinum toxin may be a light chain (LC), a translocation domain of a heavy chain ($H_N$), a complex of a light chain and a translocation domain of the heavy chain (LC-$H_N$), or a receptor-binding domain of the heavy chain ($H_C$). The enzymatic cleavage site between the light chain and the heavy chain may be a site cleaved by a specific enzyme such as TEV or a trypsin cleavage site, an intein, affinity tag or sortase-recognition sequence may be added to the fragment.

In another aspect, the present invention is directed to a full-length botulinum toxin produced by mixing the fragments of botulinum toxin.

In one embodiment, the full-length botulinum toxin can be produced by mixing the fragments of botulinum toxin, that is, mixing the light chain (LC), the translocation domain of the heavy chain ($H_N$), and the receptor-binding domain of the heavy chain ($H_C$), or mixing the complex of the light chain and the translocation domain of the heavy chain (LC-$H_N$) with the receptor-binding domain of the heavy chain ($H_C$).

In one embodiment, the full-length botulinum toxin can be assembled by forming disulfide bonds between the fragments of the botulinum toxin.

In one embodiment, the botulinum toxin may be dimer botulinum toxin.

In one embodiment, the botulinum toxin may be used for the treatment of neuropathic pain disorders, ophthalmic disorders, motor disturbance, otolaryngological disorders, gastrointestinal disorders, genitourinary disorders, dermatological disorders, pain disorders, inflammatory disorders, secretion disorders, respiratory disorders, hypertrophic disorders, joint disorders, endocrine disorders, autoimmune diseases, proliferative diseases and traumatic injuries, or for veterinary application.

In another aspect, the present invention is directed to a pharmaceutical composition for ameliorating or treating a neurological disease containing the botulinum toxin as an active ingredient.

In one embodiment, the neurological disease may be cranial neuropathy, blepharospasm, strabismus, hyperhidrosis, torticollis, neck pain, polio, facial spasm, epigenetic neuralgia, diabetic neuropathy, complex regional pain syndrome, trigeminal neuralgia, phantom limb pain, spinal cord injury-induced neuropathic pain, post-central stroke pain, or a veterinary neuropathic disease.

The botulinum toxin according to the present invention may be used in the form of a salt, preferably a pharmaceutically acceptable salt. The salt is preferably an acid addition salt produced from a pharmaceutically acceptable free acid, and an organic acid and an inorganic acid may be used as the free acid. The organic acid includes, but is not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. In addition, the inorganic acid includes, but is not limited to, hydrochloric acid, hydrobromic acid, sulfuric acid and phosphoric acid.

The pharmaceutical composition of the present invention may further include an adjuvant. Any adjuvant can be used without limitation, as long as it is known in the art. For example, the pharmaceutical composition may further include Freund's complete or incomplete adjuvant to increase immunity.

As used herein, the term "treatment" means that the disease or condition to which the term applies, or one or more symptoms of the disease or condition, is reversed or ameliorated, or that the progression thereof is inhibited or prevented, unless otherwise stated.

As used herein, the term "mammal" refers to a mammal that is the subject on which treatment, observation or experimentation is performed, preferably a human.

As long as a recipient animal is capable of tolerating administration of the composition, or administration of the composition thereto is suitable, the composition is said to be "pharmaceutically or physiologically acceptable". When the amount of the composition that is administered is physiologically important, the composition can be said to be administered in a "therapeutically effective amount". The composition is physiologically meaningful if the presence of the composition results in a physiologically detectable change in the recipient patient.

The therapeutically effective amount of the composition of the present invention may vary depending on several factors, for example, the administration method, the target site, the condition of the patient, and the like. Therefore, when used in the human body, the dosage should be determined in an appropriate amount in consideration of both safety and efficiency. The effective amount for use in humans may be estimated from the effective amount determined through animal experimentation. The considerations required for determining the effective amount are described, for example, in Hardman and Limbird, eds., Goodman and Gilman's The Pharmacological Basis of Therapeutics, 10th ed. 2001), Pergamon Press; and E. W. Martin ed., Remington's Pharmaceutical Sciences, 18th ed. (1990), Mack Publishing Co.

The pharmaceutical composition of the present invention may be administered in a pharmaceutically effective amount. The term "pharmaceutically effective amount" used herein means an amount sufficient to treat or prevent a disease at a reasonable benefit/risk ratio applicable to pharmaceutical (medical) treatment, while causing no side effects. The effective amount is determined depending on factors including state of health of the patient, disease type, severity, drug activity, drug sensitivity, administration method, administration time, administration route and excretion rate, treatment period, drugs used in combination with or concurrently with the composition of the present invention, and other factors well known in the pharmaceutical field. The pharmaceutical composition of the present invention may be administered as a single therapeutic agent or in combination with other therapeutic agents, sequentially or simultaneously with conventional therapeutic agents, and in single or multiple doses. Taking into consideration these factors, it is important to administer the composition in the minimum amount sufficient to achieve maximum efficacy without side effects, which can be easily determined by those skilled in the art.

The composition of the present invention may further contain a carrier, diluent, or excipient commonly used in biological agents, or a combination of two or more thereof. Any pharmaceutically acceptable carrier may be used without particular limitation, as long as it is suitable for in-vivo delivery of the composition. For example, the pharmaceutically acceptable carrier may be a compound, saline, sterile water, Ringer's solution, buffered saline, dextrose solution, maltodextrin solution, glycerol, ethanol, and combinations of two or more of these components described in Merck Index, 13th ed., Merck & Co. Inc. If necessary, other ordinary additives such as antioxidants, buffers, and bacteriostats may be added. In addition, the composition may be prepared into an injectable formulation such as an aqueous solution, suspension, or emulsion, pill, capsule, granule, or tablet by further adding a diluent, dispersant, surfactant, binder, or lubricant thereto. Furthermore, the composition can be preferably formulated according to the corresponding disease or components using an appropriate method in the art or a method disclosed in Remington's Pharmaceutical Science (Mack Publishing Company, Easton PA, 18$^{th}$, 1990).

The pharmaceutical composition of the present invention may be used as an oral formulation such as a powder, granule, tablet, capsule, suspension, emulsion, syrup, or aerosol, an external preparation, suppository, or sterile injection solution prepared according to a conventional method.

As used herein, the term "pharmaceutically acceptable" means a property of being non-toxic to cells or humans exposed to the composition.

The pharmaceutical composition of the present invention may further contain a pharmaceutically acceptable additive. Useful pharmaceutically acceptable additives include starch, gelatinized starch, microcrystalline cellulose, lactose, povidone, colloidal silicon dioxide, calcium hydrogen phosphate, lactose, mannitol, syrup, gum arabic, pregelatinized starch, corn starch, powdered cellulose, hydroxypropyl cellulose, Opadry, sodium starch glycolate, lead carnauba, synthetic aluminum silicate, stearic acid, magnesium stearate, aluminum stearate, calcium stearate, sucrose, dextrose, sorbitol, talc, and the like. The pharmaceutically acceptable additive according to the present invention is preferably present in an amount of 0.1 to 90 parts by weight based on the weight of the composition, but is not limited thereto.

As used herein, the term "administration" means providing a predetermined substance to a patient using any suitable method, and may be classified into parenteral administration (e.g., using an intravenous, subcutaneous, intraperitoneal, or topical injection formulation) and oral administration, depending on the intended method, and the dosage greatly varies according to the patient's weight, age, gender, state of health, diet, administration time, administration method, excretion rate, and severity of disease.

The composition of the present invention may be administered parenterally (for example, intravenously, subcutaneously, intraperitoneally, or topically) or orally depending on the desired method, and the dosage may be determined in consideration of the age, weight, gender, physical condition and the like of the subject. It is obvious that the concentration of the active ingredient in the pharmaceutical composition may vary depending on the subject, and the active ingredient is preferably present at a concentration of 0.01 to 5,000 µg/ml in the pharmaceutical composition. If the concentration is less than 0.01 µg/ml, pharmaceutical activity is not obtained, and if the concentration is higher than 5,000 µg/ml, toxicity to the human body occurs.

The pharmaceutical composition of the present invention may be formulated in various oral or parenteral dosage forms. Formulations for oral administration include, for example, tablets, pills, hard and soft capsules, liquids/solutions, suspensions, emulsifiers, syrups, and granules. Each of these formulations may further contain, in addition to the active ingredient, a diluent (e.g., lactose, dextrose, sucrose, mannitol, sorbitol, cellulose, and/or glycine), and a lubricant (e.g., silica, talc, stearic acid, a magnesium or calcium salt thereof, and/or polyethylene glycol). In addition, the tablet may contain a binder such as magnesium aluminum silicate, starch paste, gelatin, tragacanth, methylcellulose, sodium carboxymethylcellulose, and/or polyvinylpyrrolidine, and may optionally contain a disintegrant such as starch, agar, alginic acid or sodium salts thereof, or an effervescent mixture, and/or an absorbent, coloring agent, flavoring agent and sweetener. The formulation may be prepared using conventional mixing, granulating or coating methods. In addition, representative formulations for parenteral administration are preparations for injection, and a solvent for such a preparation for injection may be water, Ringer's solution, isotonic saline, or suspension. The sterile, immobilized oil of the preparation for injection may be used as a solvent or suspending medium, and any non-irritating immobilized oil including mono- and di-glycerides can be used for this purpose. In addition, the preparation for injection may include a fatty acid such as oleic acid.

In another aspect, the present invention is directed to a method of producing botulinum toxin, including separately producing fragments of botulinum toxin, namely a light chain (LC), a translocation domain of a heavy chain ($H_N$), and a receptor-binding domain of the heavy chain ($H_C$), and mixing the light chain (LC), the translocation domain of the heavy chain ($H_N$), and the receptor-binding domain of the heavy chain ($H_C$) to produce full-length botulinum toxin.

In another aspect, the present invention is directed to a method of producing botulinum toxin including separately producing fragments of botulinum toxin, namely a complex of a light chain and a translocation domain of the heavy chain (LC-$H_N$), and a receptor-binding domain of the heavy chain ($H_C$), cleaving the complex (LC-$H_N$) into the light chain (LC) and the translocation domain of the heavy chain ($H_N$), and mixing the light chain (LC), the translocation domain of the heavy chain ($H_N$), and the receptor-binding domain of the heavy chain ($H_C$) to produce full-length botulinum toxin.

In one embodiment, the botulinum toxin can be produced by conjugating fragments of botulinum toxin through trans-splicing, non-covalent affinity bonds such as coiled coils shown in Tables 1 and 2 below, non-covalent bonds, or sortase-mediated ligation.

In one embodiment, fragments of the botulinum toxin of the present invention can be reconjugated (covalently bonded) into full-length botulinum toxin using the following method:

1) Protein binding via soltase A: this is an irreversible binding reaction via soltase A, which is a transpeptidase derived from bacteria, wherein soltase A recognizes the specific amino acid sequence of LPXTG, cleaves threonine and glycine from each other, and binds the same to the cell surface. This is a useful method widely used in protein engineering and easily forms a desired bond by adding an LPXTG sequence and two or more consecutive glycine sequences to two proteins to be bound. The soltase applied to protein engineering may be derived from *Sulfobacillus, Rubrobacter, Peptoniphilus, Shewanella, Faecalibaculum, Colwellia, Staphylococcus, Methylorubrum, Gaiella, Bacillus, Clostridium, Blautia, Enterococcus, Streptococcus, Streptomyces, Lactobacillus, Listeria, Pediococcus* or *Corynebacterium*, but is not limited thereto.

2) Trans-intein splicing: protein domains or peptide fragments necessary for linking to the C-terminus and N-terminus of the membrane-structured protein were added along with a linker. The protein domains used herein were trans-inteins, which are of type DnaE or DnaB as set forth in Tables 3 and 4 below, such as Cfa, Npu, Ssp, Rma, and Ppu, but are not limited thereto. These trans-inteins are expressed in separate forms when expressed. However, after the N-terminal domain (Int-C) binds to the C-terminal domain (Int-N) to form a complete intein conjugate, the intein conjugate is spliced and separated. At this time, the extein domains outside the intein conjugate are linked through peptide bonds to form a single protein.

TABLE 3

| Name | Domain | Sequence | Remarks | Sequence No. |
|---|---|---|---|---|
| Cfa | Int-N | CLSYDTEILTVEYGFLPIGKIVEERIECTVYTVDKNGFVYTQPI-AQWHNRGQEV FEYCLEDGSIIRATKDHKFMTTDGQMLPIDEIFERGLDLKQVDGLP | | 13 |
| | Int-C | MVKIISRKSLGTQNVYDIGVEKDHNFLLKNGLVASNCFN | | 14 |
| Npu | Int-N | AEYCLSYETEILTVEYGLLPIGKIVEKRIECTVYSVDNNG-NYTQPVAQWHDRGE QEVFEYCLEDGSLIRATKDHKFMTVDGQMLPIDEIFERELDLMRVDNLPN | DnaE | 15 |
| | Int-C | MIKIATRKYLGKQNVYDIGVERDHNFALKNGFIASN | | 16 |
| Ssp | Int-N | AEYCLSFGTEILTVEYGPLPIGKIVSEEINCSVYSVDPEGRVYTQA-IAQWHDRG EQEVLEYELEDGSVIRATSDHRLFLTTDYQLLAIEVFARQLDLLTLENIKQ-TEE ALDNHRLPFPLLDAGTIK | DnaE | 17 |
| | Int-C | MVKVIGRRSLGVQRIFDIGLPQDHNFLLANGAIAAN | | 18 |
| Rma | Int-N | CLAGDTLITLADGRRVPIRELVSQQNFSVWALNPQTYRLER-ARVSRAFCTGIKP VYRLTTRLGRSIRATANHRFLTPQGWKRVDELQPGDYLALPRRIP-TASTPTLTE AELALLGHLIGD | DnaB | 19 |
| | Int-C | WDPIVSIEPDGVEEVFDLTVPGPHNFVADNIAGNS | | 20 |
| Ppu | Int-N | CISKFSHIMWSHVSKPLFNFSIKKSHMHNGNKNIYQLLDQGEAFIS-RQDKKTTY KIRTNSEKYLELTSNHKILTLRGWQRCDQLLCNDMITTQIGFELSRKK-KYLLNC IPFSLCNFET | DnaB | 21 |
| | Int-C | LANINISNFQNVFDFAANPIPNFIANNIIVHNS | | 22 |
| Cwa | Int-N | CLSYDTEILTVEYGAMYIGKIVEENINCTVYTVDKNGFVVTQ-TIAQWHNRGEQE IFEYDLEDGSKIKATKDHKFMTIDGEMLPIDEIFEKNLDLKQVVSHPDDYLV | DnaE | 23 |
| | Int-C | MVKIIGCRSLGTQKVYDIGVEKDHNFLLANGSIASNC | | 24 |

TABLE 3-continued

| Name | Domain | Sequence | Remarks | Sequence No. |
|---|---|---|---|---|
| CraS | Int-N | CLSYETEVLTLEYGFVPIGBVNKQMVCTVFSLNDSGN-VYTQPIGQWHDRGVQDL EYCLDDGSTIRATKDHKFMTTQGEMVPIDIEEIFHQGWELVQVSGISK-LVQQRT LPFIIVDRKL | DnaE | 25 |
|  | Int-C | MVKIVSRRYLGKADVYDIGVAKDHNFIIKNGLVASNC |  | 26 |
| Csp8801 | Int-N | CLSYDTEILTVEYGAIPIGKVVEENIDCTVYTVDKNGFVVTQ-NIAQWHLRGQQE VFEYYLDDGSILRATKDHQFMTLEGEMLPIHEIFETGLELKKIKI | DnaE | 27 |
|  | Int-C | MVKIVSYRSLGKQFVYDIGVAQKHNFLLANGSIASNC |  | 28 |
| Csp0110 | Int-N | CLSYDTEILTVEYGPMPIGKIVEENINCSVYTVNKNGFVYTQ-SIAQWHHRGEQE VFEYYLEDGETIRATKDHKFMTTEGKMLPIDEIFFENNLDLKKLTV | DnaE | 29 |
|  | Int-C | MVKIIERRSLGKQNVYDIGVEKDHNFLLSNNLIASNC |  | 30 |
| Mtcht | Int-N | CLSYDTQILTVEYGAVAIGEIVEKQIECTVYSVDENGYVYTQPI-AQWHNRGEQE VFEYLLEDGATIRATKDHKFMTDEDQMLPIDQIFEQGLELKQVEVLQPVF | DnaE | 31 |
|  | Int-C | MVKIVRRQSLGVQNVYDIGVEKDHNFCLASGEIQSNC |  | 32 |
| Maec | Int-N | CLGGETLIKTEEYGLLPIAKIVSEVNCTVYTVDQNGFVYSQPISQWHER-GLQEV FEYTLENGQTIQATKDHKFMTSDGEIVLAIDTIFERGLDIKSSDFS | DnaE | 33 |
|  | Int-C | MVKIIGRQSLGRKPVYDIGVEKDHNFLLGNGLIASNC |  | 34 |
| Asp | Int-N | CLSYDTEVLTVEYGFVPIGEIVEKGIECSVFSINNNGIVYTQPI-AQWHHRGKQE VFEYCLEDGSIIKATKDHKFMTQDGKMLPIDEIFEQELDLLQVKGLPE | DnaE | 35 |
|  | Int-C | MIKIASRKFLGVENVYDIGVRRDHNFFIKNGLIASNC |  | 36 |
| Oli | Int-N | CLSYNTEVLTVEYGPLPIGKIVDEQIHCRVYSVDENGFVYTQAIAQWHDR-GYQE IFAYELADGSVIRATKDHQFMTEDGQMFPIDEIWEKGLDLKKLPTVQDL-PAAVG YTVS | DnaE | 37 |
|  | Int-C | MVKIVRRQSLGVQNVYDIGVEKDHNFCLASGEIASNC |  | 38 |
| Aov | Int-N | CLSADTEILTVEYGFLPIGEIVGKAIECRVYSVDGNGNIYTQ-SIAQWHNRGEQE VFEYTLEDGSIIRATKDHKFMTTDGEMLPIDEXFARQLDLMQVQGLM | DnaE | 39 |
|  | Int-C | MVKITARKFVGRENVYDIGVEHHHNFAIKNGLIASNC |  | 40 |
| Ter-3 | Int-N | CLTYETEIMTVEYGPLPIGKIVEYRIECTVYTVDKNCYIYTQPI-AQWHNRGMQE VYEYSLEDGTVIRATPEHKFMTEDGQMLPIDEIFERNLDLKCLGTLE | DnaE | 41 |
|  | Int-C | MVKIVSRKLAKTENVYDIGVRKDHNFVLANGLIASNC |  | 42 |
| Ssp7002 | Int-N | CLAGGTPVVTVEYGVLPIDTIVEQELLCHVYSVDAQGLI-TAQLIEQWHQRGDRL LYEYELENGQMIRATPDHRFLTTTGELLPIDEIFTQNLDLAAWAVPDSLPRTA | DnaE | 43 |
|  | Int-C | MVKIIRRKFIGHAPTYDIGLSQDHNFLLGQGLIAANC |  | 44 |
| Tvu | Int-N | CLSGETAVMTVEYGAIPIRRLVQERLICQVYSLDPQGHLVTQPI-AQWHFGQFRP VYAYQLEDGSTICATPDHRFMTTSGQMLPIEQIFREGLELWQVAIAPP-GALAQG LKPAVQMSC | DnaE | 45 |
|  | Int-C | MKIVGRRLVGWQAVYDICLAGDHNFLLANGAIAANC |  | 46 |
| Tel | Int-N | CLSGETAVMTVEYGAVPIRRLVQERLSCHVYSLDGQGHLYTQPIAQWHFQG-FRF VYEYQLEDGSTICATPDHRFMTTRGQMLPIEQIFQEGLELWQVA-IAPRQALLQG LKPAVQMSG | DnaE | 47 |
|  | Int-C | MKIVGRRLMGWQAVYDIGLAADHNFVLANGAIAANC |  | 48 |
| Sel | Int-N | CLAADTEVLTVEYGPIAIGKLVEE-NIRCQVYCCNPDGYIYSQPIGQWHQRGEQE VIEYELSDGRIIRATADHRFMTEEGEMLSLDBFERSLELKQIPTPLLA-IAQPSP LATA | DnaE | 49 |
|  | Int-C | MVKIVRRRSLGVQPVYDLGVATVHNFVLANGLVASNC |  | 50 |

TABLE 3-continued

| Name | Domain | Sequence | Remarks | Sequence No. |
|---|---|---|---|---|
| Aha | Int-N | CLSYDTEIWTVEYGAMPIGKIVEEKIESCVYTVDENGFVYTQPIAQWH-PRGQQB IEYTLEDGRKIRATKDHKMMTESGEMLPIEEIFQRELD-LKVETFHEMSLLRRGAK | DnaE | 51 |
| | Int-C | MVKIIKRQSLGRQNVYDVCVETDHNFVLANGCVASNC | | 52 |

TABLE 4

| | | |
|---|---|---|
| Gp41.1$^N$ 88 | CLDLKTQVQTPQGMKEISNIQVGDLVLSNTGYNEVLNVFPSKSKKKSYK8ITLEDGKEIICSEEHLFPTQTGEMNISGGLKEGMCLYVKE | Sequence No. 53 |
| GP41.1$^C$ 37 | MMLKKILKIEELDERELIDIEVSGNHLFYANDILTHN | Sequence No. 54 |

In an embodiment of the present invention, a full-length botulinum toxin was produced by covalent bonding through trans splicing. Specifically, respective botulinum toxin fragments were linked using a mechanism in which inteins are removed during a protein-splicing process. The consensus DnaE intein (cfa) protein used herein is a self-splicing protein that is involved in post-transcriptional autoprocessing during the splicing process, and consists of an N-terminus (Cfa$^N$) and a C-terminus (Cfa$^C$). The sequence located at each terminus thereof is called an "extein". This intein may remain naturally isolated. These N-terminal and C-terminal inteins are present separately until they meet each other in the cell. After they meet each other, they are folded, trans-spliced to conjugate exteins at the two terminus sites together (Shah, N. H et al., 2014).

A conventional method of producing botulinum toxin is performed by culturing *Clostridium botulinum* bacteria, isolating a botulinum toxin complex, and purifying the same through ion exchange chromatography, but this method is disadvantageous in that it is inefficient and thus the protein yield is low. In addition, *C. botulinum* is a spore-forming bacterium, thus requiring special culture equipment and facilities that are not required when culturing other bacteria such as *Escherichia coli*. Also, botulinum toxin is a very lethal toxin, thus requiring safety measures appropriate therefor. Accordingly, attempts have been made to produce recombinant botulinum toxin in commercial strains such as *E. coli*, but these attempts also involve neurotoxin production, thus requiring safety equipment. The method for producing botulinum toxin in recombinant *E. coli* has the following problems:

1) a problem in that it is difficult to express large 150 kDa soluble proteins in *E. coli* cells (proteins are expressed as insoluble inclusion bodies in *E. coli*);

2) a problem in that interchain and intrachain disulfide bonds are present in BoNT, whereas disulfide bonds are not formed in *E. coli* cells; and 3) a problem in that unless the light and heavy chains are cleaved accurately, an inactivated toxin is produced.

In addition, no matter what strain is used, if all toxin genes are present in one cell, the cell, when exposed to the environment or a workplace, will self-reproduce, which may cause environmental pollution and fatal problems. For example, *Clostridium botulinum* is an anaerobic bacterium, but produces spores and propagates in the air, and does not die for a long time, whereas *Escherichia coli* is much more unsuitable as a production strain in that it grows very quickly and can easily proliferate under aerobic conditions.

Accordingly, in the present invention, as an alternative to overcome the high complexity, low safety, and low economic feasibility of the conventional production method, a method of splitting the toxin protein to produce segments/fragments of toxin protein and then assembling the same in vitro was devised. According to this method, if *Clostridium botulinum* or *Escherichia coli* has only a part of the toxin gene, even if it is exposed to the environment or a workplace, only inactive protein fragments are expressed, so there is no harm to the environment. In addition, although the enzymatic activity for cleaving SNARE exists in the light chain, the neurotoxicity of the light chain alone decreases to one hundred millionths of the original amount thereof, has no ability to attach to nerve cells, loses the ability to permeate into the cytoplasm and thus has almost no toxicity to animals (Fernandez-Salas E et al., PLoS ONE, 7(11): e49516 (2012)). In addition, the heavy chain alone exhibits no toxicity because the active site is removed. Naturally, a form in which part of the heavy chain or part of the light chain is lost also exhibits no toxicity. That is, the split production of toxin protein enables safe and economical production of botulinum toxin simply by meeting requirements that individual fragment proteins be produced easily in split forms and that they bind well as active forms.

The method according to the present invention is capable of preventing cell penetration and avoiding toxicity during production due to the absence of an active light chain by producing the botulinum toxin protein as separate parts, specifically, the complex of the light chain with the translocation domain of the heavy chain, and the receptor-binding domain of the heavy chain. In addition, the method has an advantage in that, by designing a protein complex in a form that can be reconjugated through an intein protein or an affinity tag at each protein terminus, activity comparable to that of the conventional botulinum toxin can be obtained through simple mixing, without any particular process after the protein is produced. In addition, the conventional method for extracting botulinum toxin using a *Clostridium botulinum* strain has a disadvantage in that an anaerobic environment must be created and it takes a long time, more than 100 hours, to culture the bacterium. However, when the botulinum toxin is produced from the plasmid based on transformation through a split method using *E. Coli* as the strain, the culture time is shortened to less than 24 hours. In particular, according to the method of the present invention, the reaction of producing and mixing inactive fragments is complete within 5 minutes, and the botulinum toxin can be easily purified through affinity membrane centrifugation, so the total time to produce the botulinum toxin can be shortened to 30 minutes. That is, in other words, it is not necessary to perform the overall production process from start to finish at one production site, and rapid assembly from raw materials is possible.

Hereinafter, the present invention will be described in more detail with reference to the following examples. However, these examples are provided only for illustration of the present invention and should not be construed as limiting the scope of the present invention.

Example 1. Preparation of Plasmid for Producing Botulinum Toxin Split Fragment 1-1. Plasmids for Producing Two Split Fragments In order to prepare plasmids for producing a botulinum toxin split protein including two fragments, specifically, a complex [LC-$H_N$] of a light chain (LC) and a translocation domain of the heavy chain (HC), and a receptor-binding domain (RBD) of the heavy chain ($H_C$) (4 and 3 in FIG. 2), pET 28b, duet, and pCola duet were cloned using a vector and T4 DNA polymerase. Specifically, PCR was performed using a pET 28b vector and primers designed such that the two 15 bp terminals of the LC-$H_N$-Cfa$^N$ insert were complementary to each other. PCR was performed using pET duet and pCola duet vectors and primers designed such that LC was used for the RBS1 site, and two 15 bp terminals of the $H_N$-Cfa$^N$ insert were complementary to each other for the RBS2 site. In addition, production of the pET 28b vector and Cfa$^C$-$H_C$ insert was also performed. After completion of PCR, treatment with Dpn1 solution was performed at 37° C. for 1 hour to prevent self-ligation, and PCR products other than DNA were removed. To ligate the produced pET 28b, duet, and pCola duet vectors with LC-$H_N$-Cfa$^N$ insert and ligate the pET 28b vector with the Cfa$^C$-$H_C$ insert, reaction was allowed to occur in the presence of a T4 DNA polymerase for 2 minutes and 30 seconds at room temperature and for 10 minutes on ice, to induce stable hydrogen bonding between pET 28b, duet, and pCola duet vectors and LC-$H_N$-Cfa$^N$. 4 μL of each DNA solution obtained through the cloning process was added to 100 μL of a competent cell E. coli TOP10 solution, and the resulting cell solution was incubated on ice for 30 minutes and then heat-treated at 42° C. for 45 seconds. The reaction solution was added with 900 μL of Luria-Bertani (LB) liquid medium and then cultured at 37° C. for 1 hour, and the cells were collected by centrifugation (13,000 rpm, 10 minutes). The collected cell solution (0.1 mL) was plated and cultured in kanamycin LB solid medium (37° C.), and one of the formed colonies was added to a 10 mL LB liquid medium containing 0.1% kanamycin and cultured at 37° C. for 18 hours. The resulting culture solution was sonicated and purified to obtain each plasmid. The sequence of the plasmid was identified by the manufacturer (Bionics, Korea). In the production of botulinum toxin, each sequence corresponding to the His-tag was relatively short, so the specific short sequence was inserted into the specific DNA using a site-directed mutagenesis method rather than a method using T4 DNA polymerase. As a result, the LC (light chain)-$H_N$ (heavy chain translocation domain)-Cfa$^N$-His6-type botulinum toxin split protein and His6-Cfa$^C$-$H_C$ (heavy chain receptor-binding domain)-type botulinum toxin split protein were produced. (LCH$_N$-Cfa$^N$-His6 and His6-Cfa$^C$-$H_C$ in FIGS. 3a and 3b). The sequences of primers used in the process (Table 5), detailed compositions and reaction conditions are as follows:

TABLE 5

| Name | Target | Sequence | Sequence No. |
|---|---|---|---|
| pCDLCHn insert FW | LC-Hn | ATAAGGAGATATACCATGCCATTCGTTAATAAGCAATTTAACTACAAA-GACCCAGTAAA (59 mer) | 55 |
| pCDLCHN insert BW | LC-Hn | GTGATGGCTGCTGCCATTCTTAATATACTCAGTAAAGGTGCTAAGCAACTTTTT-ATTATCCAC (63 mer) | 56 |
| pCDLCHN vector BW | pCola duet pET duet | GGCAGCAGCCATACCATCATCAC (24 mer) | 57 |
| pCDLCHN vector BW | pCola duet pET duet | GGTATATCTCCTTATTAAAGTTAAACAAAATTATTTCTACAGGGGAATTGTTAT (54 mer) | 58 |
| Col FW | pCola duet | TCAGCTCCGCCATCGCCGCTTC (22 mer) | 59 |
| Col BW | pCola duet | TCGCAGCAGCGGTTTCTTTACCAGACTC (23 mer) | 60 |
| pCLC insert FW | LC | ATAAGGAGATATACCATGCCATTCGTTAATAAGCAATTTAACTACAAA-GACCCAGTAAA (59 mer) | 61 |
| pCLC insert BW | LC | GTGATGGCTCTGCCTTTGAATGGAATAATTCCGCGTACGCATAACAATTTGTAG (34 mer) | 62 |
| pCDHC vector FW | pCola duet pET duet | GGCAGCAGCCATCACCATCATCAC (24 mer) | 63 |
| pCDHC vector FW | pCola duet pET duet | CATGGTATATCTCCTTATTAAAGTTAAACAAAATTATTTCTACAGGGGAAT (51 mer) | 64 |

TABLE 5-continued

| Name | Target | Sequence | Sequence No. |
|---|---|---|---|
| pCHC insert FW | HC | AGGAGATATACCATGATAGTTAATACCAGTATCTTATCTATCGTTTA-CAAAAAGGATG ACCTGATA (86 mer) | 65 |
| pCHC insert BW | HC | GTGATGGCTGCTGCCTAAGCTACTTTCTCCCCATCCGTCGTCGACGGGGAT-GAACTCC CA (60 mer) | 66 |
| pCHN insert FW | Hn | AGGAGATATACCATGACGAAGTCTTTAGATGAAGGTTACAATAAGGCACTGAAT (54 mer) | 67 |
| pCHN insert BW | Hn | GTGATGGCTGCTGCCATTCTTAATATACTCAGTAAAGGTGCTAAGCAACTTTTT-ATTA TTATCCAC (63 mer) | 68 |
| CfaC insert FW | CfaC | ATAAGGAGATATACCATGGTCAAGATCATTAGTCGTAAGAGTCTGGG | 69 |
| CfaC insert BW | CfaC | ATTCGGATCCTGGCTTAAGCTACTTTCTCCCCATCCGTCGTC | 70 |
| Cfac vector FW | pET 28a CfaC | AGCCAGGATCCGAAT (18 mer) | 71 |
| CfaC vector BW | pET 28a Cfac | GGTATATCTCCTTAT (15 mer) | 72 |
| CfaN insert FW | CfaN | GAGTATATTAAGAATTGCCTGTCTTACGACACAGAGATTCTGAC (44 mer) | 73 |
| CfaN insert BW | CfaN | GTGATGGCTGCTGCCATGATGATGATGATGATGCGGCAAACCAT-CAACTTGTTTCAGG TCTAAC (84 mer) | 74 |
| CfaN vector FW | pCola duet CfaC | GGCAGCAGCCATCAC (15 mer) | |
| CfaN vector BW | pCola duet CfaC | ATTCTTAATATACTC (15 mer) | |

PCR composition: forward primer 1 μL, backward primer 1 μL, vector 1 μL, dNTP 4 μL, 10× reaction buffer 5 μL, Pfu DNA polymerase 0.5 μL and distilled water 37.5 μL;
PCR conditions of vector:
① Initial denaturation (95° C., 3 min),
② 30 cycles: denaturation (95° C., 3 sec), annealing (61° C., 3 sec) and extension (72° C., 6 min), and
③ (Final extension (72° C., 3 min);
PCR conditions of Insert
① Initial denaturation (95° C., 3 min),
② 30 cycles: denaturation (95° C., 3 sec), annealing (61° C., 3 sec) and extension (72° C., 1 min), and
③ (Final extension (72° C., 3 min);
Dpn1 treatment conditions (37° C., 1 hour): 5 μL (10× reaction buffer 4)+44 μL (PCR product of vector or insert)+1 μL (Dpn1 solution); and
Treatment with T4 DNA polymerase: 1 μL (vector solution)+7 μL (insert solution)+1 μL (10× reaction buffer 2.1)+1 μL (T4 DNA polymerase solution).
$T_m$ of all primers is 65° C.;
PCR composition and Dpn1 treatment conditions are the same as in the above plasmid production method
Purchase source of Dpn1, 10× reaction buffer, 10× reaction buffer 4, 10× reaction buffer 2.1, Pfu DNA polymerase T4 DNA polymerase and dNTP (2.5 mM): ELPIS BIOTECH, Korea; and
PCR product purification and plasmid preparation: in accordance with the protocol contained in Dokdo-prep Gel extraction kit spintype 200 (ELPIS).
1-2. Plasmids for Producing Three Split Fragments
To prepare plasmids for producing a botulinum toxin split protein (1, 2 and 3 in FIG. 2) including three fragments of LC, a translocation domain of HC ($H_N$) and a receptor-binding domain of HC ($H_C$), LC, $H_N$-Cfa$^N$, Cfa$^C$-$H_C$ inserts, and pET 28b, duet, and pCola duet were produced by PCR, after which LC, $H_N$-Cfa$^N$ and Cfa$^C$$H_C$ were ligated. Each plasmid was produced by cloning in the same manner as in Example 1-1.

Example 2. Identification of Soluble Expression of Botulinum Toxin Split Fragment A botulinum toxin split protein was produced using the plasmids produced in Example 1. Specifically, heat shock was applied to the *E. coli* BL21 (DE3) strain transformed with competent cells at 42° C. for 45 seconds, and the *E. coli* BL21 (DE3) strain was stabilized on ice and transduced with the plasmids produced as described above. The transduced *E. coli* was plated on LB ampicillin solid selective medium and then incubated at 37° C. for one day. One colony grown in the selective medium was added to 10 mL of liquid LB medium, added with 10 μL of kanamycin, and then pre-cultured at 37° C. for 12 hours. The pre-cultured recombinant strain was inoculated at 1% in 50 mL LB medium supplemented with kanamycin and cultured at 37° C. until the O.D. (at a wavelength of 600 nm) reached 0.5. Then, the strain was added with 0.1 mM IPTG and cultured at 16° C. for 24 hours. The resulting culture solution was centrifuged at 5,000 rpm at 4° C. for 10 minutes to remove the medium and thereby obtain strains. The strains were resuspended in 10 mL of PBS (137 mM NaCl, 2.7 mM KCl, 2.55 mM $Na_2HPO_4$, and 1.47 mM $KH_2PO_4$, pH 7.4) and then sonicated for 1 minute 45 seconds at an interval of 1 second to disrupt the cells. Whether or not soluble expression occurred in each of the entire cell, a soluble cell portion, and an insoluble cell portion was identified. For separation between the soluble portion and the insoluble portion, centrifugation was performed again at 4° C. at 13,000 rpm for 10 minutes to obtain a supernatant as a water-soluble portion, and an insoluble portion was resuspended. Each sample was added with 6×SDS solution (based on 10 ml of 6×SDS loading buffer: 7 mL of 0.5 M Tris-HCl (pH 6.8), 2.6 mL of 100% glycerol, 1 g of DTT, 60 μL of 10% Bromophenol blue and 400 μL of 10% SDS), thermal shock was applied thereto at 95° C. for 10 minutes, the resulting sample was allowed to cool, and the sample was identified through SDS PAGE electrophoresis on a 12% SDS gel at 80 V for 20 minutes and at 140 V for 1 hour and 20 minutes over a total period of 1 hour and 40 minutes. The loading order was the entire cell, the water-soluble portion, and the insoluble portion.

As a result, LC expression was confirmed in entire-cell, soluble and insoluble portions. For $H_C$, the protein was expressed in entire-cell, soluble and insoluble portions. For $H_N$, it was difficult to detect the same by SDS PAGE, so a Western blotting analysis method using a Histag antibody was used, and only the bands corresponding to the entire-cell and insoluble-portion appeared, and thus expression was identified (FIG. 4).

Example 3. Full-Length Botulinum Toxin Production Through Reconjugation of Botulinum Toxin Split Fragments 3-1. Purification of Botulinum Toxin Fragments and Reconjugation Thereof Using Protein Trans-Splicing Each fragment was produced in the same manner as in Example 2 using the plasmids produced in Example 1. Specifically, heat shock was applied to the *E. coli* BL21 (DE3) strain transformed with competent cells at 42° C. for 45 seconds, after which the strain was stabilized on ice and transduced with the plasmids produced above. The transduced *E. coli* was plated on LB ampicillin solid selective medium and then incubated at 37° C. for one day. One colony grown in the selective medium was added to 10 mL of liquid LB medium, added with 10 μL of ampicillin, and then pre-cultured at 37° C. for 12 hours. The pre-cultured recombinant strain was inoculated again in 50 mL LB medium supplemented with ampicillin at 1% and incubated at 37° C. until the O.D. (at a wavelength of 600 nm) reached 0.5. Then, the strain was added with 0.1 mM IPTG and cultured at 18° C. for 24 hours. The culture solution was centrifuged at 5,000 rpm at 4° C. for 10 minutes to remove the medium and thereby obtain strains. The strains were resuspended in 10 mL of PBS (137 mM NaCl, 2.7 mM KCl, 2.55 mM Na 2HPO$_4$ and 1.47 mM KH$_2$PO$_4$) and sonicated for 1 minute and 45 seconds at an interval of 1 second to disrupt the cells. The precipitate was removed by centrifugation at 4° C. at 13,000 rpm for 10 minutes. In order to separate the expressed botulinum toxin split protein suspended in the lysate from which the precipitate had been removed, the LC-Hn-Cfa$^N$-His6 and His6-Cfa$^C$-Hc botulinum toxin split proteins were allowed to attach to the beads via His-tag through nutation movement for 2 hours in a 4° C. column containing Ni-NTA beads. After nutation movement, the proteins were washed with PBS to remove impurities excluding the botulinum toxin (FIGS. 5 and 6). At this time, the LC-Hn-Cfa$^N$-His6 protein complex was treated with an artificial enzyme such as trypsin to cleave the complex into two units at the cleavage site between LC and Hn, thereby finally making the protoxin active. LC, Hn-Cfa$^N$-His6, and His6-Cfa$^C$-Hc obtained by splitting the protein into three fragments were attached to the beads without enzymatic treatment as described above. Then, the washed column was treated with a 150 mM imidazole solution to detach the protein from the beads and thereby obtain each botulinum toxin split protein. The purified split proteins were mixed to induce trans-splicing between Cfa$^N$ and Cfa$^C$ to form the bond between the intein at the N-terminus of Hn and the intein at the C-terminus of Hc. The resulting bond is detached therefrom, resulting in synthesis of intact botulinum toxin. Proteins that have undergone trans-splicing are present in the final form of LC-Hn-HC, that is, an aqueous solution containing botulinum toxin. In order to remove the non-reacted substances mixed therewith, the aqueous solution was made to flow once more into the Ni-NTA beads to attach the remaining His$_6$-Cfa$^C$-Hc fragment to the beads and thereby obtain a pure botulinum toxin. Whether or not protein trans-splicing between LC-H$_N$-Cfa$^N$ and Cfa$^C$-F$_c$ actually occurred was determined through Western blot analysis. The result showed that 150 kDa full-length toxin was assembled after 1 hour (FIG. 7).

3-2. Reconjugation Using Leucine Zipper

Reconjugation of the botulinum toxin fragments was performed using a leucine zipper. Specifically, to produce a leucine zipper, during the plasmid production of Example 1, for the pET vector, EE1234L was cloned into the terminus of Hn, and EE1234L was cloned into the C-terminus of Hc. *E. coli* Top10 cells were transformed with the result, and then each plasmid was obtained using a plasmid miniprep method. Then, split fragments were produced and purified in the same manner as in Examples 2 and 3-1 and then reacted to obtain the final botulinum toxin.

3-3. Reconjugation Using Affinity Tags

In the plasmid production of Example 1, SpyTag or SpyCatcher was cloned into the C-terminus of H$_N$ or the –N terminus of H$_C$, and then the result was transformed into *E. coli* Top10 to obtain a plasmid. Then, each split fragment was produced and purified in the same manner as in Examples 2 and 3-1, and then each purified fragment was reacted at a temperature of 4 to 37° C. to obtain a final botulinum toxin. Here, SpyTag is a peptide that binds to SpyCatcher to form an isopeptide bond, and is found in CnaB1 or CnaB2 domains in pilin and adhesins of Gram-positive bacteria. To obtain this, the Cnab2 domain was split into SpyTag and SpyCatcher from FbaB, which is a fibronectin-binding protein of *Streptococcus pyogenes* (spy). CnaB2 was split into a 13-residue peptide (SpyTag) and a 116-residue domain (SpyCatcher). These two parts are characterized by spontaneously forming isopeptide bonds at a temperature of 4 to 37° C. and a pH of 5 to 8 even in the presence of a wide range of buffers and non-ionic detergents (Zakeri, B., Fierer, 2012), and such a peptide performs the function when bound either to the N-terminus or to the C-terminus.

Example 4. Confirmation of Dimer Formation Through Disulfide Bond Formed in Cysteine after Trans-Intein Splicing SDS-PAGE and size exclusion chromatography (SEC) were used to determine whether or not two LC-H$_N$-H$_C$ formed a dimer through the disulfide bond in the cysteine newly generated in the splicing process of Example 3-1. Specifically, in the same manner as in Example 2, electrophoresis was performed using SDS-PAGE. At this time, a 6×SDS solution containing DTT, which serves to cleave disulfide bonds, and a solution not containing DTT were compared. In addition, a graph was drawn using SEC, and the size of the full-length toxin was observed in order to identify the presence or absence of disulfide bonds.

The result showed that bands were formed at 150 kDa in the graph of the electrophoresed gel and SEC of the sample using the solution containing DTT, whereas the band was formed at 300 kDa of the sample using the solution containing no DTT. This indicates that the toxin formed a dimer through formation of a disulfide bond in the cysteine produced through trans-intein splicing.

Example 5. Production of Cholesterol or Fatty-Acid-Modified Full-Length Botulinum Toxin In order to reduce the side effects caused by the diffusion of botulinum toxin into the surrounding or circulation thereof through the blood, an ultra-low diffusion-type botulinum toxin that is imparted with prolonged protein half-life and reduced diffusion was produced by modifying the toxin with fatty acids or cholesterol. Specifically, at least one fatty acid selected from caprylic acid (C8), capric acid (C10), lauric acid (C12), myristic acid (C14), palmitic acid (C16), and stearic acid (C18) (two fatty acids are prepared using the reactivity of PDP-PE (1,2-dioleoyl-sn-glycero-3-phosphoethanolamine-N-[3-(2-pyridyldithio)propionate]) was attached to the lysine or cysteine residues of the produced full-length botulinum toxin or attached to the cysteine newly generated during the splicing process of Example 3-1. In particular, attachment thereof to the newly generated cysteine can minimize the effects on the structure of the toxin. Here, a cholesterol transfer substance such as a cysteine-reactive 2-bromoacetyl moiety was used to modify botulinum toxin with cholesterol.

Example 6. Protein Trans-Splicing Using Fluorescent Protein-Based Surrogate

In order to measure the speed and efficiency of protein trans-splicing by the Cfa intein, surrogate models for $LCH_N$-$Cfa^N$-His6 and His6-$Cfa^C$-$H_C$ were used. The surrogates were mCherry-$cfa^N$-His and His-$Cfa^C$-eGFP-RGD, which replace $LCH_N$-$Cfa^N$-His6 and His6-$Cfa^C$-$H_C$, respectively. To construct the surrogates, a fluorescent protein was inserted into the pET 28b plasmid in the same manner as in Example 1, and each fragment was produced in the same manner as in Example 2. Specifically, heat shock was applied to the E. coli BL21 (DE3) strain transformed with competent cells at 42° C. for 45 seconds, then stabilized on ice and transduced with the plasmids produced above. The transduced E. coli was plated on LB kanamycin solid selective medium and then incubated at 37° C. for one day. One colony grown in the selective medium was added to 10 mL of liquid LB medium, added with 10 μL of kanamycin, and then pre-cultured at 37° C. for 12 hours. The pre-cultured recombinant strain was again cultured at 1% in 600 mL LB medium containing kanamycin and cultured at 37° C. until the O.D. (at a wavelength of 600 nm) reached 0.5. The strain was added with 0.1 mM IPTG and cultured at 16° C. for 24 hours. The culture solution was centrifuged at 5,000 rpm at 4° C. for 10 minutes to remove the medium and to obtain strains. Then, the strains were resuspended in 25 mL of a buffer solution (500 mM NaCl, 20 mM Tris-HCl, 10 mM imidazole, pH 8.0), and sonicated at an interval of 1 second for 1 minute and 45 seconds to disrupt cells, and the precipitate was removed by centrifugation again at 4° C. at 12,000 rpm for 30 minutes. In order to separate the expressed botulinum toxin split protein suspended in the lysate from which the precipitate had been removed, the mCherry-$Cfa^N$-His6 and His6-$Cfa^C$-eGFP-RGD botulinum toxin split proteins were allowed to attach to the beads via His-tag through nutation movement for 2 hours in a 4° C. column containing Ni-NTA beads. After nutation movement, the proteins were washed with buffer (500 mM NaCl, 20 mM Tris-HCl, 30 mM imidazole, pH 8.0) to remove impurities excluding the fluorescent protein. Then, the washed column was treated with a 250 mM imidazole solution to detach the protein from the beads and thereby obtain the fluorescent protein. The concentration of purified proteins was measured by DC protein assay. The result showed that the concentration of mCherry-$Cfa^N$-His was 91.07 μM, the concentration of His-$Cfa^C$-$H_C$ was 8.23 μM, the concentration of $LCH_N$-$Cfa^N$-His was 3.98 μM, and the concentration of His-$Cfa^C$-eGFP was 59.1 μM. mCherry-$Cfa^N$-His, and His-$Cfa^C$-$H_C$ were each diluted at 1×, 5×, 10×, 20×, and 40× with PBS (137 mM NaCl, 2.7 mM KCl, 2.55 mM $Na_2HPO_4$ and 1.47 mM $KH_2PO_4$, pH 7.4) buffer. In addition, $LCH_N$-$Cfa^N$-His was diluted at 1×, 2× and 4× with PBS (137 mM NaCl, 2.7 mM KCl, 2.55 mM $Na_2HPO_4$ and 1.47 mM $KH_2PO_4$, pH 7.4), and His-$Cfa^C$-eGFP was diluted at 1×, 2×, 4×, 8×, 16× and 32× therewith. The predicted size was verified using 12% SDS PAGE after addition with 6×SDS sample buffer (FIG. 8).

The two purified fluorescent proteins were reacted with botulinum split toxins having an intein terminus corresponding to each intein terminus thereof. $LCH_N$-$Cfa^N$-His6 and His6-$Cfa^C$-eGFP-RGD, and mCherry-$cfa^N$-His6 and His6-$Cfa^C$$H_C$ were used, respectively, and were added with 2 mM TCEP and incubated at 37° C. for 30 minutes, and reaction was performed at molar ratios of $Cfa^N$ and $Cfa^C$ of 1:1, 2:1, and 1:2. The molar concentration (molarity) was measured though DC assay using a spectrometer. Each pair was reacted for 0 minutes, 5 minutes, 10 minutes, 30 minutes, and 1 hour, and the sample was subjected to SDS electrophoresis every hour.

It was observed that $LCH_N$-eGFP-RGD started to react 5 minutes after binding of $LCH_N$-$Cfa^N$-His6 to His6-$Cfa^C$-eGFP-RGD at all ratios of $Cfa^N$ to $Cfa^C$ of 1:1, 2:1, 1:2, 3:1 and 1:3. At the ratio of $Cfa^N$ to $Cfa^C$ of 1:1, the reaction efficiency was the best. In addition, it was observed that mCherry-$H_C$ appeared at a predicted size 5 minutes after binding of mCherry-$cfa^N$-His6 to His6-$Cfa^C$-$H_C$ at ratios of $Cfa^N$ to $Cfa^C$ of 1:1, 2:1, and 1:2. The efficiency at the ratio of $Cfa^N$ to $Cfa^C$ of 1:1 was the best in both the $LCH_N$-eGFP-RGD and mCherry-$H_C$ (FIG. 9).

Example 7. Identification of SNAP-25 Protein Cleavage Activity of Botulinum Toxin SNAP-25 was purified in order to determine whether or not the split fragments of the botulinum toxin produced in the present invention or the full-length botulinum toxin produced by splicing the same have cleavage activity for the SNAP-25 protein. Specifically, heat shock was applied to the E. coli BL21 (DE3) strain transformed with competent cells at 42° C. for 45 seconds, then stabilized on ice and transduced with the plasmids produced above. The transduced E. coli was plated on LB kanamycin solid selective medium, and then cultured at 37° C. for one day. One colony grown in the selective medium was added to 10 mL of liquid LB medium, added with 10 μL of kanamycin, and then pre-cultured at 37° C. for 12 hours. The pre-cultured recombinant strain was again inoculated at 1% in 600 mL LB medium containing kanamycin and cultured at 37° C. until the O.D. (at a wavelength of 600 nm) reached 0.5. Then, the strain was added with 0.1 mM IPTG and cultured at 16° C.

for 12 hours. The culture solution was centrifuged at 8,000 rpm at 4° C. for 10 minutes to remove the medium and obtain strains. The strains were resuspended in 10 mL of PBS (137 mM NaCl, 2.7 mM KCl, 2.55 mM $Na_2HPO_4$, and 1.47 mM $KH_2PO_4$, pH 7.4) and then sonicated for 1 minute 45 seconds at an interval of 1 second to disrupt the cells. The residue was centrifuged again at 4° C. at 12,000 rpm for 40 minutes to remove the precipitate. In order to separate the expressed SNAP-25 suspended in the lysate from which the precipitate had been removed, the cells were allowed to attach to beads through His-tag by nutation for 2 hours in a 4° C. column containing Ni-NTA beads. After the nutation movement, the cells were washed with a solution of PBS (137 mM NaCl, 2.7 mM KCl, 2.55 mM $Na_2HPO_4$, 1.47 mM $KH_2PO_4$, 30 mM imidazole, pH 7.4) to remove impurities excluding SNAP-25. Then, the washed column was treated with a 250 mM imidazole solution to detach the proteins from the beads to thereby obtain SNAP-25 alone. At this time, in the same manner as in Example 2, electrophoresis was performed using SDS PAGE to measure the expression and concentration of purified SNAP-25. The SNAP-25 was diluted and then added with the predetermined concentration of light chain (LC) and full-length botulinum toxin, and reaction was allowed to proceed for 1 hour. SNAP-25 containing no toxin was used as a control. Whether or not SNAP-25 was cleaved by botulinum toxin in vitro was determined through SDS-PAGE (FIG. 10) The result showed that SNAP-25 was cleaved by the activity of LC.

---

The invention claimed is:

1. A method of producing botulinum toxin, the method comprising:
   1) separately expressing and producing a botulinum toxin fragment (LC-H$_N$-Intein N-Tag) comprising a light chain of botulinum toxin (LC), a translocation domain of a botulinum toxin heavy chain (H$_N$), intein N (INT-N), and a tag for purification (Tag) linked to one another sequentially from a 5' end to a 3' end, and a botulinum toxin fragment (Tag-Intein C-H$_C$) comprising a tag for purification (Tag), Intein C (INT-C), and a receptor binding domain of botulinum toxin heavy chain (Hc) linked to one another sequentially from a 5' end to a 3' end;
   2) separately purifying the botulinum toxin fragment (LC-H$_N$-Intein N-Tag) and the botulinum toxin fragment (Tag-Intein C-H$_C$);
   3) cleaving a peptide bond between the light chain (LC) and the translocation domain of the heavy chain (H$_N$)

and inducing a disulfide bond between the cleaved light chain (LC) and the translocation domain of the heavy chain ($H_N$); and 4) removing the Intein N-Tag linked to the translocation domain of the heavy chain ($H_N$) and the Tag-Intein C linked to the receptor binding domain of the heavy chain ($H_C$) by trans-splicing to bind the translocation domain of the heavy chain ($H_N$) to the receptor binding domain of the heavy chain ($H_C$) without the tag for purification.

2. The method according to claim 1, wherein the expression is carried out by expression using *E. coli* as a host cell.

* * * * *